(12) United States Patent
Weber et al.

(10) Patent No.: US 8,449,603 B2
(45) Date of Patent: May 28, 2013

(54) ENDOPROSTHESIS COATING

(75) Inventors: Jan Weber, Maastricht (NL); Liliana Atanasoska, Edina, MN (US); Michele Zoromski, Minneapolis, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 187 days.

(21) Appl. No.: 12/486,295

(22) Filed: Jun. 17, 2009

(65) Prior Publication Data

US 2009/0319032 A1    Dec. 24, 2009

Related U.S. Application Data

(60) Provisional application No. 61/073,647, filed on Jun. 18, 2008.

(51) Int. Cl.
*A61F 2/82* (2006.01)

(52) U.S. Cl.
USPC .......................................... 623/1.48; 427/2.1

(58) Field of Classification Search
USPC .................. 623/1.42–1.48; 424/424; 427/2.1
See application file for complete search history.

(56) References Cited

U.S. PATENT DOCUMENTS

| | | |
|---|---|---|
| 3,480,523 A | 11/1969 | Tyrrell |
| 3,751,283 A | 8/1973 | Dawson |
| 3,758,396 A | 9/1973 | Vieth et al. |
| 3,910,819 A | 10/1975 | Rembaum et al. |
| 3,948,254 A | 4/1976 | Zaffaroni |
| 3,952,334 A | 4/1976 | Bokros et al. |
| 3,970,445 A | 7/1976 | Gale et al. |
| 3,993,072 A | 11/1976 | Zaffaroni |
| 4,044,404 A | 8/1977 | Martin et al. |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,309,996 A | 1/1982 | Theeuwes |
| 4,321,311 A | 3/1982 | Strangman |
| 4,330,891 A | 5/1982 | Branemark et al. |
| 4,334,327 A | 6/1982 | Lyman et al. |
| 4,401,546 A | 8/1983 | Nakamura et al. |
| 4,407,695 A | 10/1983 | Deckman et al. |
| 4,475,972 A | 10/1984 | Wong |
| 4,565,744 A | 1/1986 | Walter et al. |

(Continued)

FOREIGN PATENT DOCUMENTS

| | | |
|---|---|---|
| AT | 232704 | 3/2003 |
| AT | 288234 | 2/2005 |

(Continued)

OTHER PUBLICATIONS

Brukner et al., "Metal plasma immersion ion implantation and deposition (MPIIID): chromium on magnesium," Surface and Coatings Technology vol. 103-104, pp. 227-230, (1998).

(Continued)

*Primary Examiner* — Suzette J Gherbi
(74) *Attorney, Agent, or Firm* — Fish & Richardson P.C.

(57) ABSTRACT

An endoprosthesis, e.g., a stent (e.g., a drug eluting stent), that includes a porous surface and hollow elements integrated with a coating on the surface and a method of making the same are disclosed.

12 Claims, 7 Drawing Sheets

U.S. PATENT DOCUMENTS

| | | |
|---|---|---|
| 4,585,652 A | 4/1986 | Miller et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,733,665 A | 3/1988 | Palmaz |
| 4,738,740 A | 4/1988 | Pinchuk et al. |
| 4,743,252 A | 5/1988 | Martin, Jr. et al. |
| 4,784,659 A | 11/1988 | Fleckenstein et al. |
| 4,800,882 A | 1/1989 | Gianturco |
| 4,842,505 A | 6/1989 | Annis et al. |
| 4,886,062 A | 12/1989 | Wiktor |
| 4,902,290 A | 2/1990 | Fleckenstein et al. |
| 4,954,126 A | 9/1990 | Wallsten |
| 4,976,692 A | 12/1990 | Atad |
| 4,994,071 A | 2/1991 | MacGregor |
| 5,061,275 A | 10/1991 | Wallsten et al. |
| 5,061,914 A | 10/1991 | Busch et al. |
| 5,073,365 A | 12/1991 | Katz et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,171,607 A | 12/1992 | Cumbo |
| 5,195,969 A | 3/1993 | Wang et al. |
| 5,205,921 A | 4/1993 | Shirkanzadeh |
| 5,219,611 A | 6/1993 | Giannelis et al. |
| 5,232,444 A | 8/1993 | Just et al. |
| 5,236,413 A | 8/1993 | Feiring |
| 5,242,706 A | 9/1993 | Cotell et al. |
| 5,250,242 A | 10/1993 | Nishio et al. |
| 5,270,086 A | 12/1993 | Hamlin |
| 5,279,292 A | 1/1994 | Baumann et al. |
| 5,290,585 A | 3/1994 | Elton |
| 5,302,414 A | 4/1994 | Alkhimov et al. |
| 5,304,121 A | 4/1994 | Sahatjian |
| 5,314,453 A | 5/1994 | Jeutter |
| 5,322,520 A | 6/1994 | Milder |
| 5,326,354 A | 7/1994 | Kwarteng |
| 5,348,553 A | 9/1994 | Whitney |
| 5,366,504 A | 11/1994 | Andersen et al. |
| 5,368,881 A | 11/1994 | Kelman et al. |
| 5,378,146 A | 1/1995 | Sterrett |
| 5,380,298 A | 1/1995 | Zabetakis et al. |
| 5,383,935 A | 1/1995 | Shirkhanzadeh |
| 5,397,307 A | 3/1995 | Goodin |
| 5,405,367 A | 4/1995 | Schulman et al. |
| 5,439,446 A | 8/1995 | Barry |
| 5,443,496 A | 8/1995 | Schwartz et al. |
| 5,447,724 A | 9/1995 | Helmus et al. |
| 5,449,373 A | 9/1995 | Pinchasik et al. |
| 5,449,382 A | 9/1995 | Dayton |
| 5,464,450 A | 11/1995 | Buscemi et al. |
| 5,464,650 A | 11/1995 | Berg et al. |
| 5,474,797 A | 12/1995 | Sioshansi et al. |
| 5,500,013 A | 3/1996 | Buscemi et al. |
| 5,527,337 A | 6/1996 | Stack et al. |
| 5,545,208 A | 8/1996 | Wolff et al. |
| 5,551,954 A | 9/1996 | Buscemi et al. |
| 5,569,463 A | 10/1996 | Helmus et al. |
| 5,578,075 A | 11/1996 | Dayton |
| 5,587,507 A | 12/1996 | Kohn et al. |
| 5,591,224 A | 1/1997 | Schwartz et al. |
| 5,603,556 A | 2/1997 | Klink |
| 5,605,696 A | 2/1997 | Eury et al. |
| 5,607,463 A | 3/1997 | Schwartz et al. |
| 5,607,467 A | 3/1997 | Froix |
| 5,609,629 A | 3/1997 | Fearnot et al. |
| 5,614,549 A | 3/1997 | Greenwald et al. |
| 5,624,411 A | 4/1997 | Tuch |
| 5,649,951 A | 7/1997 | Davidson |
| 5,649,977 A | 7/1997 | Campbell |
| 5,672,242 A | 9/1997 | Jen |
| 5,674,192 A | 10/1997 | Sahatjian et al. |
| 5,674,242 A | 10/1997 | Phan et al. |
| 5,679,440 A | 10/1997 | Kubota |
| 5,681,196 A | 10/1997 | Jin et al. |
| 5,690,670 A | 11/1997 | Davidson |
| 5,693,085 A | 12/1997 | Buirge et al. |
| 5,693,928 A | 12/1997 | Egitto et al. |
| 5,711,866 A | 1/1998 | Lashmore et al. |
| 5,733,924 A | 3/1998 | Kanda et al. |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,758,562 A | 6/1998 | Thompson |
| 5,761,775 A | 6/1998 | Legome et al. |
| 5,769,883 A | 6/1998 | Buscemi et al. |
| 5,772,864 A | 6/1998 | M.o slashed.ller et al. |
| 5,776,184 A | 7/1998 | Tuch |
| 5,780,807 A | 7/1998 | Saunders |
| 5,788,687 A | 8/1998 | Batich et al. |
| 5,788,979 A | 8/1998 | Alt et al. |
| 5,795,626 A | 8/1998 | Gabel et al. |
| 5,797,898 A | 8/1998 | Santini, Jr. et al. |
| 5,807,407 A | 9/1998 | England et al. |
| 5,817,046 A | 10/1998 | Glickman |
| 5,824,045 A | 10/1998 | Alt |
| 5,824,048 A | 10/1998 | Tuch |
| 5,824,049 A | 10/1998 | Ragheb et al. |
| 5,824,077 A | 10/1998 | Mayer |
| 5,830,480 A | 11/1998 | Ducheyne et al. |
| 5,837,313 A | 11/1998 | Ding et al. |
| 5,843,089 A | 12/1998 | Sahatjian et al. |
| 5,843,172 A * | 12/1998 | Yan ............................... 623/1.42 |
| 5,852,088 A | 12/1998 | Dismukes et al. |
| 5,858,556 A | 1/1999 | Eckert et al. |
| 5,873,904 A | 2/1999 | Ragheb et al. |
| 5,874,134 A | 2/1999 | Rao et al. |
| 5,879,697 A | 3/1999 | Ding et al. |
| 5,882,335 A | 3/1999 | Leone et al. |
| 5,888,591 A | 3/1999 | Gleason et al. |
| 5,891,108 A | 4/1999 | Leone et al. |
| 5,891,192 A | 4/1999 | Murayama et al. |
| 5,902,266 A | 5/1999 | Leone et al. |
| 5,922,021 A | 7/1999 | Jang |
| 5,928,247 A | 7/1999 | Barry et al. |
| 5,951,881 A | 9/1999 | Rogers et al. |
| 5,954,706 A | 9/1999 | Sahatjian |
| 5,962,136 A | 10/1999 | Dewez et al. |
| 5,968,091 A | 10/1999 | Pinchuk et al. |
| 5,968,092 A | 10/1999 | Buscemi et al. |
| 5,968,640 A | 10/1999 | Lubowitz et al. |
| 5,972,027 A | 10/1999 | Johnson |
| 5,977,204 A | 11/1999 | Boyan et al. |
| 5,980,551 A | 11/1999 | Summers et al. |
| 5,980,564 A | 11/1999 | Stinson |
| 5,980,566 A | 11/1999 | Alt et al. |
| 6,013,591 A | 1/2000 | Ying et al. |
| 6,017,577 A | 1/2000 | Hostettler et al. |
| 6,022,812 A | 2/2000 | Smith et al. |
| 6,025,036 A | 2/2000 | McGill et al. |
| 6,034,295 A | 3/2000 | Rehberg et al. |
| 6,045,877 A | 4/2000 | Gleason et al. |
| 6,063,101 A | 5/2000 | Jacobsen et al. |
| 6,071,305 A | 6/2000 | Brown et al. |
| 6,074,135 A | 6/2000 | Tapphorn et al. |
| 6,096,070 A | 8/2000 | Ragheb et al. |
| 6,099,561 A * | 8/2000 | Alt ............................... 623/1.44 |
| 6,099,562 A | 8/2000 | Ding et al. |
| 6,106,473 A | 8/2000 | Violante et al. |
| 6,110,204 A | 8/2000 | Lazarov et al. |
| 6,120,536 A | 9/2000 | Ding et al. |
| 6,120,660 A | 9/2000 | Chu et al. |
| 6,122,564 A | 9/2000 | Koch et al. |
| 6,139,573 A | 10/2000 | Sogard et al. |
| 6,139,913 A | 10/2000 | Van Steenkiste et al. |
| 6,153,252 A | 11/2000 | Hossainy et al. |
| 6,156,435 A | 12/2000 | Gleason et al. |
| 6,159,142 A | 12/2000 | Alt |
| 6,171,609 B1 | 1/2001 | Kunz |
| 6,174,329 B1 | 1/2001 | Callol et al. |
| 6,174,330 B1 | 1/2001 | Stinson |
| 6,180,184 B1 | 1/2001 | Gray et al. |

| Patent | Date | Inventor |
|---|---|---|
| 6,187,037 B1 | 2/2001 | Satz |
| 6,190,404 B1 | 2/2001 | Palmaz et al. |
| 6,193,761 B1 | 2/2001 | Treacy |
| 6,200,685 B1 | 3/2001 | Davidson |
| 6,203,536 B1 | 3/2001 | Berg et al. |
| 6,206,915 B1 | 3/2001 | Fagan et al. |
| 6,206,916 B1 | 3/2001 | Furst |
| 6,210,715 B1 * | 4/2001 | Starling et al. ............... 424/489 |
| 6,212,434 B1 | 4/2001 | Scheiner et al. |
| 6,214,042 B1 | 4/2001 | Jacobsen et al. |
| 6,217,607 B1 | 4/2001 | Alt |
| 6,231,600 B1 | 5/2001 | Zhong |
| 6,240,616 B1 | 6/2001 | Yan |
| 6,241,762 B1 | 6/2001 | Shanley |
| 6,245,104 B1 | 6/2001 | Alt |
| 6,249,952 B1 | 6/2001 | Ding |
| 6,251,136 B1 | 6/2001 | Guruwaiya et al. |
| 6,253,443 B1 | 7/2001 | Johnson |
| 6,254,632 B1 | 7/2001 | Wu et al. |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,280,411 B1 | 8/2001 | Lennox |
| 6,283,386 B1 | 9/2001 | Van Steenkiste et al. |
| 6,284,305 B1 | 9/2001 | Ding et al. |
| 6,287,331 B1 | 9/2001 | Heath |
| 6,287,332 B1 | 9/2001 | Bolz et al. |
| 6,287,628 B1 | 9/2001 | Hossainy et al. |
| 6,290,721 B1 | 9/2001 | Heath |
| 6,299,604 B1 | 10/2001 | Ragheb et al. |
| 6,306,144 B1 | 10/2001 | Sydney et al. |
| 6,315,708 B1 | 11/2001 | Salmon et al. |
| 6,315,794 B1 | 11/2001 | Richter |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,330 B1 | 12/2001 | Choy et al. |
| 6,334,856 B1 | 1/2002 | Allen et al. |
| 6,335,029 B1 | 1/2002 | Kamath et al. |
| 6,337,076 B1 | 1/2002 | Studin |
| 6,342,507 B1 | 1/2002 | Naicker et al. |
| 6,348,960 B1 | 2/2002 | Etori et al. |
| 6,358,532 B2 | 3/2002 | Starling et al. |
| 6,358,556 B1 | 3/2002 | Ding et al. |
| 6,361,780 B1 | 3/2002 | Ley et al. |
| 6,364,856 B1 | 4/2002 | Ding et al. |
| 6,365,222 B1 | 4/2002 | Wagner et al. |
| 6,367,412 B1 | 4/2002 | Ramaswamy et al. |
| 6,368,658 B1 | 4/2002 | Schwarz et al. |
| 6,379,381 B1 | 4/2002 | Hossainy et al. |
| 6,379,383 B1 | 4/2002 | Palmaz et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,052 B2 | 5/2002 | Buirge et al. |
| 6,395,325 B1 | 5/2002 | Hedge et al. |
| 6,395,326 B1 | 5/2002 | Castro et al. |
| 6,398,806 B1 | 6/2002 | You |
| 6,413,271 B1 | 7/2002 | Hafeli et al. |
| 6,416,820 B1 | 7/2002 | Yamada et al. |
| 6,419,692 B1 | 7/2002 | Yang et al. |
| 6,436,133 B1 | 8/2002 | Furst et al. |
| 6,440,503 B1 | 8/2002 | Merdan et al. |
| 6,458,153 B1 | 10/2002 | Bailey et al. |
| 6,465,052 B1 | 10/2002 | Wu |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,418 B2 | 11/2002 | Li et al. |
| 6,488,715 B1 | 12/2002 | Pope et al. |
| 6,491,666 B1 | 12/2002 | Santini, Jr. et al. |
| 6,491,720 B1 | 12/2002 | Vallana et al. |
| 6,503,921 B2 | 1/2003 | Naicker et al. |
| 6,504,292 B1 | 1/2003 | Choi et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,514,289 B1 | 2/2003 | Pope et al. |
| 6,517,888 B1 | 2/2003 | Weber |
| 6,524,274 B1 | 2/2003 | Rosenthal et al. |
| 6,527,801 B1 | 3/2003 | Dutta |
| 6,527,938 B2 | 3/2003 | Bales et al. |
| 6,530,951 B1 | 3/2003 | Bates et al. |
| 6,537,310 B1 | 3/2003 | Palmaz et al. |
| 6,544,582 B1 | 4/2003 | Yoe |
| 6,545,097 B2 | 4/2003 | Pinchuk et al. |
| 6,551,353 B1 | 4/2003 | Baker et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,585,765 B1 | 7/2003 | Hossainy et al. |
| 6,599,558 B1 | 7/2003 | Al-Lamee et al. |
| 6,607,598 B2 | 8/2003 | Schwarz et al. |
| 6,613,083 B2 | 9/2003 | Alt |
| 6,613,432 B2 | 9/2003 | Zamora et al. |
| 6,616,765 B1 | 9/2003 | Wu et al. |
| 6,620,194 B2 | 9/2003 | Ding et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,656,506 B1 | 12/2003 | Wu et al. |
| 6,660,034 B1 | 12/2003 | Mandrusov et al. |
| 6,660,343 B2 | 12/2003 | McGill et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,999 B1 | 1/2004 | Wang et al. |
| 6,676,987 B2 | 1/2004 | Zhong et al. |
| 6,676,989 B2 | 1/2004 | Kirkpatrick et al. |
| 6,689,803 B2 | 2/2004 | Hunter |
| 6,695,865 B2 | 2/2004 | Boyle et al. |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,723,120 B2 | 4/2004 | Yan |
| 6,725,901 B1 | 4/2004 | Kramer et al. |
| 6,726,712 B1 | 4/2004 | Raeder-Devens et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,736,849 B2 | 5/2004 | Li et al. |
| 6,740,077 B1 | 5/2004 | Brandau et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,761,736 B1 | 7/2004 | Woo et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,780,424 B2 | 8/2004 | Claude |
| 6,780,491 B1 | 8/2004 | Cathey et al. |
| 6,783,543 B2 | 8/2004 | Jang |
| 6,790,228 B2 | 9/2004 | Hossainy et al. |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |

| Patent | Date | Inventor |
|---|---|---|
| 6,815,609 B1 | 11/2004 | Wang et al. |
| 6,820,676 B2 | 11/2004 | Palmaz et al. |
| 6,827,737 B2 | 12/2004 | Hill et al. |
| 6,830,598 B1 | 12/2004 | Sung |
| 6,833,004 B2 | 12/2004 | Ishii et al. |
| 6,846,323 B2 | 1/2005 | Yip et al. |
| 6,846,841 B2 | 1/2005 | Hunter et al. |
| 6,849,085 B2 | 2/2005 | Marton |
| 6,849,089 B2 | 2/2005 | Stoll |
| 6,852,122 B2 | 2/2005 | Rush |
| 6,858,221 B2 * | 2/2005 | Sirhan et al. ............ 424/423 |
| 6,861,088 B2 * | 3/2005 | Weber et al. ............ 427/2.24 |
| 6,861,729 B2 | 3/2005 | Kozaki et al. |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,896,697 B1 | 5/2005 | Yip et al. |
| 6,899,914 B2 | 5/2005 | Schaldach et al. |
| 6,904,658 B2 | 6/2005 | Hines |
| 6,908,622 B2 | 6/2005 | Barry et al. |
| 6,908,624 B2 * | 6/2005 | Hossainy et al. ............ 424/424 |
| 6,913,617 B1 | 7/2005 | Reiss |
| 6,915,796 B2 | 7/2005 | Sung |
| 6,918,927 B2 | 7/2005 | Bates et al. |
| 6,918,929 B2 | 7/2005 | Udipi et al. |
| 6,923,829 B2 | 8/2005 | Boyle et al. |
| 6,924,004 B2 | 8/2005 | Rao et al. |
| 6,932,930 B2 | 8/2005 | DeSimone et al. |
| 6,936,066 B2 | 8/2005 | Palmaz et al. |
| 6,939,320 B2 | 9/2005 | Lennox |
| 6,951,053 B2 | 10/2005 | Padilla et al. |
| 6,953,560 B1 | 10/2005 | Castro et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,971,813 B2 | 12/2005 | Shekalim et al. |
| 6,973,718 B2 | 12/2005 | Sheppard, Jr. et al. |
| 6,979,346 B1 | 12/2005 | Hossainy et al. |
| 6,979,348 B2 | 12/2005 | Sundar |
| 6,984,404 B1 | 1/2006 | Talton et al. |
| 6,991,804 B2 | 1/2006 | Helmus et al. |
| 7,001,421 B2 | 2/2006 | Cheng et al. |
| 7,011,680 B2 | 3/2006 | Alt |
| 7,014,654 B2 | 3/2006 | Welsh et al. |
| 7,018,408 B2 | 3/2006 | Bailey et al. |
| 7,041,130 B2 | 5/2006 | Santini, Jr. et al. |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,056,591 B1 | 6/2006 | Pacetti et al. |
| 7,060,051 B2 | 6/2006 | Palasis |
| 7,063,748 B2 | 6/2006 | Talton |
| 7,066,234 B2 | 6/2006 | Sawitowski |
| 7,077,859 B2 | 7/2006 | Sirhan et al. |
| 7,078,108 B2 | 7/2006 | Zhang et al. |
| 7,083,642 B2 | 8/2006 | Sirhan et al. |
| 7,087,661 B1 | 8/2006 | Alberte et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,144,840 B2 | 12/2006 | Yeung et al. |
| 7,153,411 B2 | 12/2006 | Larson et al. |
| 7,160,592 B2 | 1/2007 | Rypacek et al. |
| 7,163,715 B1 | 1/2007 | Kramer |
| 7,169,177 B2 | 1/2007 | Obara |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,010 B2 | 4/2007 | Shanley et al. |
| 7,208,011 B2 | 4/2007 | Shanley et al. |
| 7,208,172 B2 | 4/2007 | Birdsall et al. |
| 7,208,190 B2 | 4/2007 | Verlee et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,244,272 B2 | 7/2007 | Dubson et al. |
| 7,247,166 B2 | 7/2007 | Pienknagura |
| 7,247,338 B2 | 7/2007 | Pui et al. |
| 7,261,735 B2 | 8/2007 | Llanos et al. |
| 7,261,752 B2 | 8/2007 | Sung |
| 7,273,493 B2 | 9/2007 | Ledergerber |
| 7,294,409 B2 | 11/2007 | Lye et al. |
| 7,311,727 B2 * | 12/2007 | Mazumder et al. .......... 623/1.44 |
| 7,344,563 B2 | 3/2008 | Vallana et al. |
| 7,368,065 B2 | 5/2008 | Yang et al. |
| 7,393,589 B2 | 7/2008 | Aharonov et al. |
| 7,396,538 B2 | 7/2008 | Granada et al. |
| 7,402,173 B2 | 7/2008 | Scheuermann et al. |
| 7,416,558 B2 | 8/2008 | Yip et al. |
| 7,435,256 B2 | 10/2008 | Stenzel |
| 7,482,034 B2 | 1/2009 | Boulais |
| 7,494,950 B2 | 2/2009 | Armitage et al. |
| 7,497,876 B2 | 3/2009 | Tuke et al. |
| 7,547,445 B2 | 6/2009 | Chudzik et al. |
| 7,563,324 B1 | 7/2009 | Chen et al. |
| 7,575,593 B2 | 8/2009 | Rea et al. |
| 7,575,632 B2 | 8/2009 | Sundar |
| 7,601,382 B2 | 10/2009 | Weber et al. |
| 7,635,515 B1 | 12/2009 | Sherman |
| 7,638,156 B1 | 12/2009 | Hossainy et al. |
| 7,643,885 B2 | 1/2010 | Maschke |
| 7,691,461 B1 | 4/2010 | Prabhu |
| 7,713,297 B2 * | 5/2010 | Alt ............................. 623/1.39 |
| 7,727,275 B2 | 6/2010 | Betts et al. |
| 7,749,264 B2 | 7/2010 | Gregorich et al. |
| 7,758,636 B2 | 7/2010 | Shanley et al. |
| 7,771,773 B2 | 8/2010 | Namavar |
| 7,785,653 B2 | 8/2010 | Shanley et al. |
| 7,837,726 B2 * | 11/2010 | Von Oepen et al. .......... 623/1.44 |
| 7,862,835 B2 * | 1/2011 | Warner et al. ................. 424/501 |
| 7,901,452 B2 | 3/2011 | Gale et al. |
| 7,914,809 B2 | 3/2011 | Atanasoska et al. |
| 7,922,756 B2 | 4/2011 | Lenz et al. |
| 7,931,683 B2 * | 4/2011 | Weber et al. ................ 623/1.42 |
| 7,981,441 B2 | 7/2011 | Pantelidis et al. |
| 8,029,816 B2 | 10/2011 | Hossainy et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0014717 A1 | 8/2001 | Hossainy et al. |
| 2001/0014821 A1 | 8/2001 | Juman et al. |
| 2001/0027299 A1 | 10/2001 | Yang et al. |
| 2001/0029660 A1 | 10/2001 | Johnson |
| 2001/0032011 A1 | 10/2001 | Stanford |
| 2001/0032013 A1 | 10/2001 | Marton |
| 2001/0044651 A1 | 11/2001 | Steinke et al. |
| 2002/0000175 A1 | 1/2002 | Hintermaier et al. |
| 2002/0004060 A1 | 1/2002 | Heublein et al. |
| 2002/0007102 A1 | 1/2002 | Salmon et al. |
| 2002/0007209 A1 | 1/2002 | Scheerder et al. |
| 2002/0009604 A1 | 1/2002 | Zamora et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0038146 A1 | 3/2002 | Harry |
| 2002/0042039 A1 | 4/2002 | Kim et al. |
| 2002/0051730 A1 | 5/2002 | Bodnar et al. |
| 2002/0051846 A1 | 5/2002 | Kirkpatrick et al. |
| 2002/0052288 A1 | 5/2002 | Krell et al. |
| 2002/0065553 A1 | 5/2002 | Weber |
| 2002/0072734 A1 | 6/2002 | Liedtke |
| 2002/0077520 A1 | 6/2002 | Segal et al. |
| 2002/0077693 A1 | 6/2002 | Barclay et al. |
| 2002/0087123 A1 | 7/2002 | Hossainy et al. |
| 2002/0091375 A1 | 7/2002 | Sahatjian et al. |
| 2002/0095871 A1 | 7/2002 | McArdle et al. |
| 2002/0098278 A1 | 7/2002 | Bates et al. |

| | | | | | |
|---|---|---|---|---|---|
| 2002/0099359 A1 | 7/2002 | Santini, Jr. et al. | 2003/0153901 A1 | 8/2003 | Herweck et al. |
| 2002/0099438 A1 | 7/2002 | Furst | 2003/0153971 A1 | 8/2003 | Chandrasekaran |
| 2002/0103527 A1 | 8/2002 | Kocur et al. | 2003/0158598 A1 | 8/2003 | Ashton et al. |
| 2002/0103528 A1 | 8/2002 | Schaldach et al. | 2003/0167878 A1 | 9/2003 | Al-Salim et al. |
| 2002/0104599 A1 | 8/2002 | Tillotson et al. | 2003/0170605 A1 | 9/2003 | Long et al. |
| 2002/0121497 A1 | 9/2002 | Tomonto | 2003/0181975 A1 | 9/2003 | Ishii et al. |
| 2002/0123801 A1 | 9/2002 | Pacetti et al. | 2003/0185895 A1 | 10/2003 | Lanphere et al. |
| 2002/0133222 A1 | 9/2002 | Das | 2003/0185964 A1 | 10/2003 | Weber et al. |
| 2002/0133225 A1 | 9/2002 | Gordon | 2003/0190406 A1 | 10/2003 | Hossainy et al. |
| 2002/0138100 A1 | 9/2002 | Stoll et al. | 2003/0195613 A1 | 10/2003 | Curcio et al. |
| 2002/0138136 A1 | 9/2002 | Chandresekaran et al. | 2003/0203991 A1 | 10/2003 | Schottman et al. |
| 2002/0140137 A1 | 10/2002 | Sapieszko et al. | 2003/0204168 A1 | 10/2003 | Bosma et al. |
| 2002/0142579 A1 | 10/2002 | Vincent et al. | 2003/0208256 A1 | 11/2003 | DiMatteo et al. |
| 2002/0144757 A1 | 10/2002 | Craig et al. | 2003/0211135 A1 | 11/2003 | Greenhalgh et al. |
| 2002/0155212 A1 | 10/2002 | Hossainy | 2003/0216803 A1 | 11/2003 | Ledergerber |
| 2002/0165265 A1 | 11/2002 | Hunter et al. | 2003/0216806 A1 | 11/2003 | Togawa et al. |
| 2002/0165600 A1 | 11/2002 | Banas et al. | 2003/0219562 A1 | 11/2003 | Rypacek et al. |
| 2002/0165607 A1 | 11/2002 | Alt | 2003/0225450 A1 | 12/2003 | Shulze et al. |
| 2002/0167118 A1 | 11/2002 | Billiet et al. | 2003/0236323 A1 | 12/2003 | Ratner et al. |
| 2002/0168466 A1 | 11/2002 | Tapphorn et al. | 2003/0236514 A1 | 12/2003 | Schwarz |
| 2002/0169493 A1 | 11/2002 | Widenhouse et al. | 2004/0000540 A1 | 1/2004 | Soboyejo et al. |
| 2002/0178570 A1 | 12/2002 | Sogard et al. | 2004/0002755 A1 | 1/2004 | Fischell et al. |
| 2002/0182241 A1 | 12/2002 | Borenstein et al. | 2004/0006382 A1 | 1/2004 | Sohier |
| 2002/0183581 A1 | 12/2002 | Yoe et al. | 2004/0013873 A1 | 1/2004 | Wendorff et al. |
| 2002/0183682 A1 | 12/2002 | Darvish et al. | 2004/0016651 A1 | 1/2004 | Windler |
| 2002/0187260 A1 | 12/2002 | Sheppard, Jr. et al. | 2004/0018296 A1 | 1/2004 | Castro et al. |
| 2002/0193336 A1 | 12/2002 | Elkins et al. | 2004/0019376 A1 | 1/2004 | Alt |
| 2002/0193869 A1 | 12/2002 | Dang | 2004/0022824 A1 | 2/2004 | Li et al. |
| 2002/0197178 A1 | 12/2002 | Yan | 2004/0026811 A1 | 2/2004 | Murphy et al. |
| 2002/0198601 A1 | 12/2002 | Bales et al. | 2004/0028875 A1 | 2/2004 | Van Rijn et al. |
| 2003/0003160 A1 | 1/2003 | Pugh et al. | 2004/0029303 A1 | 2/2004 | Hart et al. |
| 2003/0003220 A1 | 1/2003 | Zhong et al. | 2004/0029706 A1 | 2/2004 | Barrera et al. |
| 2003/0004563 A1 | 1/2003 | Jackson et al. | 2004/0030218 A1 | 2/2004 | Kocur et al. |
| 2003/0004564 A1 | 1/2003 | Elkins et al. | 2004/0030377 A1 | 2/2004 | Dubson et al. |
| 2003/0006250 A1 | 1/2003 | Tapphorn et al. | 2004/0039438 A1 | 2/2004 | Alt |
| 2003/0009214 A1 | 1/2003 | Shanley | 2004/0039441 A1 | 2/2004 | Rowland et al. |
| 2003/0009233 A1 | 1/2003 | Blinn et al. | 2004/0044397 A1 | 3/2004 | Stinson |
| 2003/0018380 A1 | 1/2003 | Craig et al. | 2004/0047980 A1 | 3/2004 | Pacetti et al. |
| 2003/0018381 A1 | 1/2003 | Whitcher et al. | 2004/0052861 A1 | 3/2004 | Hatcher et al. |
| 2003/0021820 A1 | 1/2003 | Ahola et al. | 2004/0058858 A1 | 3/2004 | Hu |
| 2003/0023300 A1 | 1/2003 | Bailey et al. | 2004/0059290 A1 | 3/2004 | Palasis |
| 2003/0028242 A1 | 2/2003 | Vallana et al. | 2004/0059407 A1 | 3/2004 | Escamilla et al. |
| 2003/0028243 A1 | 2/2003 | Bates et al. | 2004/0059409 A1 | 3/2004 | Stenzel |
| 2003/0032892 A1 | 2/2003 | Erlach et al. | 2004/0067301 A1 | 4/2004 | Ding |
| 2003/0033007 A1 | 2/2003 | Sirhan et al. | 2004/0071861 A1 | 4/2004 | Mandrusov et al. |
| 2003/0044446 A1 | 3/2003 | Moro et al. | 2004/0073284 A1 | 4/2004 | Bates et al. |
| 2003/0047028 A1 | 3/2003 | Kunitake et al. | 2004/0073298 A1 | 4/2004 | Hossainy |
| 2003/0047505 A1 | 3/2003 | Grimes et al. | 2004/0078071 A1 | 4/2004 | Escamilla et al. |
| 2003/0050687 A1 | 3/2003 | Schwade et al. | 2004/0088038 A1 | 5/2004 | Dehnad et al. |
| 2003/0059640 A1 | 3/2003 | Marton et al. | 2004/0088041 A1 | 5/2004 | Stanford |
| 2003/0060871 A1 | 3/2003 | Hill et al. | 2004/0092653 A1 | 5/2004 | Ruberti et al. |
| 2003/0060873 A1 | 3/2003 | Gertner et al. | 2004/0093071 A1 | 5/2004 | Jang |
| 2003/0060877 A1 | 3/2003 | Falotico et al. | 2004/0093076 A1 | 5/2004 | White et al. |
| 2003/0064095 A1 | 4/2003 | Martin et al. | 2004/0098089 A1 | 5/2004 | Weber |
| 2003/0069631 A1 | 4/2003 | Stoll | 2004/0098119 A1 | 5/2004 | Wang |
| 2003/0074053 A1 | 4/2003 | Palmaz et al. | 2004/0102758 A1 | 5/2004 | Davila et al. |
| 2003/0074075 A1 | 4/2003 | Thomas, Jr. et al. | 2004/0106984 A1 | 6/2004 | Stinson |
| 2003/0074081 A1 | 4/2003 | Ayers | 2004/0106985 A1 | 6/2004 | Jang |
| 2003/0077200 A1 | 4/2003 | Craig et al. | 2004/0106987 A1 | 6/2004 | Palasis et al. |
| 2003/0083614 A1 | 5/2003 | Eisert | 2004/0106994 A1 | 6/2004 | De Maeztus Martinez et al. |
| 2003/0083646 A1 | 5/2003 | Sirhan et al. | 2004/0111150 A1 | 6/2004 | Berg et al. |
| 2003/0083731 A1 | 5/2003 | Kramer et al. | 2004/0116999 A1 | 6/2004 | Ledergerber |
| 2003/0087024 A1 | 5/2003 | Flanagan | 2004/0117005 A1 | 6/2004 | Nagarada Gadde et al. |
| 2003/0088307 A1 | 5/2003 | Shulze et al. | 2004/0117008 A1* | 6/2004 | Wnendt et al. ............... 623/1.46 |
| 2003/0088312 A1 | 5/2003 | Kopia et al. | 2004/0122504 A1 | 6/2004 | Hogendijk |
| 2003/0100865 A1 | 5/2003 | Santini, Jr. et al. | 2004/0126566 A1 | 7/2004 | Axen et al. |
| 2003/0104028 A1 | 6/2003 | Hossainy et al. | 2004/0133270 A1 | 7/2004 | Grandt |
| 2003/0105511 A1 | 6/2003 | Welsh et al. | 2004/0134886 A1 | 7/2004 | Wagner et al. |
| 2003/0108659 A1 | 6/2003 | Bales et al. | 2004/0142014 A1 | 7/2004 | Litvack et al. |
| 2003/0114917 A1 | 6/2003 | Holloway et al. | 2004/0143317 A1 | 7/2004 | Stinson et al. |
| 2003/0114921 A1 | 6/2003 | Yoon | 2004/0143321 A1 | 7/2004 | Litvack et al. |
| 2003/0118649 A1 | 6/2003 | Gao et al. | 2004/0148010 A1 | 7/2004 | Rush |
| 2003/0125803 A1 | 7/2003 | Vallana et al. | 2004/0148015 A1 | 7/2004 | Lye et al. |
| 2003/0130206 A1 | 7/2003 | Koziak et al. | 2004/0158308 A1 | 8/2004 | Hogendijk et al. |
| 2003/0130718 A1 | 7/2003 | Palmas et al. | 2004/0167572 A1 | 8/2004 | Roth et al. |
| 2003/0138645 A1 | 7/2003 | Gleason et al. | 2004/0167612 A1 | 8/2004 | Grignani et al. |
| 2003/0139799 A1 | 7/2003 | Ley et al. | 2004/0171978 A1 | 9/2004 | Shalaby |
| 2003/0144728 A1 | 7/2003 | Scheuermann et al. | 2004/0172124 A1 | 9/2004 | Vallana et al. |
| 2003/0150380 A1 | 8/2003 | Yoe | 2004/0178523 A1 | 9/2004 | Kim et al. |

| | | | | | | |
|---|---|---|---|---|---|---|
| 2004/0181252 A1 | 9/2004 | Boyle et al. | | 2005/0192657 A1 | 9/2005 | Colen et al. |
| 2004/0181275 A1 | 9/2004 | Noble et al. | | 2005/0192664 A1 | 9/2005 | Eisert |
| 2004/0181276 A1 | 9/2004 | Brown et al. | | 2005/0196424 A1 | 9/2005 | Chappa |
| 2004/0185168 A1 | 9/2004 | Weber et al. | | 2005/0196518 A1 | 9/2005 | Stenzel |
| 2004/0191293 A1 | 9/2004 | Claude | | 2005/0197687 A1 | 9/2005 | Molaei et al. |
| 2004/0191404 A1 | 9/2004 | Hossainy et al. | | 2005/0197689 A1 | 9/2005 | Molaei |
| 2004/0202692 A1 | 10/2004 | Shanley et al. | | 2005/0203606 A1 | 9/2005 | Vancamp |
| 2004/0204750 A1 | 10/2004 | Dinh | | 2005/0208098 A1 | 9/2005 | Castro et al. |
| 2004/0211362 A1 | 10/2004 | Castro et al. | | 2005/0208100 A1 | 9/2005 | Weber et al. |
| 2004/0249450 A1* | 12/2004 | Ishii .............................. 623/1.44 | | 2005/0209681 A1 | 9/2005 | Curcio et al. |
| 2004/0254635 A1* | 12/2004 | Shanley et al. ............... 623/1.17 | | 2005/0211680 A1 | 9/2005 | Li et al. |
| 2005/0002865 A1 | 1/2005 | Klaveness et al. | | 2005/0214951 A1 | 9/2005 | Nahm et al. |
| 2005/0004663 A1 | 1/2005 | Llanos et al. | | 2005/0216074 A1 | 9/2005 | Sahatjian et al. |
| 2005/0010275 A1 | 1/2005 | Sahatjian et al. | | 2005/0216075 A1 | 9/2005 | Wang et al. |
| 2005/0015142 A1 | 1/2005 | Austin et al. | | 2005/0220853 A1 | 10/2005 | Dao et al. |
| 2005/0019265 A1 | 1/2005 | Hammer et al. | | 2005/0221072 A1 | 10/2005 | Dubrow et al. |
| 2005/0019371 A1 | 1/2005 | Anderson et al. | | 2005/0228477 A1 | 10/2005 | Grainger et al. |
| 2005/0020614 A1 | 1/2005 | Prescott et al. | | 2005/0228491 A1 | 10/2005 | Snyder et al. |
| 2005/0021127 A1 | 1/2005 | Kawula | | 2005/0232968 A1 | 10/2005 | Palmaz et al. |
| 2005/0021128 A1 | 1/2005 | Nakahama et al. | | 2005/0233965 A1 | 10/2005 | Schwartz et al. |
| 2005/0027350 A1 | 2/2005 | Momma et al. | | 2005/0244459 A1 | 11/2005 | DeWitt et al. |
| 2005/0033411 A1 | 2/2005 | Wu et al. | | 2005/0251245 A1 | 11/2005 | Sieradzki et al. |
| 2005/0033412 A1 | 2/2005 | Wu et al. | | 2005/0251249 A1 | 11/2005 | Sahatjian et al. |
| 2005/0033417 A1 | 2/2005 | Borges et al. | | 2005/0255707 A1 | 11/2005 | Hart et al. |
| 2005/0037047 A1 | 2/2005 | Song | | 2005/0261760 A1 | 11/2005 | Weber |
| 2005/0038498 A1 | 2/2005 | Dubrow et al. | | 2005/0266039 A1 | 12/2005 | Weber |
| 2005/0042288 A1 | 2/2005 | Koblish et al. | | 2005/0266040 A1 | 12/2005 | Gerberding |
| 2005/0055080 A1 | 3/2005 | Istephanous et al. | | 2005/0267561 A1 | 12/2005 | Jones et al. |
| 2005/0055085 A1 | 3/2005 | Rivron et al. | | 2005/0271703 A1 | 12/2005 | Anderson et al. |
| 2005/0060020 A1 | 3/2005 | Jenson | | 2005/0271706 A1 | 12/2005 | Anderson et al. |
| 2005/0060021 A1 | 3/2005 | O'Brien et al. | | 2005/0276837 A1 | 12/2005 | Anderson et al. |
| 2005/0069630 A1 | 3/2005 | Fox et al. | | 2005/0278016 A1 | 12/2005 | Welsh et al. |
| 2005/0070989 A1 | 3/2005 | Lye et al. | | 2005/0278021 A1 | 12/2005 | Bates et al. |
| 2005/0070990 A1 | 3/2005 | Stinson | | 2005/0281863 A1 | 12/2005 | Anderson et al. |
| 2005/0070996 A1 | 3/2005 | Dinh et al. | | 2005/0285073 A1 | 12/2005 | Singh et al. |
| 2005/0072544 A1 | 4/2005 | Palmaz et al. | | 2005/0287188 A1 | 12/2005 | Anderson et al. |
| 2005/0074479 A1 | 4/2005 | Weber et al. | | 2006/0013850 A1 | 1/2006 | Domb |
| 2005/0074545 A1 | 4/2005 | Thomas | | 2006/0015175 A1 | 1/2006 | Palmaz et al. |
| 2005/0077305 A1 | 4/2005 | Guevara | | 2006/0015361 A1 | 1/2006 | Sattler et al. |
| 2005/0079199 A1 | 4/2005 | Heruth et al. | | 2006/0020742 A1 | 1/2006 | Au et al. |
| 2005/0079201 A1 | 4/2005 | Rathenow et al. | | 2006/0025848 A1 | 2/2006 | Weber et al. |
| 2005/0079356 A1 | 4/2005 | Rathenow et al. | | 2006/0034884 A1 | 2/2006 | Stenzel |
| 2005/0087520 A1 | 4/2005 | Wang et al. | | 2006/0035026 A1 | 2/2006 | Atanassoska et al. |
| 2005/0092615 A1 | 5/2005 | Birdsall et al. | | 2006/0038027 A1 | 2/2006 | O'Connor et al. |
| 2005/0096731 A1 | 5/2005 | Looi et al. | | 2006/0051397 A1 | 3/2006 | Maier et al. |
| 2005/0100577 A1 | 5/2005 | Parker et al. | | 2006/0052744 A1 | 3/2006 | Weber |
| 2005/0100609 A1 | 5/2005 | Claude | | 2006/0052863 A1 | 3/2006 | Harder et al. |
| 2005/0102025 A1 | 5/2005 | Laroche et al. | | 2006/0052864 A1 | 3/2006 | Harder et al. |
| 2005/0106212 A1 | 5/2005 | Gertner et al. | | 2006/0062820 A1 | 3/2006 | Gertner et al. |
| 2005/0107869 A1 | 5/2005 | Sirhan et al. | | 2006/0069427 A1 | 3/2006 | Savage et al. |
| 2005/0107870 A1 | 5/2005 | Wang et al. | | 2006/0075044 A1 | 4/2006 | Fox et al. |
| 2005/0110214 A1 | 5/2005 | Shank et al. | | 2006/0075092 A1 | 4/2006 | Kidokoro |
| 2005/0113798 A1 | 5/2005 | Slater et al. | | 2006/0079863 A1 | 4/2006 | Burgmeier et al. |
| 2005/0113936 A1 | 5/2005 | Brustad et al. | | 2006/0085062 A1 | 4/2006 | Lee et al. |
| 2005/0118229 A1 | 6/2005 | Boiarski | | 2006/0085065 A1 | 4/2006 | Krause et al. |
| 2005/0119723 A1 | 6/2005 | Peacock | | 2006/0088561 A1 | 4/2006 | Eini et al. |
| 2005/0129727 A1 | 6/2005 | Weber et al. | | 2006/0088566 A1 | 4/2006 | Parsonage et al. |
| 2005/0131509 A1 | 6/2005 | Atanassoska et al. | | 2006/0088567 A1 | 4/2006 | Warner et al. |
| 2005/0131521 A1 | 6/2005 | Marton | | 2006/0088666 A1 | 4/2006 | Kobrin et al. |
| 2005/0131522 A1 | 6/2005 | Stinson et al. | | 2006/0093643 A1 | 5/2006 | Stenzel |
| 2005/0131532 A1 | 6/2005 | Sirhan et al. | | 2006/0093646 A1 | 5/2006 | Cima et al. |
| 2005/0136090 A1 | 6/2005 | Falotico et al. | | 2006/0095123 A1 | 5/2006 | Flanagan |
| 2005/0137677 A1 | 6/2005 | Rush | | 2006/0100696 A1 | 5/2006 | Atanasoska et al. |
| 2005/0137679 A1 | 6/2005 | Changelian et al. | | 2006/0115512 A1 | 6/2006 | Peacock et al. |
| 2005/0137684 A1 | 6/2005 | Changelian et al. | | 2006/0121080 A1 | 6/2006 | Lye et al. |
| 2005/0149102 A1 | 7/2005 | Radisch et al. | | 2006/0122694 A1 | 6/2006 | Stinson et al. |
| 2005/0149170 A1 | 7/2005 | Tassel et al. | | 2006/0125144 A1 | 6/2006 | Weber et al. |
| 2005/0159804 A1 | 7/2005 | Lad et al. | | 2006/0127442 A1 | 6/2006 | Helmus |
| 2005/0159805 A1 | 7/2005 | Weber et al. | | 2006/0127443 A1 | 6/2006 | Helmus |
| 2005/0160600 A1 | 7/2005 | Bien et al. | | 2006/0129215 A1 | 6/2006 | Helmus et al. |
| 2005/0163954 A1 | 7/2005 | Shaw | | 2006/0129225 A1 | 6/2006 | Kopia et al. |
| 2005/0165467 A1 | 7/2005 | Hunter et al. | | 2006/0136048 A1 | 6/2006 | Pacetti et al. |
| 2005/0165468 A1 | 7/2005 | Marton | | 2006/0140867 A1* | 6/2006 | Helfer et al. .................. 424/9.32 |
| 2005/0165476 A1 | 7/2005 | Furst et al. | | 2006/0141156 A1 | 6/2006 | Viel et al. |
| 2005/0171595 A1 | 8/2005 | Feldman et al. | | 2006/0142853 A1 | 6/2006 | Wang et al. |
| 2005/0180919 A1 | 8/2005 | Tedeschi | | 2006/0149365 A1 | 7/2006 | Fifer et al. |
| 2005/0182478 A1 | 8/2005 | Holman et al. | | 2006/0153729 A1 | 7/2006 | Stinson et al. |
| 2005/0186250 A1 | 8/2005 | Gertner et al. | | 2006/0155361 A1 | 7/2006 | Schomig et al. |
| 2005/0187608 A1 | 8/2005 | O'Hara | | 2006/0167543 A1 | 7/2006 | Bailey et al. |

| Publication No. | Date | Inventor(s) |
|---|---|---|
| 2006/0171985 A1 | 8/2006 | Richard et al. |
| 2006/0171990 A1* | 8/2006 | Asgari ......................... 424/426 |
| 2006/0178727 A1 | 8/2006 | Richter |
| 2006/0184235 A1 | 8/2006 | Rivron et al. |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0193890 A1 | 8/2006 | Owens et al. |
| 2006/0199876 A1 | 9/2006 | Troczynski et al. |
| 2006/0200229 A1 | 9/2006 | Burgermeister et al. |
| 2006/0200231 A1 | 9/2006 | O'Brien et al. |
| 2006/0210595 A1 | 9/2006 | Singhvi et al. |
| 2006/0212109 A1 | 9/2006 | Sirhan et al. |
| 2006/0222679 A1 | 10/2006 | Shanley et al. |
| 2006/0222844 A1 | 10/2006 | Stinson |
| 2006/0224234 A1 | 10/2006 | Jayaraman |
| 2006/0229711 A1 | 10/2006 | Yan et al. |
| 2006/0229713 A1 | 10/2006 | Shanley et al. |
| 2006/0229715 A1 | 10/2006 | Istephanous et al. |
| 2006/0230476 A1 | 10/2006 | Atanasoska et al. |
| 2006/0233941 A1 | 10/2006 | Olson |
| 2006/0251701 A1 | 11/2006 | Lynn et al. |
| 2006/0263512 A1 | 11/2006 | Glocker |
| 2006/0263515 A1 | 11/2006 | Rieck et al. |
| 2006/0264138 A1 | 11/2006 | Sowinski et al. |
| 2006/0271169 A1 | 11/2006 | Lye et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1 | 12/2006 | Lye et al. |
| 2006/0276885 A1 | 12/2006 | Lye et al. |
| 2006/0276910 A1 | 12/2006 | Weber |
| 2006/0280770 A1 | 12/2006 | Hossainy et al. |
| 2006/0292388 A1 | 12/2006 | Palumbo et al. |
| 2007/0003589 A1 | 1/2007 | Astafieva et al. |
| 2007/0003817 A1 | 1/2007 | Umeda et al. |
| 2007/0032858 A1 | 2/2007 | Santos et al. |
| 2007/0032864 A1 | 2/2007 | Furst et al. |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0048452 A1 | 3/2007 | Feng et al. |
| 2007/0052497 A1 | 3/2007 | Tada |
| 2007/0055349 A1 | 3/2007 | Santos et al. |
| 2007/0055354 A1 | 3/2007 | Santos et al. |
| 2007/0059435 A1 | 3/2007 | Santos et al. |
| 2007/0065418 A1 | 3/2007 | Vallana et al. |
| 2007/0071789 A1 | 3/2007 | Pantelidis et al. |
| 2007/0072978 A1 | 3/2007 | Zoromski et al. |
| 2007/0073385 A1 | 3/2007 | Schaeffer et al. |
| 2007/0073390 A1 | 3/2007 | Lee |
| 2007/0106347 A1 | 5/2007 | Lin |
| 2007/0110888 A1 | 5/2007 | Radhakrishnan et al. |
| 2007/0112421 A1 | 5/2007 | O'Brien |
| 2007/0123973 A1 | 5/2007 | Roth et al. |
| 2007/0128245 A1 | 6/2007 | Rosenberg et al. |
| 2007/0129789 A1 | 6/2007 | Cottone et al. |
| 2007/0134288 A1 | 6/2007 | Parsonage et al. |
| 2007/0135908 A1 | 6/2007 | Zhao |
| 2007/0148251 A1 | 6/2007 | Hossainy et al. |
| 2007/0151093 A1 | 7/2007 | Curcio et al. |
| 2007/0154513 A1 | 7/2007 | Atanasoska et al. |
| 2007/0156231 A1 | 7/2007 | Weber |
| 2007/0173923 A1 | 7/2007 | Savage et al. |
| 2007/0181433 A1 | 8/2007 | Birdsall et al. |
| 2007/0190104 A1 | 8/2007 | Kamath et al. |
| 2007/0191923 A1 | 8/2007 | Weber et al. |
| 2007/0191928 A1 | 8/2007 | Rolando et al. |
| 2007/0191931 A1 | 8/2007 | Weber et al. |
| 2007/0191943 A1 | 8/2007 | Shrivastava et al. |
| 2007/0198081 A1 | 8/2007 | Castro et al. |
| 2007/0202466 A1 | 8/2007 | Schwarz et al. |
| 2007/0207186 A1 | 9/2007 | Scanlon et al. |
| 2007/0208412 A1 | 9/2007 | Elmaleh |
| 2007/0212547 A1 | 9/2007 | Fredrickson et al. |
| 2007/0213827 A1 | 9/2007 | Arramon |
| 2007/0219626 A1 | 9/2007 | Rolando et al. |
| 2007/0219642 A1* | 9/2007 | Richter ......................... 623/23.7 |
| 2007/0224116 A1 | 9/2007 | Chandrasekaran et al. |
| 2007/0224224 A1 | 9/2007 | Cordeira Da Silva et al. |
| 2007/0224235 A1 | 9/2007 | Tenney et al. |
| 2007/0224244 A1 | 9/2007 | Weber et al. |
| 2007/0244569 A1 | 10/2007 | Weber et al. |
| 2007/0254091 A1 | 11/2007 | Fredrickson et al. |
| 2007/0255392 A1 | 11/2007 | Johnson |
| 2007/0264303 A1 | 11/2007 | Atanasoska et al. |
| 2007/0269480 A1 | 11/2007 | Richard et al. |
| 2007/0299509 A1 | 12/2007 | Ding |
| 2008/0003251 A1 | 1/2008 | Zhou |
| 2008/0004691 A1 | 1/2008 | Weber et al. |
| 2008/0008654 A1 | 1/2008 | Clarke et al. |
| 2008/0038146 A1 | 2/2008 | Wachter et al. |
| 2008/0050413 A1 | 2/2008 | Horvers et al. |
| 2008/0050415 A1 | 2/2008 | Atanasoska et al. |
| 2008/0051881 A1 | 2/2008 | Feng et al. |
| 2008/0057103 A1 | 3/2008 | Roorda |
| 2008/0058921 A1 | 3/2008 | Lindquist |
| 2008/0069854 A1 | 3/2008 | Xiao et al. |
| 2008/0071348 A1* | 3/2008 | Boismier et al. ............. 623/1.15 |
| 2008/0071349 A1 | 3/2008 | Atanasoska et al. |
| 2008/0071350 A1 | 3/2008 | Stinson |
| 2008/0071351 A1 | 3/2008 | Flanagan et al. |
| 2008/0071352 A1 | 3/2008 | Weber et al. |
| 2008/0071353 A1 | 3/2008 | Weber et al. |
| 2008/0071355 A1 | 3/2008 | Weber et al. |
| 2008/0071358 A1 | 3/2008 | Weber et al. |
| 2008/0086198 A1* | 4/2008 | Owens et al. ................. 623/1.39 |
| 2008/0086199 A1 | 4/2008 | Dave et al. |
| 2008/0086201 A1 | 4/2008 | Weber et al. |
| 2008/0097577 A1 | 4/2008 | Atanasoska et al. |
| 2008/0107890 A1 | 5/2008 | Bureau et al. |
| 2008/0124374 A1 | 5/2008 | Xiao et al. |
| 2008/0140186 A1 | 6/2008 | Grignani et al. |
| 2008/0145400 A1 | 6/2008 | Weber et al. |
| 2008/0147177 A1 | 6/2008 | Scheuermann et al. |
| 2008/0150259 A1 | 6/2008 | Nielson et al. |
| 2008/0152929 A1 | 6/2008 | Zhao |
| 2008/0160259 A1* | 7/2008 | Nielson et al. ................. 428/148 |
| 2008/0171929 A1 | 7/2008 | Katims |
| 2008/0183278 A1 | 7/2008 | Atanasoska et al. |
| 2008/0188836 A1 | 8/2008 | Weber et al. |
| 2008/0241218 A1 | 10/2008 | McMorrow et al. |
| 2008/0243231 A1 | 10/2008 | Flanagan et al. |
| 2008/0243240 A1 | 10/2008 | Doty et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255657 A1 | 10/2008 | Gregorich et al. |
| 2008/0262607 A1 | 10/2008 | Fricke |
| 2008/0275543 A1 | 11/2008 | Lenz et al. |
| 2008/0288048 A1 | 11/2008 | Rolando et al. |
| 2008/0290467 A1 | 11/2008 | Shue et al. |
| 2008/0294236 A1 | 11/2008 | Anand et al. |
| 2008/0294246 A1 | 11/2008 | Scheuermann et al. |
| 2008/0306584 A1 | 12/2008 | Kramer-Brown |
| 2009/0012603 A1 | 1/2009 | Xu et al. |
| 2009/0018639 A1 | 1/2009 | Kuehling |
| 2009/0018642 A1 | 1/2009 | Benco |
| 2009/0018644 A1 | 1/2009 | Weber et al. |
| 2009/0018647 A1 | 1/2009 | Benco et al. |
| 2009/0028785 A1 | 1/2009 | Clarke |
| 2009/0030504 A1 | 1/2009 | Weber et al. |
| 2009/0076588 A1 | 3/2009 | Weber |
| 2009/0076595 A1 | 3/2009 | Lindquist et al. |
| 2009/0081450 A1 | 3/2009 | Ascher et al. |
| 2009/0112310 A1 | 4/2009 | Zhang |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118820 A1 | 5/2009 | Gregorich et al. |
| 2009/0118821 A1* | 5/2009 | Scheuermann et al. ...... 623/1.49 |
| 2009/0118822 A1 | 5/2009 | Holman et al. |
| 2009/0118823 A1 | 5/2009 | Atanasoska et al. |

| | | | | | | |
|---|---|---|---|---|---|---|
| 2009/0123517 A1 | 5/2009 | Flanagan et al. | | CA | 2235031 | 10/1998 |
| 2009/0123521 A1 | 5/2009 | Weber et al. | | CA | 2238837 | 2/1999 |
| 2009/0138077 A1 | 5/2009 | Weber et al. | | CA | 2340652 | 3/2000 |
| 2009/0149942 A1 | 6/2009 | Edelman et al. | | CA | 2392006 | 5/2001 |
| 2009/0157165 A1* | 6/2009 | Miller et al. | 623/1.15 | CA | 2337565 | 8/2001 |
| 2009/0157166 A1 | 6/2009 | Singhal et al. | | CA | 2409862 | 11/2001 |
| 2009/0157172 A1* | 6/2009 | Kokate et al. | 623/1.43 | CA | 2353197 | 1/2002 |
| 2009/0177273 A1* | 7/2009 | Piveteau et al. | 623/1.46 | CA | 2429356 | 8/2002 |
| 2009/0186068 A1 | 7/2009 | Miller et al. | | CA | 2435306 | 8/2002 |
| 2009/0192593 A1 | 7/2009 | Meyer et al. | | CA | 2436241 | 8/2002 |
| 2009/0202610 A1 | 8/2009 | Wilson | | CA | 2438095 | 8/2002 |
| 2009/0208428 A1 | 8/2009 | Hill et al. | | CA | 2460334 | 3/2003 |
| 2009/0220612 A1 | 9/2009 | Perera | | CA | 2425665 | 4/2003 |
| 2009/0259300 A1 | 10/2009 | Dorogy, Jr. et al. | | CA | 2465704 | 4/2003 |
| 2009/0264975 A1 | 10/2009 | Flanagan et al. | | CA | 2464906 | 5/2003 |
| 2009/0281613 A1 | 11/2009 | Atanasoska et al. | | CA | 2468677 | 6/2003 |
| 2009/0287301 A1 | 11/2009 | Weber | | CA | 2469744 | 6/2003 |
| 2009/0306765 A1 | 12/2009 | Weber | | CA | 2484383 | 1/2004 |
| 2009/0317766 A1 | 12/2009 | Heidenau et al. | | CA | 2497602 | 4/2004 |
| 2009/0319032 A1 | 12/2009 | Weber et al. | | CA | 2499976 | 4/2004 |
| 2010/0003904 A1* | 1/2010 | Duescher | 451/259 | CA | 2503625 | 5/2004 |
| 2010/0008970 A1 | 1/2010 | O'Brien et al. | | CA | 2504524 | 5/2004 |
| 2010/0028403 A1 | 2/2010 | Scheuermann et al. | | CA | 2505576 | 5/2004 |
| 2010/0030326 A1 | 2/2010 | Radhakrishnan et al. | | CA | 2513721 | 5/2004 |
| 2010/0042206 A1 | 2/2010 | Yadav et al. | | CA | 2505080 | 6/2004 |
| 2010/0057197 A1 | 3/2010 | Weber et al. | | CA | 2506622 | 6/2004 |
| 2010/0070013 A1* | 3/2010 | Park | 623/1.11 | CA | 2455670 | 7/2004 |
| 2010/0070022 A1 | 3/2010 | Kuehling | | CA | 2508247 | 7/2004 |
| 2010/0070026 A1 | 3/2010 | Ito et al. | | CA | 2467797 | 11/2004 |
| 2010/0130346 A1* | 5/2010 | Laine et al. | 501/105 | CA | 2258898 | 1/2005 |
| 2010/0131050 A1 | 5/2010 | Zhao | 623/1.42 | CA | 2308177 | 1/2005 |
| 2010/0233226 A1* | 9/2010 | Ferain et al. | 424/422 | CA | 2475968 | 1/2005 |
| 2011/0034752 A1* | 2/2011 | Kessler et al. | 600/2 | CA | 2489668 | 6/2005 |
| | | | | CA | 2490170 | 6/2005 |
| FOREIGN PATENT DOCUMENTS | | | | CA | 2458172 | 8/2005 |
| AU | 4825696 | 10/1996 | | CA | 2474367 | 1/2006 |
| AU | 5588896 | 12/1996 | | CA | 2374090 | 5/2007 |
| AU | 5266698 | 6/1998 | | CA | 2282748 | 11/2007 |
| AU | 6663298 | 9/1998 | | CA | 2336650 | 1/2008 |
| AU | 716005 | 2/2000 | | CA | 2304325 | 5/2008 |
| AU | 5686499 | 3/2000 | | CN | 1430491 | 7/2003 |
| AU | 2587100 | 5/2000 | | CN | 1547490 | 11/2004 |
| AU | 2153600 | 6/2000 | | CN | 1575154 | 2/2005 |
| AU | 1616201 | 5/2001 | | CN | 1585627 | 2/2005 |
| AU | 737252 | 8/2001 | | CN | 1669537 | 9/2005 |
| AU | 2317701 | 8/2001 | | DE | 3516411 | 11/1986 |
| AU | 5890401 | 12/2001 | | DE | 3608158 | 9/1987 |
| AU | 3597401 | 6/2002 | | DE | 19916086 | 10/1999 |
| AU | 2002353068 | 3/2003 | | DE | 19855421 | 5/2000 |
| AU | 2002365875 | 6/2003 | | DE | 19916315 | 9/2000 |
| AU | 2003250913 | 1/2004 | | DE | 9422438 | 4/2002 |
| AU | 770395 | 2/2004 | | DE | 1096902 | 5/2002 |
| AU | 2003249017 | 2/2004 | | DE | 10064596 | 6/2002 |
| AU | 2003256499 | 2/2004 | | DE | 10107339 | 9/2002 |
| AU | 771367 | 3/2004 | | DE | 69712063 | 10/2002 |
| AU | 2003271633 | 4/2004 | | DE | 10127011 | 12/2002 |
| AU | 2003272710 | 4/2004 | | DE | 10150995 | 4/2003 |
| AU | 2003285195 | 6/2004 | | DE | 69807634 | 5/2003 |
| AU | 2003287633 | 6/2004 | | DE | 69431457 | 6/2003 |
| AU | 2003290675 | 6/2004 | | DE | 10200387 | 8/2003 |
| AU | 2003290676 | 6/2004 | | DE | 69719161 | 10/2003 |
| AU | 2003291470 | 6/2004 | | DE | 02704283 | 4/2004 |
| AU | 2003295419 | 6/2004 | | DE | 60106962 | 4/2005 |
| AU | 2003295535 | 6/2004 | | DE | 60018318 | 12/2005 |
| AU | 2003295763 | 6/2004 | | DE | 69732439 | 1/2006 |
| AU | 2004202073 | 6/2004 | | DE | 69828798 | 1/2006 |
| AU | 2003300323 | 7/2004 | | DE | 102004044738 | 3/2006 |
| AU | 2004213021 | 9/2004 | | DE | 69830605 | 5/2006 |
| AU | 2003293557 | 1/2005 | | DE | 102005010100 | 9/2006 |
| AU | 780539 | 3/2005 | | DE | 602005001867 | 5/2008 |
| BR | 8701135 | 1/1988 | | DE | 69829015 | 3/2009 |
| BR | 0207321 | 2/2004 | | DK | 127987 | 9/1987 |
| BR | 0016957 | 6/2004 | | DK | 914092 | 8/2002 |
| BR | 0316065 | 9/2005 | | EP | 0222853 | 5/1987 |
| BR | 0316102 | 9/2005 | | EP | 0129147 | 1/1990 |
| CA | 1283505 | 4/1991 | | EP | 0734721 | 10/1996 |
| CA | 2172187 | 10/1996 | | EP | 0650604 | 9/1998 |
| CA | 2178541 | 12/1996 | | EP | 0865762 | 9/1998 |
| CA | 2234787 | 10/1998 | | EP | 0875217 | 11/1998 |

| | | | | | |
|---|---|---|---|---|---|
| EP | 0633840 | 11/1999 | EP | 1575638 | 9/2005 |
| EP | 0953320 | 11/1999 | EP | 1575642 | 9/2005 |
| EP | 0971644 | 1/2000 | EP | 0900059 | 10/2005 |
| EP | 0982041 | 3/2000 | EP | 1581147 | 10/2005 |
| EP | 1105169 | 6/2001 | EP | 1586286 | 10/2005 |
| EP | 1124594 | 8/2001 | EP | 1254673 | 11/2005 |
| EP | 1127582 | 8/2001 | EP | 1261297 | 11/2005 |
| EP | 1131127 | 9/2001 | EP | 0927006 | 1/2006 |
| EP | 1132058 | 9/2001 | EP | 1621603 | 2/2006 |
| EP | 1150738 | 11/2001 | EP | 1218665 | 5/2006 |
| EP | 1172074 | 1/2002 | EP | 1222941 | 5/2006 |
| EP | 1181943 | 2/2002 | EP | 1359867 | 5/2006 |
| EP | 0914092 | 4/2002 | EP | 1656961 | 5/2006 |
| EP | 1216665 | 6/2002 | EP | 1277449 | 6/2006 |
| EP | 0747069 | 9/2002 | EP | 0836839 | 7/2006 |
| EP | 0920342 | 9/2002 | EP | 1684817 | 8/2006 |
| EP | 1242130 | 9/2002 | EP | 1687042 | 8/2006 |
| EP | 0623354 | 10/2002 | EP | 0907339 | 11/2006 |
| EP | 0806211 | 10/2002 | EP | 1359865 | 11/2006 |
| EP | 1275352 | 1/2003 | EP | 1214108 | 1/2007 |
| EP | 0850604 | 2/2003 | EP | 1416885 | 1/2007 |
| EP | 1280512 | 2/2003 | EP | 1441667 | 1/2007 |
| EP | 1280568 | 2/2003 | EP | 1192957 | 2/2007 |
| EP | 1280569 | 2/2003 | EP | 1236447 | 2/2007 |
| EP | 1294309 | 3/2003 | EP | 1764116 | 3/2007 |
| EP | 0824900 | 4/2003 | EP | 1185215 | 4/2007 |
| EP | 1308179 | 5/2003 | EP | 1442757 | 4/2007 |
| EP | 1310242 | 5/2003 | EP | 1786363 | 5/2007 |
| EP | 1314405 | 5/2003 | EP | 1787602 | 5/2007 |
| EP | 1316323 | 6/2003 | EP | 1788973 | 5/2007 |
| EP | 1339448 | 9/2003 | EP | 1796754 | 6/2007 |
| EP | 1347791 | 10/2003 | EP | 1330273 | 7/2007 |
| EP | 1347792 | 10/2003 | EP | 0900060 | 8/2007 |
| EP | 1348402 | 10/2003 | EP | 1355588 | 8/2007 |
| EP | 1348405 | 10/2003 | EP | 1355589 | 8/2007 |
| EP | 1359864 | 11/2003 | EP | 1561436 | 8/2007 |
| EP | 1365710 | 12/2003 | EP | 1863408 | 12/2007 |
| EP | 1379290 | 1/2004 | EP | 1071490 | 1/2008 |
| EP | 0902666 | 2/2004 | EP | 1096902 | 1/2008 |
| EP | 1460972 | 2/2004 | EP | 1 891 988 | 2/2008 |
| EP | 0815806 | 3/2004 | EP | 0895762 | 2/2008 |
| EP | 1400219 | 3/2004 | EP | 0916317 | 2/2008 |
| EP | 0950386 | 4/2004 | EP | 1891988 | 2/2008 |
| EP | 1461165 | 4/2004 | EP | 1402849 | 4/2008 |
| EP | 1416884 | 5/2004 | EP | 1466634 | 7/2008 |
| EP | 1424957 | 6/2004 | EP | 1572032 | 7/2008 |
| EP | 1429816 | 6/2004 | EP | 1527754 | 8/2008 |
| EP | 1448116 | 8/2004 | EP | 1968662 | 9/2008 |
| EP | 1448118 | 8/2004 | EP | 1980223 | 10/2008 |
| EP | 1449545 | 8/2004 | EP | 1988943 | 11/2008 |
| EP | 1449546 | 8/2004 | EP | 1490125 | 1/2009 |
| EP | 1453557 | 9/2004 | EP | 1829626 | 2/2009 |
| EP | 1457214 | 9/2004 | EP | 1229901 | 3/2009 |
| EP | 12544674 | 9/2004 | EP | 1128785 | 4/2009 |
| EP | 0975340 | 10/2004 | EP | 2051750 | 4/2009 |
| EP | 1319416 | 11/2004 | EP | 1427353 | 5/2009 |
| EP | 1476882 | 11/2004 | ES | 2169012 | 7/2002 |
| EP | 1479402 | 11/2004 | FR | 2867059 | 9/2005 |
| EP | 1482867 | 12/2004 | GB | 2397233 | 7/2004 |
| EP | 1011529 | 1/2005 | JP | 7002180 | 1/1995 |
| EP | 0875218 | 2/2005 | JP | 3673973 | 2/1996 |
| EP | 1181903 | 2/2005 | JP | 3249383 | 10/1996 |
| EP | 1504775 | 2/2005 | JP | 3614652 | 11/1998 |
| EP | 1042997 | 3/2005 | JP | 10295824 | 11/1998 |
| EP | 1754684 | 3/2005 | JP | 11188109 | 7/1999 |
| EP | 1520594 | 4/2005 | JP | 2000312721 | 11/2000 |
| EP | 1521603 | 4/2005 | JP | 2001098308 | 4/2001 |
| EP | 1028672 | 6/2005 | JP | 2001522640 | 11/2001 |
| EP | 1539041 | 6/2005 | JP | 2002065862 | 3/2002 |
| EP | 1543798 | 6/2005 | JP | 2002519139 | 7/2002 |
| EP | 1550472 | 6/2005 | JP | 2002523147 | 7/2002 |
| EP | 1328213 | 7/2005 | JP | 2002-308683 | 10/2002 |
| EP | 1551569 | 7/2005 | JP | 2003024449 | 1/2003 |
| EP | 1554992 | 7/2005 | JP | 2003-512098 | 4/2003 |
| EP | 1560613 | 8/2005 | JP | 2003521274 | 7/2003 |
| EP | 1562519 | 8/2005 | JP | 2003290361 | 10/2003 |
| EP | 1562654 | 8/2005 | JP | 2003-310744 | 11/2003 |
| EP | 1570808 | 9/2005 | JP | 2003533333 | 11/2003 |
| EP | 1575631 | 9/2005 | JP | 2004500925 | 1/2004 |

| | | | | | | |
|---|---|---|---|---|---|---|
| JP | 2004188314 | 7/2004 | | WO | WO 002/069848 | 9/2002 |
| JP | 2004522559 | 7/2004 | | WO | WO 002/074431 | 9/2002 |
| JP | 2004223264 | 8/2004 | | WO | WO 002/076525 | 10/2002 |
| JP | 2004267750 | 9/2004 | | WO | WO 002/078668 | 10/2002 |
| JP | 2004275748 | 10/2004 | | WO | WO 002/083039 | 10/2002 |
| JP | 2004305753 | 11/2004 | | WO | WO 002/085253 | 10/2002 |
| JP | 2005501654 | 1/2005 | | WO | WO 002/085424 | 10/2002 |
| JP | 2005502426 | 1/2005 | | WO | WO 002/085532 | 10/2002 |
| JP | 2005040584 | 2/2005 | | WO | WO 002/096389 | 12/2002 |
| JP | 2005503184 | 2/2005 | | WO | WO 003/009779 | 2/2003 |
| JP | 2005503240 | 2/2005 | | WO | WO 003/022178 | 3/2003 |
| JP | 2005507285 | 3/2005 | | WO | WO 003/024357 | 3/2003 |
| JP | 2005511139 | 4/2005 | | WO | WO 003/026713 | 4/2003 |
| JP | 2005511242 | 4/2005 | | WO | WO 003/035131 | 5/2003 |
| JP | 2005131364 | 5/2005 | | WO | WO 003/037220 | 5/2003 |
| JP | 2005152526 | 6/2005 | | WO | WO 003/037221 | 5/2003 |
| JP | 2005152527 | 6/2005 | | WO | WO 003/037223 | 5/2003 |
| JP | 2005199054 | 7/2005 | | WO | WO 003/037398 | 5/2003 |
| JP | 2005199058 | 7/2005 | | WO | WO 003/039407 | 5/2003 |
| JP | 2008516726 | 5/2008 | | WO | WO 003/045582 | 6/2003 |
| KR | 2002/0066996 | 8/2002 | | WO | WO 003/047463 | 6/2003 |
| KR | 2004/0066409 | 7/2004 | | WO | WO 003/051233 | 6/2003 |
| KR | 2005/0117361 | 12/2005 | | WO | WO 003/055414 | 7/2003 |
| NZ | 331388 | 1/2000 | | WO | WO 003/061755 | 7/2003 |
| SU | 393044 | 12/1973 | | WO | WO 003/072287 | 9/2003 |
| WO | WO1986/006617 | 11/1986 | | WO | WO 003/077802 | 9/2003 |
| WO | WO 093/06792 | 4/1993 | | WO | WO 003/083181 | 10/2003 |
| WO | WO 093/07934 | 4/1993 | | WO | WO 003/094774 | 11/2003 |
| WO | WO 093/16656 | 9/1993 | | WO | WO 02004/004602 | 1/2004 |
| WO | WO 094/16646 | 8/1994 | | WO | WO 02004/004603 | 1/2004 |
| WO | WO 095/03083 | 2/1995 | | WO | WO 02004/006491 | 1/2004 |
| WO | WO 096/04952 | 2/1996 | | WO | WO 02004/006807 | 1/2004 |
| WO | WO 096/09086 | 3/1996 | | WO | WO 02004/006976 | 1/2004 |
| WO | WO 096/32907 | 10/1996 | | WO | WO 02004/006983 | 1/2004 |
| WO | WO 097/041916 | 11/1997 | | WO | WO 02004/010900 | 2/2004 |
| WO | WO 098/17331 | 4/1998 | | WO | WO 02004/014554 | 2/2004 |
| WO | WO 098/18408 | 5/1998 | | WO | WO 02004/026177 | 4/2004 |
| WO | WO 098/23228 | 6/1998 | | WO | WO 02004/028347 | 4/2004 |
| WO | WO 098/36784 | 8/1998 | | WO | WO 02004/028587 | 4/2004 |
| WO | WO 098/38946 | 9/1998 | | WO | WO 02004/043292 | 5/2004 |
| WO | WO 098/38947 | 9/1998 | | WO | WO 02004/043298 | 5/2004 |
| WO | WO 098/040033 | 9/1998 | | WO | WO 02004/043300 | 5/2004 |
| WO | WO 098/57680 | 12/1998 | | WO | WO 02004/043509 | 5/2004 |
| WO | WO 099/16386 | 4/1999 | | WO | WO 02004/043511 | 5/2004 |
| WO | WO 099/23977 | 5/1999 | | WO | WO 02004/045464 | 6/2004 |
| WO | WO 099/042631 | 8/1999 | | WO | WO 02004/045668 | 6/2004 |
| WO | WO 099/49928 | 10/1999 | | WO | WO 02004/058100 | 7/2004 |
| WO | WO 099/52471 | 10/1999 | | WO | WO 02004/060428 | 7/2004 |
| WO | WO 099/62432 | 12/1999 | | WO | WO 02004/064911 | 8/2004 |
| WO | WO 02000/01322 | 1/2000 | | WO | WO 02004/071548 | 8/2004 |
| WO | WO 000/10622 | 3/2000 | | WO | WO 02004/072104 | 8/2004 |
| WO | WO 000/25841 | 5/2000 | | WO | WO 02004/073768 | 9/2004 |
| WO | WO 000/27303 | 5/2000 | | WO | WO 02004/080579 | 9/2004 |
| WO | WO 000/30710 | 6/2000 | | WO | WO 02004/087251 | 10/2004 |
| WO | WO 000/48660 | 8/2000 | | WO | WO 02004/096176 | 11/2004 |
| WO | WO 000/64506 | 11/2000 | | WO | WO 02004/100827 | 11/2004 |
| WO | WO 001/35928 | 5/2001 | | WO | WO 02004/101017 | 11/2004 |
| WO | WO 001/41827 | 6/2001 | | WO | WO 02004/105639 | 12/2004 |
| WO | WO 001/45862 | 6/2001 | | WO | WO 02004/108021 | 12/2004 |
| WO | WO 001/45763 | 7/2001 | | WO | WO 02004/108186 | 12/2004 |
| WO | WO 001/66036 | 9/2001 | | WO | WO 02004/108346 | 12/2004 |
| WO | WO 001/80920 | 11/2001 | | WO | WO 02004/110302 | 12/2004 |
| WO | WO 001/87263 | 11/2001 | | WO | WO 02005/004754 | 1/2005 |
| WO | WO 001/87342 | 11/2001 | | WO | WO 02005/006325 | 1/2005 |
| WO | WO 001/87374 | 11/2001 | | WO | WO 02005/011529 | 2/2005 |
| WO | WO 001/89417 | 11/2001 | | WO | WO 02005/014892 | 2/2005 |
| WO | WO 001/89420 | 11/2001 | | WO | WO 2005015596 A2 * | 2/2005 |
| WO | WO 002/026162 | 4/2002 | | WO | WO 02005/027794 | 3/2005 |
| WO | WO 002/030487 | 4/2002 | | WO | WO 02005/032456 | 4/2005 |
| WO | WO 002/038827 | 5/2002 | | WO | WO 02005/034806 | 4/2005 |
| WO | WO 002/042521 | 5/2002 | | WO | WO 02005/042049 | 5/2005 |
| WO | WO 002/043796 | 6/2002 | | WO | WO 02005/044361 | 5/2005 |
| WO | WO 002/47581 | 6/2002 | | WO | WO 02005/049520 | 6/2005 |
| WO | WO 002/058753 | 8/2002 | | WO | WO 02005/051450 | 6/2005 |
| WO | WO 002/060349 | 8/2002 | | WO | WO 02005/053766 | 6/2005 |
| WO | WO 002/060350 | 8/2002 | | WO | WO 02005/063318 | 7/2005 |
| WO | WO 002/060506 | 8/2002 | | WO | WO 02005/072437 | 8/2005 |
| WO | WO 002/064019 | 8/2002 | | WO | WO 02005/082277 | 9/2005 |
| WO | WO 002/065947 | 8/2002 | | WO | WO 02005/082283 | 9/2005 |

| | | |
|---|---|---|
| WO | WO 02005/086733 | 9/2005 |
| WO | WO 02005/089825 | 9/2005 |
| WO | WO 02005/091834 | 10/2005 |
| WO | WO 02005/099621 | 10/2005 |
| WO | WO 02005/099626 | 10/2005 |
| WO | WO 02005/110285 | 11/2005 |
| WO | WO 02005/115276 | 12/2005 |
| WO | WO 02005/115496 | 12/2005 |
| WO | WO 02005/117752 | 12/2005 |
| WO | WO 02006/014969 | 2/2006 |
| WO | WO 02006/015161 | 2/2006 |
| WO | WO 02006/020742 | 2/2006 |
| WO | WO 02006/029364 | 3/2006 |
| WO | WO 02006/029708 | 3/2006 |
| WO | WO 02006/036801 | 4/2006 |
| WO | WO 02006/055237 | 5/2006 |
| WO | WO 02006/061598 | 6/2006 |
| WO | WO 02006/063157 | 6/2006 |
| WO | WO 02006/063158 | 6/2006 |
| WO | WO 02006/074549 | 7/2006 |
| WO | WO 02006/083418 | 8/2006 |
| WO | WO 02006/104644 | 10/2006 |
| WO | WO 02006/104976 | 10/2006 |
| WO | WO 02006/105256 | 10/2006 |
| WO | WO 02006/107677 | 10/2006 |
| WO | WO 02006/116752 | 11/2006 |
| WO | WO 02006/124365 | 11/2006 |
| WO | WO 02007/016961 | 2/2007 |
| WO | WO 02007/034167 | 3/2007 |
| WO | WO 02007/070666 | 6/2007 |
| WO | WO 02007/095167 | 8/2007 |
| WO | WO 02007/124137 | 11/2007 |
| WO | WO 02007/126768 | 11/2007 |
| WO | WO 02007/130786 | 11/2007 |
| WO | WO 02007/133520 | 11/2007 |
| WO | WO 02007/143433 | 12/2007 |
| WO | WO 02007/145961 | 12/2007 |
| WO | WO 02007/147246 | 12/2007 |
| WO | WO 02008/002586 | 1/2008 |
| WO | WO 02008/002778 | 1/2008 |
| WO | WO 02008/024149 | 2/2008 |
| WO | WO 02008/024477 | 2/2008 |
| WO | WO 02008/024669 | 2/2008 |
| WO | WO 02008/033711 | 3/2008 |
| WO | WO 02008/034048 | 3/2008 |
| WO | WO 02008/036549 | 3/2008 |
| WO | WO 02008/039319 | 4/2008 |
| WO | WO 02008/045184 | 4/2008 |
| WO | WO 02008/057991 | 5/2008 |
| WO | WO 02008/061017 | 5/2008 |
| WO | WO 02008/063539 | 5/2008 |
| WO | WO 02008/082698 | 7/2008 |
| WO | WO 02008/106223 | 9/2008 |
| WO | WO 02008/108987 | 9/2008 |
| WO | WO 02008/124513 | 10/2008 |
| WO | WO 02008/124519 | 10/2008 |
| WO | WO 02008/134493 | 11/2008 |
| WO | WO 02008/140482 | 11/2008 |
| WO | WO 02008/147848 | 12/2008 |
| WO | WO 02008/147853 | 12/2008 |
| WO | WO 02009/009627 | 1/2009 |
| WO | WO 02009/009628 | 1/2009 |
| WO | WO 02009/012353 | 1/2009 |
| WO | WO 02009/014692 | 1/2009 |
| WO | WO 02009/014696 | 1/2009 |
| WO | 2009/018029 | 2/2009 |
| WO | 2009/018035 | 2/2009 |
| WO | WO 02009/020520 | 2/2009 |
| WO | WO 02009/050168 | 4/2009 |
| WO | WO 2009050168 A1 * | 4/2009 |
| WO | WO 02009/059081 | 5/2009 |
| WO | WO 02009/059085 | 5/2009 |
| WO | WO 02009/059086 | 5/2009 |
| WO | WO 02009/059098 | 5/2009 |
| WO | WO 02009/059129 | 5/2009 |
| WO | WO 02009/059141 | 5/2009 |
| WO | WO 02009/059146 | 5/2009 |
| WO | WO 02009/059165 | 5/2009 |
| WO | WO 02009/059166 | 5/2009 |
| WO | WO 02009/059180 | 5/2009 |
| WO | WO 02009/059196 | 5/2009 |
| WO | WO 02009/089382 | 7/2009 |
| WO | WO 02009/091384 | 7/2009 |
| WO | WO 02009/094270 | 7/2009 |
| WO | WO 02009/126766 | 10/2009 |
| WO | WO 02009/135008 | 11/2009 |
| WO | WO 02009/137786 | 11/2009 |
| WO | 2009/148821 | 12/2009 |
| WO | WO 02010/030873 | 3/2010 |
| ZA | 9710342 | 6/1998 |

OTHER PUBLICATIONS

Bu et al., "Synthesis of $TiO_2$ Porous Thin Films by Polyethylene Glycol Templating and Chemistry of the Process," Journal of the European Ceramic Society, vol. 25, pp. 673-679 (2005).
Kim et al., "Fabrication and Characterization of $TiO_2$ Thin Film Prepared by a Layer-By-Layer Self-Assembly Method," Thin Solid Films, vol. 499, pp. 83-89, (2006).
Zheng et al., "Synthesis of Mesoporous Silica Materials via Nonsurfactant Templated Sol-Gel Route Using Mixture of Organic Compounds as Template," Journal of Sol-Gel Science and Technology, vol. 24. pp. 81-88, (2002).
International Preliminary Report on Patentability issued on Dec. 29, 2010, in PCT application No. PCT/US2009/047634, filed on Jun. 17, 2009.
"Cyclic voltammetry"—from Wikipedia, (http://en.wikipedia.org/wiki/Cyclic_voltammetry), pp. 1-3, (downloaded [2007]).
"Electrophoretic deposition"—from Wikipedia, (http://en.wikipedia.org/wiki/electrophoretic_deposition), pp. 1-8, (downloaded [2007]).
"Impressive Progress in Interventional Cardiology—From 1st Balloon Inflation to First Bioabsorbable Stent," Medical News Today, pp. 1-2, May 15, 2006, (http://www.medicalnewstoday.com/articles/43313.php).
"Inorganic Polymers", Polymer Science Learning Center, Department of Polymer Science, University of Southern Mississippi, 5 pages, [first accessed Aug. 17, 2011].
"JOMED Starts Clinical Studies on Tacrolimus-Eluting Coronary Stents," Jomed Press Release, 2 pages, Jan. 14, 2002.
"Nano PLD," PVD Products, Inc. Wilmington, Ma, pp. 1-2, (2003).
"Paclitaxel"—from Wikipedia, (http://en.wikipedia.org/wiki/Paclitaxel), 12 pages, (downloaded Sep. 14, 2011).
"Sputtering," Wikipedia.com, (http://en.wikipedia.org/wiki/Sputtering), pp. 1-5, (downloaded [2009]).
"Ultraviolet-Ozone Surface Treatment," Three Bond Technical News #17, pp. 1-10, Issued Mar. 20, 1987, (http://www.threebond.co.jp/en/technical/technicalnews/pdf/tech17.pdf).
Abbott et al., "Voltammetric and impedance studies of the electropolishing of type 316 stainless steel in a choline chloride based ionic liquid," Electrochimica Acta, vol. 51, pp. 4420-4425, (2006).
Abstract: "Edelstahlfreier stent aus niobium mit iridiumoxyd (IrOx)-beschichtung: Erste Ergebnisse der Lusty-studie", (Stainless steel-free Stent out of niobium with iridiumoxyd (IrOx)-coating: Initial results of the Lusty-study), Annual Meeting of the German Society for Cardiology, Apr. 24-26, 2003.
Adanur et al., "Nanocomposite Fiber Based Web and Membrane Formation and Characterization," Journal of Industrial Textiles, vol. 36, No. 4, pp. 311-327, Apr. 2007.
Advincula et al., "Surface modification of surface sol-gel derived titanium oxide films by self-assembled monolayers (SAMs) and non-specific protein adsorption studies," Colloids and Surfaces B: Biointerfaces, vol. 42, pp. 29-43, (2005).
Akhras, "Bare metal stent, lunar IrOx2 coated or drug-eluting stent for patients with CAD?", PowerPoint presentation, pp. 1-20, Oct., 2006.
Akhras, "Comparison of Iridiumoxide Coated Stent with Paclitaxel-Eluting Stent and a Bare Metal Stent in Patients With Coronary Artery Disease"; Abstract, 1 p., Oct. 2006.
Al-Lamee, "Programmable Elution Profile Coating for Drug-Eluting Stents," Medical Device Technology: Materials, pp. 12-15, Mar. 2005.

Amanatides et al., "Electrical and optical properties of CH4/H2 Rf plasmas for diamond-like thin film deposition," Diamond & Related materials, vol. 14, pp. 292-295, (2005).

Amberg et al., "Silver Deposition on Temperature Sensitive Substrates by Means of an Inverted Cylindrical Magnetron," Poster, 1 page, 2003.

Anders, "Ion Plating and Beyond: Pushing the Limits of Energetic Deposition," Vacuum Technology & Coating, pp. 41-46, Dec. 2002.

Andersson et al., "Influence of Systematically Varied Nanoscale Topography on the Morphology of Epithelial Cells," IEEE Transactions on Nanobioscience, vol. 2, No. 2, pp. 49-57, Jun. 2003.

Andersson et al., "Nanoscale features influence epithelial cell morphology and cytokine production," Biomaterials, 2003. vol. 24, No. 20, pp. 3427-3436, (2003).

Annis et al., "An Elastomeric Vascular Prosthesis," Transactions—American Society for Artificial Internal Organs. vol. XXIV, pp. 209-214, (1978).

Ansell et al., "X-Ray Rhotoelectron Spectroscopic Studies of Tin Electrodes after Polarization in Sodium Hydroxide Solution," Journal of Electrochemical Society: Electrochemical Science and Technology, vol. 124, No. 9, pp. 1360-1364, Sep. 1977.

Antunes et al., "Characterization of Corrosion Products Formed on Steels in the First Months of Atmospheric Exposure", Materia, vol. 8, No. 1, pp. 27-34, (2003).

Armani et al., "Microfabrication Technology for Polycaprolactone, a Biodegradable Polymer," Journal of Micromechanics and Microengineering, vol. 10, pp. 80-84, (2000).

Arnold et al., "Activation of Integrin Function by Nanopatterned Adhesive Interface," ChemPhysChem, vol. 5, pp. 383-388, (2004).

Ashfold et al., "Pulsed laser ablation and deposition of thin films," Chem. Soc. Rev., vol. 33, pp. 23-31, (2004).

Asoh et al., "Conditions for Fabrication of Ideally Ordered Anodic Porous Alumina Using Pretextured Al," Journal of the Electrochemical Society, vol. 148, pp. B152-B156, (2001).

Atanasoska et al., "Xps Studies on Conducting Polymers: Polypyrrole Films Doped with Perchlorate and Polymeric Anions," Chemistry Materials vol. 4, pp. 988-994, (1992).

Aughenbaugh et al., "Silica sol-gel for the controlled release of antibiotics. Ii. The effect of synthesis parameters on the in vitro release kinetics of vancomycin," Journal of Biomedical Materials Research, vol. 57, No. 3, pp. 321-326, Dec. 5, 2001.

Awad et al., "Deposition of duplex A1203/TiN coatings on aluminum alloys for tribological applications using a combined microplasma oxidation (MPO) and arc ion plating (AIP)," Wear, vol. 260, pp. 215-222, (2006).

AxynTec product review, AxynTec Dunnschichttechnik GmbH (www.axyntec.de), pp. 1-8, (2002).

Ayon et al., "Drug loading of nonopouros TiO2 films," Institute of Physics Publishing, Biomedical Materials, vol. 1, pp. L11-L15, (2006).

Azom, "Porous Coatings for Improved Implant Life - Total Hip Replacements," pp. 1-7, [downloaded Sep. 1, 2005], (http://www.azom.com/Details.asp?ArticleID=1900).

Bak et al., "Electrodeposition of polymer next to the three-phase boundary," Electrochemisty Communications, vol. 7, pp. 1098-1104, (2005).

Balamuguran et al., "Bioactive Sol-Gel Hydroxyapatite Surface for Biomedical Applications-In Vitro Study," Trends in Biomaterials & Artificial Organs, vol. 16, No. 1, pp. 18-20, (2002).

Balas et al., "Formation of Bone-Like Apatite on Organic Polymers Treated with a Silane-Coupling Agent and a Titania Solution," Biomaterials, vol. 27, pp. 1704-1710, (2006).

Balaur et al., "Tailoring the wettability of TiO2 nanotube layers," Electrochemistry Communications, vol. 7, pp. 1066-1070, (2005).

Banks et al., "Femtosecond Laser-Induced Forward Transfer (LIFT): a Technique for Versatile Micro-Printing Applications," European Conference on Lasers and Electro-Optics and the International Quantum Electronics Conference, 1 p., Jun. 17-22, 2007.

Banks et al., "Nano-droplets Deposited in Microarrays by Femtosecond Ti: Saphire Laser-Induced Forward Transfer," Optoelectronics Reaserch Centre, University of Southhampton, Applied Physics Letters, vol. 89, Issue 19, pp. 1-12, (2006).

Barbucci et al, "Micro and nano-structured surfaces,: Journal of Materials Science: Materials in Medicine", vol. 14, No. 8, pp. 721-725, (2003).

Bates et al. "Description of research activites: Block copolymers," Organization for Minnesota Nanotechnology Institute, University of Minnesota, pp. 1-2, (2002).

Bayoumi et al., "Formation of self-organized titania nano-tubes by dealloying and anodic oxidation," Electrochemistry Communications, vol. 8, pp. 38-44, (2006).

Békési et al., "Efficient Submicron Processing of Metals with Femtosecond UV Pulses," Applied Physics a, vol. 76, pp. 355-357 (2003).

Benson, "Drug Delivery Technology and Access," Polygenetics, Inc., pp. 1-10, Oct. 2005.

Benson, "Highly Porous Polymers," American Laboratory, pp. 1-14, Apr. 2003.

Berg et al., "Controlled Drug Release from Porous Polyelectrolyte Multilayers," Biomacromolecules, vol. 7, pp. 357-364, (2006).

Berkland et al., "Controlling surface nano-structure using flow-limited field-injection electrostatic spraying (Ffess) of poly(D,L-lactide-co-glycolide)," Biomaterials, vol. 25, pp. 5649-5658, (2004).

Belly et al., "The fibroblast response to tubes exhibiting internal nanotopography," Biomaterials, vol. 26, No. 24, pp. 4985-4992, (2005).

Biederman et al. "Plasma Polymer-Metal Composite Films," Plasma Deposition, Treatment and Etching of Polymers, pp. 269-320, (1990).

Bock et al., "Anion and water involvement in hydrous Jr oxide redox reactions in acidic solutions," Journal of Electroanalytical Chemistry, vol. 475, pp. 20-27, (1999).

Bolle et al., "Characterization of submicrometer periodic structures produced on polymer surfaces with low-fluence ultraviolet laser radiation," Journal of Applied Physics, vol. 73, No. 7, pp. 3516-3524, Apr. 1, 1993.

Bolzan et al., "The Potentiodynamic behaviour of iridium electrodes in aqueous 3.7 M H2SO4 in the 293-195 K Range," Journal of Electroanalytical Chemistry, vol. 461, pp. 40-51, (1999).

Boulmedais et la., "Controlled Electrodissolution of Polyelectrolyte Multilayers: a Platform Technology Towards the Surface-Initiated Delivery of Drugs," Advanced Functional Materials, vol. 63, pp. 63-70, (2006).

Boura et al., "Endothelial cell—interactions with polyelectrolyte multilayer films," Biomaterials, vol. 26. pages 4568-4575, (2005).

Bradley et al., "Visuotopic Mapping Through a Multichannel Stimulating Implant in Primate V1," Journal of Neurophysiology, vol. 93, pp. 1659-1670, (2005).

Bretagnol et al., "Functional Micropatterning Surface by Combination of Plasma Polymerization and Lift-Off Process," Plasma Process and Polymers, vol. 3, pp. 30-38, Nov. 14, 2005.

Bretagnol et al., "Surface Functionalization and Patterning Techniques to Design Interfaces for Biomedical and Biosensor Applications," Plasma Processes and Polymers, vol. 3, pp. 443-455, (2006).

Brody et al., "Characterization Nanoscale topography of the Aortic Heart Valve Basement Membrane for Tissue Engineering Heart Valve Scaffold Design," Tissue Engineering, vol. 12, No. 2, pp. 413-421, Nov. 2, 2006.

Bruckner et al., "Metal plasma immersion ion implantation and deposition (MPIIID): chromium on magnesium," Surface and Coatings Technology, vol. 103-104, pp. 227-230, (1998).

Brunetti et al., "Oxide/hydroxide films on tin. Part I: Kinetic aspects of the electroformation and electroreductions of the films," Journal of Electroanalytical Chemisty, pp. 1-7, (2007).

Bu et al., "Preparation of nanocrystalline TiO2 porour films from terpineol-ethanol-Peg system," Journal of Materials Science, vol. 41, pp. 2067-2073, (2006).

Bu et al., "Synthesis of TiO2 Porous Thin Films by Polythylene Glycol Templating and Chemistry of the Process," Journal of the European Ceramic Society, vol. 25, pp. 673-679 (2005).

Burmeister et al., "Colloid Monolayers as Versatile Lithographic Masks," Langmuir, vol. 13, pp. 2983-2987, (1997).

Buster et al., "Crystal habits of the Magnesium Hydroxide mineral Brucite within Coral Skeletons," American Geophysical Union Annual Meeting, Abstract and Poster, pp. 1-3, (2006).

Buttiglieri et al., "Endothelization and adherence of leucocytes to nanostructured surfaces," Biomaterials, vol. 24, pp. 2731-2738, (2003).

Calcagno et al., "Structural modification of polymer films by ion irradiation," Nuclear Instruments and Methods in Physics Research, vol. B65, pp. 413-422, (1992).

Carp et al., "Photoinduced Reactivity of Titanium Dioxide," Progress in Solid State Chemistry, vol. 32, pp. 33-177, (2004).

Caruso, "Nanoscale Particle Modifications via Sequential Electrostatic Assembly," Colloids and Colloid Assemblies: Synthesis, Modification, Organization and Utilization of Colloid Particles, pp. 266-269, Mar. 19, 2004.

Cassak, "Art: Bucking the Trend in Bioabsorbable Stents", Windhover Information Inc., in Vivo June, pp 1-14, 2008.

Catledge et al, "Structure and Mechanical Properties of Functionally-Graded Nanostructured Metalloceramic Coatings," Mat. Res. Soc. Symp. Proc. vol. 778, ppU7.8.-U7.8.6, (2003).

Catledge et al., "Structural and mechanical properties of nanostructured metalloceramic coatings on cobalt chrome alloys," Applied Physics Letters, vol. 82, No. 10, pp. 1625-1627, Mar. 10, 2003.

Caves et al., "The evolving impact of microfabrication and nanotechnology on stent design," Journal of Vascular Surgery, pp. 1363-1368, Dec. 2006.

Caves et al., "The evolving impact of microfabrication and nanotechnology on stent design," Journal of Vascular Surgury, vol. 44, pp. 1363-1368, (2006).

Cernigoj et al., "Photocatalytically Active TiO2 Thin Films Produced by Surfactant-Assistant Sol-Gel Processing," Thin Solid Films, vol. 495, pp. 327-332, (2006).

Ceruti et al., "Preparation, characterization, cytotoxicity and pharmacokinetics of liposomes containing water-soluble prodrugs of paclitaxel," Journal of Controlled Release, vol. 63, pp. 141-153, (2000).

Champagne et al., "Nanometer-scale scanning sensors fabricated using stencil lithography," Applied Physics Letters, vol. 82, No. 7, pp. 1111-1113, Feb. 17, 2003.

Chandra et al., "Biodegradable Polymers," Progress in Polymer Science, vol. 23, pp. 1273-1335, (1998).

Chang et al., "Preparation and Characterization of Nanostructured Tin Oxide Films by Electrochemical Deposition," Electrochemical and Solid-State Letters, vol. 5, No. 8, pp. C71-C74, (2002).

Chen et al., "Blood compatiblity and sp3/sp2 contents of diamond-like carbon (DLC) synthesized by plasma immersion ion implantation-deposition," Surface and Coatings Technology, vol. 156, pp. 289-294, (2002).

Chen et al., "Fabrication of micro-field emitters on ceramic substrates," Microelectronic Engineering, vol. 84, pp. 94-100, (2007).

Chen et al., "Behavior of Cultured Human Umbilical Vein Endothelial Cells on Titanium Oxie Films Fabricated by Plasma Immersion Ion Implantation and Deposition," Surface & Coatings Technology, vol. 186, pp. 270-276, (2004).

Cheng et al., "Anatase Coating on NiTi Via a Low-Temperature Sol-Gel Route for Improving Corrosion Resistance," Scripta Materialia, vol. 51, pp. 1041-1045, (2004).

Cho et al., "A Novel Route to Three-Dimensionally Ordered Macroporous Polymers by Electron Irradiation of Polymer Colloids" Advanced Materials, vol. 17, No. 1, pp. 120-125, Jan. 6, 2005.

Cho et al., "Influence of Silica on Shape Memory Effect and Mechanical Properties of Polyurethane-Silica Hybrid," European Polymer Journal, vol. 40, pp. 1343-1348, (2004).

Cho et al., "Preparation and Characterization of Iridium Oxide Thin Films Grown by Dc Reactive Sputtering," Japanese Journal of Applied Physics, vol. 36, Part 1, No. 3B, pp. 1722-1727, Mar. 1997.

Choi et al., "Synthesis and Characterization of Diamond-Like Carbon Protective Ar Coating," Journal of the Korean Physical Society, vol. 45, p. S864, Dec. 2004.

Chougnet et al., "Substrates do influence the ordering of mesoporous thin films," Journal of Materials Chemistry, vol. 15, pp. 3340-3345, (2005).

Chougnet et al., "The Influence of the Nature of the Substrate on the Ordering of Mesoporous Thin Films," Thin Solid Films, vol. 495, pp. 40-44, (2006).

Chow et al., "Nanostructured Films and Coating by Evaporation, Sputtering, Thermal Spraying, Electro and Electroless Deposition," Handbook of Nanophase and Nanostructured Materials, vol. 1, Chapter 9, pp. 246-272, (2003).

Chow et al., "Preliminary Evaluation of Kem for Fabrication," Proceedings of the 12th General Meeting of Jowog 31, Livermore, Ca, University of California, pp. 1-7, (1996).

Chronakis, "Novel nanocomposites and nanoceramics based on polymer nanofibers using electrospinning process - a review," Journal of Materials Processing Technology, vol. 167, pp. 283-293, (2005).

Chu, "Recent developments and applications of plasma immersion ion implantation," Journal of Vacuum Science Technology, vol. B22, No. 1, pp. 289-296, Jan./Feb. 2004.

Chuang et al., "Titanium Oxide and Polyaniline Core-Shell Nanocomposites," Synthetic Metals, vol. 152, pp. 361-364, (2005).

Chung et al., "Roles of discontinuities in bio-inspired adhesive pads," Journal of the Rolyal Society: Interface, vol. 2, pp. 55-61, Feb. 8, 2005.

Clark, "Micropatterning Cell Adhesiveness", Immobilized Biomolecules in Analysis, Oxford University Press, pp. 95-111, (1998).

Clevy et al., "Micromanipulation and Micro-Assembly Systems," IEEE/RAS International Advanced Robotics Program, IARP'06, Paris, France, pp. 1-6, (2006).

Colina et al., "DNA deposition through laser induced forward transfer," Biosensors and Bioelectronics, vol. 20, pp. 1638-1642, (2005).

Costanzo et al., "Model-Based Simulations to Engineer Nanoporous Thin Films," LPCM Research, Pennsylvania State University, pp. 1-3, (2004), (http://1pcm.esm.psu.edul-tjy107/research.htm).

Course: C-103, "An Introduction to Physical Vapor Deposition (PVD) Processes," Society of Vacuum Coaters, SVC Education Programs: course description and syllabus, pp. 1-4, Apr. 19, 2008.

Course: C-208, "Sputter Deposition in Manufacturing" Society of Vacuum Coaters, SVC Education Programs: course description and syllabus, pp. 1-5, Apr. 22, 2008.

Csete et al., "The existence of sub-micrometer micromechanical modulation generated by polarized UV laser illumination on polymer surfaces," Materials Science and Engineering C, vol. 23, pp. 939-944, (2003).

Csete et al., "The role of original surface roughness in laser-induced periodic surface structure formation process on poly-carbonate films," Thin Solid Films, vol. 453-454, pp. 114-120, (2004).

Curtis et al. "Cells react to nanoscale order and symmetry in their surroundings," IEEE Transactions on Nanobioscience, vol. 3, No. 1, pp. 61-65, Mar. 2004.

Curtis et al., "Nantotechniques and approaches in biotechnology," Trends in Biotechnology, vol. 19, No. 3, pp. 97-101, Mar. 2001.

Curtis et al., "New Depths in Cell Behaviour: Reactions of Cells to Nanotopography," Biochem, Soc, Symp, vol. 65, pp. 15-26, (1999).

Curtis et al., "New depths in cell behaviour: Reactions of cells to nanotopography," Biochemical Society Symposium, No. 65, pp. 15-26 (1997).

Curtis et al., "Topographical Controls of Cells," Biomaterials, vol. 18, pp. 1573-1583, (1997).

Curtis, "Tutorial on the biology of nanotopography," IEEE Transactions on Nanobioscience, vol. 3, No. 4, pp. 293-295, Dec. 2004.

Cyster et al., "The effect of surface chemistry and nanotopography of titanium nitride (TiN) films on 3T3-L1 fibroblasts," Journal of Biomedical Materials Research: a., vol. 67, No. 1, pp. 138-147, Oct. 2003.

Cyster et al., "The effect of surface chemistry and nanotopography of titanium nitride (TiN) films on primary hippocampal neurones," Biomaterials, vol. 25, pp. 97-107, (2004).

da Cruz et al., "Preparation, structure and electrochemistry of a polypyrrole hybrid film with [Pd(dmit)2]2-, bis(1,3-dithiole-2-thione-4,5-dithiolate)palladate(Ii)," Electrochimica Acta, vol. 52, pp. 1899-1909, (2007).

Dalby et al., "In vitro reaction of endothelial cells to polymer demixed nanotopography," Biomaterials, vol. 23, No. 14, pp. 2945-2954, (2002).

Dalby, "Topographically induced direct cell mechanotransduction," Medical Engineering & Physics, vol. 27, No. 9, pp. 730-742, (2005).

Damen et al., "Paclitaxel Esters of Malic Acid as Prodrugs with Improved Water Solubility," Bioorganic & Medicinal Chemistry, vol. 8, pp. 427-432, (2000).

D'Aquino, "Good Drug Therapy: It's Not Just the Molecule - It's the Delivery," Cep Magazine, (www.cepmagazine.org), 3 pp., Feb. 2004.

Datta et al., "Fundamental aspects and applicatio of electrochemical microfabrication," Electrochimica Acta, vol. 45, pp. 2535-2558, (2000).

Daxini et al., "Micropatterned polymer surface inprove retention of endothelial cells exposed to flow-induced shear stress," Biorheology, vol. 43, pp. 45-55, (2006).

De Aza et al., "Crack growth resistance of alumina, zirconia and zirconia toughened alumina ceramics for joint prostheses," Biomaterials, vol. 23, No. 3, pp. 937-945, Feb. 2002.

Deakin et al., "De-alloying of type 316 stainless steel in hot, concentrated sodium hydroxide solution," Corrosion Science, vol. 46, pp. 2117-2133, (2004).

Debiotech, "Debiostar, an Innovative Solution for Sustained Drug Delivery," pp. 1-4, Copyright 2001, (http://www.debiotech.com/products/drugdd/stent_page_1.html).

Debiotech, "Debiostent: an Innovatice Ceramic Coating for Implantable Medical Devices," pp. 12, [first downloaded on Sep. 1, 2005], (http://www.debiotech.com/products/drugdd/stent_page_.html).

Debiotech, "Debiostent: Polymer free drug eluting coating," Jun. 14, 2007, pp. 1-2, (www.debiotech. com/products/dmggd/stent_page_1 .html).

Debiotech, "Debiotech Obtains Exclusive Rights to an Innovative Drug Eluting Stent Technology," Press release, 1 p., Mar. 7, 2003.

Demisse, "Computational Investigation of Conducting Polythiophenes and Substituted Polythiophenes," a Thesis Submitted to the School of Graduate Studies of Addis Ababa University, Ethiopia, pp. 1-86, Jun. 2007.

Deniau et al., "Study of the polymers obtained by electroreduction of methacrylonitrile," Journal of Electroanalytical Chemistry, vol. 505, pp. 33-43, (2001).

Desai et al., of micromachined silicon membranes for imrnunoisolation and biosepearation applications," Journal of Membrane Science", vol. 159, pp. 221-231, (1999).

Desai et al., "Use of Microfabricated Nanopore' Membranes as a Rate-Limiting Barrier to Diffusion of Small and Large Molecules: Possible Role in Drug Delivery" BioMEMs and Nanotechnology World, pp. 1-2, (2001).

Desai, "Integrating Cells with Microsystems: Application in Tissue Engineering and Cell-Based Delivery, PowerPoint presentation", pp. 1-41, May 10, 2002.

Di Mario et al., "Drug-eluting bioabsorbable magnesium stent," Journal of Interventional Cardiology, vol. 17, Issue 6, pp. 1-5, Dec. 2004.

Di Mario et al., "Moonlight: a controlled registry of an iridium oxide-coated stent with angographic follow-up," International Journal of Cardiology, vol. 95, pp. 329-331, (2004).

Di Mario, the Moonlight Study: Multicenter Objective Observational Lunar Iridium Oxide Intimal Growth Trial, PowerPoint presentation, pp. 1-10, (2002).

Dibra et al., "Influence of the stent surface topology on the outcomes of patients undergoing coronary stenting: a randomized double-blind controlled trial", Catheterization and Cardiovascular Interventions, vol. 65, pp. 374-380, (2005).

Dittmar et al., "Nanostructured Smart Drug Delivery Coatings," European Cells and Materials, vol. 31, Supplimentt 2, p. 73, (2007).

Dong et al., "Preparation of Submicron Polypyrrole/Poly(methly methacrylate) Coaxial Fibers and conversion to Polypyrrole Tubes and Carbon Tubes," Langmuir, vol. 22, pp. 11384-11387, (2006).

Doraiswamy et al., "Excimer laser forward transfer of mammalian cells using a novel triazene absorbing layer," Applied Surface Science, vol. 252, pp. 4743-4747, (2006).

DTI Technology Group: Materials-Coating, "Kinetic spray coating method," www.delphi.com, 1 page, July 2004.

Dumas et al., "Characterization of magnesium fluoride thin films produced by argon ion beam-assisted deposition," Thin Solid Films, vol. 382, pp. 61-68, (2001).

Duncan et al., "Polymer-drug conjugates, PDEPTand PELT: basic principals for design and transfer from laboratory to clinic," Journal of Controlled Release, vol. 74, pp. 135-146, (2001).

Duncan, "The Dawning Era of Polymer Therapeutics," Nature Reviews: Drug Discovery, vol. 2, pp. 347-360, May 2003.

Dutta et al., "Self-Organization of Colloidal Nanoparticles," Encyclopedia of Nanoscience and Nanotechnology, vol. 9, pp. 617-640, (2003).

Duwez et al., "Mechanochemistry: targeted delivery of single molecules," Nature Nanotechnology, vol. 1, pp. 122-125, (2006).

EAG Technical Note, "Functional Sites on Non-polymeric Materials: Gas Plasma Treatment and Surface Analysis," Evans Analytical Group, pp. 1-2, (2003).

Eberli et al., "The Lunar Coronary Stent System," Handbook of coronary stents, 4th edition, Chapter 17, 11 pp., (Martin Dunitz Ltd 2002).

Eesley et al., "Thermal properties of kinetics spray Al-SiC metal-matrix composite," Journal of Materials Research, vol. 18, No. 4, pp. 855-860, April 2003.

Egerhazi et al., "Thickness distribution of carbon nitride films grown by inverse-pulsed laster deposition," Applied Surface Science, vol. 247, pp. 182-187, (2005).

Electropolymerization, (http://intel.ucc.ie/sensors/Electropolym. htm), pp. 1-2, (downloaded [2007]).

Erlebacher et al., "Evolution of nonoporosity in dealloying," Nature, vol. 410, pp. 450-453, Mar. 22, 2001.

Esrom et al., "New approach of a laser-induced forward transfer for deposition of patterned thin metal films," Applied Surface Science, vol. 86, pp. 202-207, (1995).

Faupel et al., "Microstructure of pulsed laser deposited ceramic-metal and polymer-metal nanocomposite thin films," Applied Physics a, vol. 79, pp. 1233-1235 (2004).

Faust et al., "Biofunctionalised Biocompatible Titania Coatings for Implants," Euro Ceramics Vii, Key Engineering Materials, vol. 206, No. 2, pp. 1547-1550, (2006).

Fernandez-Pradas et al., "Laser-induced forward transfer of biomolecules," Thin Solid Films, vol. 453-454, pp. 27-30, (2004).

Ferraz et al., "Influence of nanoporesize on platelet adhesion and activation," Journal of Materials Science: Materials in Medicine, vol. 19, pp. 3115-3121, (2008).

Figallo et al., "Micropatterned Biopolymer 3D Scaffold for Static and Dynamic Culture of Human Fibroblasts," Biotechnology Progress, vol. 23, pp. 210-216, (2007).

Finkelstein et al., "Local drug delivery via a coronary stent with programmable release pharmacokinetics," Circulation, vol. 107, pp. 777-784, Jan. 13, 2003.

Flemming et al., "Effects of synthetic micro- and nano-structured surfaces on cell behavior," Biomaterials, vol. 20, No. 6, pp. 573-588, (1999).

Fogarassy et al., "Laser-induced forward transfer: a new approach for the deposition of high Tc superconducting thin films," Journal of Materials Research, vol. 4, No. 5, pp. 1082-1086, Sep./Oct. 1989.

Fonseca et al., "Paclitaxel-loaded Plga nanoparticles: preparation, physicochemical characterization and in vitro anti-tumoral activity," Journal of Controlled Release, vol. 83 pp. 273-286, (2002).

Forty, "Corrosion micromorphology of noble metal alloys and depletion gilding," Nature, vol. 282, pp. 597-598, Dec. 6, 1979.

Frechet, "Functional Polymers: from Plastic Electronics to Polymer-Assisted Therapeutics," Progress in Polymer Science, vol. 30, pp. 844-857, (2005).

Free Online Dictionary, "Aperture," definition, [first viewed Oct. 9, 2009].

Freitas et al., "Nimesulide PLA microsphere as a potential sustained release system for the treatment of inflammatory diseases," International Journal of Pharmaceutics, Vo. 295, pp. 201-211, (2005).

Freitas, "Nanomedicine, vol. I: Basic Capabilities," Landes Bioscience, pp. 87, 90, 255 and 265, (1999).

Friedrich et al., "Developing Interdisciplinary Undergraduate and Graduate Courses Through the Integration of Recent Research Results into the Curricula," (http://www.ineer.org/Events/ICEE1997/Proceedings/paper326.htm), 10 pages, [first downloaded Mar. 10, 2005.].

Fu et al., "Effects of mesh-assisted carbon plasma immersion ion implantation on the surface propoerties of insulating silicon carbide ceramics," Journal of Vacuum Science Technology, vol. A22, No. 2, pp. 356-360, Mar./Apr. 2004.

Fu et al., "Influence of thickness and dielectric properties on implantation efficacy in plasma immersion ion implantation of insulators," Journal of Applied Physics, vol. 95, No. 7, pp. 33193323, Apr. 1, 2004.

Fujisawa et al., "A novel textured surface for blood-contact," Biomaterials, vol. 20, pp. 955-962, (1999).

Fulton, "Ion-Assisted Filtered Cathodic Arc Deposition (IFCAD) System for vol. Production of Thin-Film Coatings," Society of Vacuum Coaters, 42nd Annual Technical Conference Proceedings, (1999).

Gabel et al., "Solid-State Spray Forming of Aluminum Near-Net Shapes," Journal of Metals, vol. 49, No. 8, pp. 31-33, (1997).

Gabel, "Low Temperature Metal Coating Method," Lawrence Livermore National Laboratory, p. 1-4, Apr. 3, 2000.

Gadegaard et al., "Tubes with Controllable Internal Nanotopography," Advanced Materials, vol. 16, No. 20, pp. 1857-1860, Oct. 18, 2004.

Galinski et al., "Ionic liquids as electrolytes," Electrochimica Acta, vol. 51, 5567-5580, (2006).

Gao, "Chemical Vapor Deposition," Handbook of Nanophase and Nanostructured Materials, vol. 1: Synthesis, Chapter 5, (2003).

Geretovszky et al., "Correlation of compositional and structural changes during pulsed laser deposition of tantalum oxide films," Thin Solid Films, vol. 453-454, pp. 245-250, (2004).

Gillanders et al., "A Composite Sol-Gel/Fluoropolymer Matrix for Dissolved Oxygen Optical Sensing," Journal of Photochemistry and Photobiology a: Chemistry, vol. 163, pp. 193-199, (2004).

Glocker et al., "Ac Reactive Sputtering with Inverted Cylindrical Magnetrons," Society of Vacuum.

Glocker et al., "Recent developments in inverted cylindrical magnetron sputtering," PowerPoint presentation, pp. 1-21, (2001).

Glocker et al., "Recent developments in inverted cylindrical magnetron sputtering," Surface and Coatings Technology, vol. 146-147, pp. 457-462, (2001).

Goddard et al., "Polymer surface modification for the attachmend of bioactive compounds," Progress in Polymer Science, vol. 32, pp. 698-725, (2007).

Goh et al., "Nanostructuring Titania by Embossing with Polymer Molds Made from Anodic Alumina Templates," Nano Letters, vol. 5, No. 8, pp. 1545-1559, (2005).

Gollwitzer et al., "Titania Coating as Local "Drug" Delivery System with Antibacterial and Biocompatible Properties," 1 p., (2003).

Gong et al., "Controlled molecular release using nanopourous alumina capsules," Biomedical Microdevices, vol. 5, No. 1, pp. 75-80, Mar. 2003.

Gong et al., "Titanium oxide nanotube arrays prepared by anodic oxidation," Journal of Material Research, vol. 16, No. 12, pp. 3331-3334, (2001).

Goodison et al., "CD44 cell adhesion molecules," Journal of Clinical Pathology: Molecular Pathology, vol. 52, pp. 189-196, (1999).

Goodman et al., "Three-dimensional extracellular matrix textured biomaterials," Biomaterials, vol. 17, pp. 2087-295, (1996).

Gorb et al., "Biological microtribology: anisotropy in frictional forces of orthopteran attachment pads reflects the unitrastructure of a highly deformable material," Proceeding of the Royal Society, London series B, vol. 267, pp. 1239-1244, (2000).

Gotszalk et al., "Diagnostics of micro- and nanostructure using the scanning probe microscopy," Journal of Telecommunications and Information Technology, pp. 41-46, (2005).

Granqvist et al., "Biodegradable and bioactive hybrid organic-inorganic Peg-siloxane fibers: Preparation and Characterization," Colloid Polymer Science, vol. 282, pp. 495-501, (2004).

Greeley et al., "Electrochemical dissolution of surface alloys in acids: Thermodynamic trends from first-principles calculations," Electrochimica Acta, vol. 52, pp. 5829-5836, (2007).

Green et al., "Xps Characterisation of Surface Modified Ni-Ti Shape Memory Alloy," Materials Science and Engineering, vol. A224, pp. 21-26, (1997).

Gressel-Michel et al., "From a Microwave Flash-Synthesized TiO2 Colloidal Suspension to TiO2 Thin Films," Journal of Colloid and Interface Science, vol. 285, pp. 674-679, (2005).

Groth et al., "Layer-by-Layer Deposition of Polyelectrolytes - a Versatile Tool for the in Vivo Repair of Blood Vessels," Angewandte Chemie, International Edition, vol. 43, pp. 926-928, (2004).

Grubmuller, "What happens if the Room at the Bottom Runs Out? a Close Look at Small Water Pores," Pnas, vol. 100, No. 13, pp. 7421-7422, Jun. 24, 2003.

Gu et al., "Biomimetic titanium dioxide film with structural color and extremely stable hydrophilicity," Applied Physics Letters, vol. 85, No. 21, pp. 5067-5069 (2004).

Guangliang et al., "The effects of current density on the phase composition and microstructure properties of micro-arc oxidation coating," Journal of Alloys and Compounds, vol. 345, pp. 169200, (2002).

Guo et al., "Formation of oxygen bubbles and its influence on current efficiency in micro-arc oxidation process of AZ91D magnesium alloy," Thin Solid Films, vol. 485, pp. 53-58, (2005).

Guo et al., "Growth of ceramic coatings on AZ91D magnesium alloys by micro-arc oxidation in aluminate-fluoride solutions and evalucation of corrosion resistance," Applied Surface Science, Col. 246, pp. 229-238, (2005).

Guo et al., "Investigation of corrosion behaviors of Mg-6Gd-3Y-0.4Zr alloy in NaCl aqueous solutions," Electrochimica Acta, vol. 52, pp. 2570-2579, (2007).

Guo et al., "Sol gel derived photocatalytic porous TiO2 thin films," Surface & Coatings Technology, vol. 198, pp. 24-29, (2005).

Gvd Corporation, "Nanocoatings for a New Era," pp. 1-3, [first downloaded 11/12/03].

Haag et al., "Polymer Therapeutics: Concepts and Applications," Angewandte Chemie, vol. 45, pp. 1198-1215, (2006).

Haberland et al., "Filling of micron-sized contact holes with copper by energetic cluster impact," Journal of Vacuum Science Technology a, vol. 12, No. 5, pp. 2925-2930, Sep./Oct. 1994.

Haery et al., "Drug-eluting stents: the beginning of the end of restenosis?," Cleveland Clinic Journal of Medicine, vol. 71, No. 10, pp. 815-824, (2004).

Hahn et al., "A novel approach for the formation of Mg(Oh)2/MgO nanowhiskers on magnesium: Rapid anodization in chloride containing solutions", Electrochemistry Communications, vol. 10, pp. 288-292, (2008).

Halme et al., "Spray Deposition and Compression of TiO2 Nanoparticle Films for Dye-Sensitized Solar Cells on Plastic Substrates," Solar Energy Materials & Solar Cells, vol. 90, pp. 887-899, (2006).

Hamley et al., "Nanostructure fabrication using block copolymers," Nanotechnology, vol. 14, pp. R39-R54, (2003).

Han et al., "Electron injection enhancement by diamond-like carbon film in organic electroluminescence devices," Thin Solid Films, vol. 420-421, pp. 190-194, (2002).

Han et al., "Pourous nanocrystalline titania films by plasma electrolytic oxidation," Surface and Coatings Technology, vol. 154, pp. 314-318, (2002).

Han et al., "Structure and in vitro bioactivity of titania-based films by micro-arc oxidation," Surface and Coatings Technology, vol. 168, pp. 249-258, (2003).

Han et al., "Synthesis of nanocrystalline titaniaa films by micro-arc oxidation," Materials Letters, vol. 56, pp. 744-747, (2002).

Hanley et al., "The growth and modification of materials via ion-surface processing," Surface Science, vol. 500, pp. 500-522, (2002).

Harris et al., "Fabrication of Perforated Thin Films with Helical and Chevron Pore Shapes," Electrochemical and Solid-State Letters, vol. 4, pp. C39-C42, (2004).

Harvard Nanopore, "Ion Beam Sculpting: Material Science - Fabricating Nanopores and Other Nanoscale Feature," pp. 1-5, [first downloaded Jul. 2, 2003], (http://www.mcb.harvard.edu.branton/projects-IonBeam/htm).

Hattori et al., "Photoreactivity of Sol-Gel TiO2 Films Formed on Soda-Lime Glass Substrates Effect of SiO2 Underlayer Containing Fluorine," Langmuir, vol. 15, pp. 5422-5425, (1999).

Hau et al., "Surface-chemistry technology for microfluidics," Journal of Micromechanics and Microengineering, vol. 13, pp. 272-278, (2003).

Hausleiter et al., "Prvention of restenosis by a novel drug-eluting stent system with a dose-adjustable, polymer-free, on-site stent coating," European Heart Journal, vol. 26, pp. 1475-1481, (2005).

He et al., "Electrochemical Fabrication of Metal Nanowires," Encyclopedia of Nanoscience and Nanotechnology, vol. X, pp. 1-18, (2003).

He et al., "Optical properties of diamond-like carbon synthesized by plasma immersion ion processing," Journal of Vacuum Science Technology, vol. B17, No. 2, pp. 822-827, Mar./Apr. 1999.

Heidenau et al., "Structured Porous Titania as a Coating for Implant Materials," Key Eng Mater. vol. 192-195, pp. 87-90, (2001).

Heinig et al., "Modeling and Simulation of Ion Beam Systhesis of Nanoclusters," 6 pp., [first downloaded Jan. 3, 2000], (http://www.fz-rossendorf.de/p1s/rois/Cms?p0Id=10960&pFunc=Print&pLang=de).

Helmersson et al., "Ionized physical vapor deposition (Ipvd): a review of technology and applications," Thin Solid Films, vol. 513, pp. 1-24, (2006).

Helmus et al. "Surface Analysis of a Series of Copolymers of L-Glutamic Acid and L-Leucine," Journal of Colloid and Interface Science, vol. 89, no. 2, pp. 567-570, (1982).

Helmus et al., "Plasma Interaction on Block Copolymers as Determined by Platelet Adhesion," Biomaterials: Interfacial Phenomena and Applications: Chapter 7, pp. 80-93, (1981).

Helmus et al., "The Effect of Surface Charge on Arterial Thrombosis," Journal of Biomedical Materials Research, vol. 18, pp. 165-183, (1984).

Hentze et al., "Porous polymers and resins for biotechnological and biomedical applications," Reviews in Molecular Biology, vol. 90, pp. 27-53, (2002).

Hoa et al., "Preparation of porous meterials with ordered hole structure," Advances in Colloid and Interface Science, vol. 121, pp. 9-23, (2006).

Hoffman, "Non-Fouling Surface Technologies," Journal of Biomaterials Science, Polymer Edition, vol. 10, No. 10, pp. 1011-1014, (1999).

Hoglund, "Controllable Degradation Product Migration From Biomedical Polyester-ethers," Kth Chemical Science and Engineering, Stockholm, pp. 1-52, May 24, 2007.

Holland et al., "Synthesis of Macroporous Minerals with Highly Ordered Three-Dimensional Arrays of Spheroidal Voids," Science, vol. 281, pp. 538-540, Jul. 24, 1998.

Hong et al., "The super-hydrophilicities of Bi-TiO2, V-TiO2, and Bi-V-TiO2 nano-sized particles and their benzene photodecompositions with H2O addition," Materials Letters, vol. 60, pp. 12961305, (2006).

Hopp et al., "Absorbing film assisted laser induced forward transfer of fungi (Trichoderma conidia)," Journal of Applied Physics, vol. 96, No. 6, pp. 3478-3481, Sep. 15, 2004.

Houbertz, "Laser interaction in sol-gel based materials - 3-D lithography for photonic applications," Applied Surface Science, vol. 247, pp. 504-512, (2005).

Houdayer et al., "Preparation of new antimony(0)/polyaniline nanocomposites by a one-pot solution phase method," Materials Letter, vol. 61, pp. 171-176, (2007).

Hrudey et al., "Organic Alq3 Nanostructures Fabricated with Glancing Angle Depostion," Vacuum Technology & Coating, pp. 1-6, May 2006.

Hsiao et al., "Soluble aromatic polyamides bearing asymmetrical diaryl ether groups," Polymer, vol. 45, pp. 7877-7885, (2004).

Hu et al., "Cyclic voltammetric deposition of hydrous ruthenium oxide for electrochemical capacitors: effects of codeposting iridium oxide," Electrochimica Acta, vol. 45, pp. 2684-2696, (2000).

Hu et al., "Voltammetric investigation of platinum oxides Ii. Efect of hydration on the reduction behavior," Electrochimica Acta, vol. 45, pp. 3063-3068, (2000).

Hiippauff et al., "Valency and Structure of Iridium in Anodic Iridium Oxide Films," Journal of Electrochemical Society, vol. 140, No. 3, pp. 598-602, Mar. 1993.

Hurley et al., "Nanopatterning of Alkynes on Hydrogen-Terminated Silicon Surfaces by Scanning Probe-Induced Cathodic Eletrografting," Journal of American Chemistry Society, vol. 125, pp. 11334-11339, (2003).

Hussain et al., "Atomic force microscope study of three-dimensional nanostructure sidewalls," Nanotechnology, vol. 18, pp. 1-8, (2007).

Ichinose et al., "A surface sol-gel process of TiO2 and other metal oxide films with molecular precision," Chem. Mater. vol. 9, pp. 1296-1298, (1997).

Ichinose et al., "Ultrathin composite films: an indispensable resource for nanotechnolo ," Riken Review, No. 37, pp. 34-37, Jul. 2001.

Ignatova et al., "Combination of Electrografting and Aton-Transfer Radical Polymerization for Making the Stainless Steel Surface Antibacterial and Protein Antiadhesive," Langmuir, vol. 22, pp. 255-262, (2006).

Imai et al., "Preparation of Porous Anatase Coatings from Sol-Gel-Derived Titanium Dioxide and Titanium Dioxide-Silica by Water-Vapor Exposure," Journal of American Ceramics Society, vol. 82, No. 9, pp. 2301-2304, (1999).

Inflow Dynamics starts "Lusty" Study, Company Press Release: First clinical trial with Niobium stents, (www.tctmd.com/industry-news/one.html?news_id=3364), 1 p., Jun. 25, 2002.

Inoue et al., "Corrosion rate of magnesium and its alloys in buffered chloride solutions," Corrosion Science, vol. 44, pp. 603-610, (2002).

Inovati, "Award Winning - Environmentally-Safe, High-Quality, Metal Spray Process," Press Release, pp. 1-6, (2002), (http://www.inovati.com/papers/Km-PressRelease.doc).

Inovati, "Inovati to Develop Green Metal Coating Technology" Press Release, 1 p., [first downloaded Sep. 1, 2005], (http://www.inovati.com/papers/bmdopr.html).

Inovati, "Low temperature, high-speed sprays make novel coatings," 1 pp., [first downloaded on Mar. 18, 2003], (http://www.inovati.com/papers/ampmar0 1 .html).

Introduction to the Metal Printing Process: Future manufacturing equipment of advanced materials and complex geometrical shapes, (www.mpp.no/intro/intro.htm), pp. 1-2, downloaded Mar. 18, 2002.

Irhayem et al., "Glucose Detection Based on Electrochemically Formed Ir Oxide Films," Journal of Electroanalytical Chemisty, vol. 538-539, pp. 153-164, (2002).

Irvine et al., "Nanoscale clustering of Rgd peptides at surfaces using Comb polymers. 1. Synthesis and characterization of Comb thin films, Biomacromolecules", vol. 2, No. 1, pp. 85-94, Spring 2001.

Irvine et al., "Nanoscale clustering of Rgd peptides at surfaces using comb polymers. 2. Surface segregation of comb polymers in polylactide," Biomacromolecules, vol. 2, No. 2, pp. 545-556, Summer 2001.

Ishizawa et al., "Characterization of thin hydroxyapatite layers formed on anodic titanium oxide films containing Ca and p. By hydrothermal treatment," Journal of Biomedical Materials Research, vol. 29, pp. 1071-1079, (1995).

Ishizawa et al., "Histomorphometric evaluacation of the thin hydroxyapatite layer formed through anodization followed by hydrothermal treatment," Journal of Biomedical Materials Research, vol. 35, pp. 199-206, (1997).

Isoflux Inc., "Isoflux specializes in vacuum coating equipment and coating process," http://www.isofluxinc.com/about.shtml, 1 p., Jul. 2009.

Iurhayem et al. "Glucose detection based on electrochemically formed Ir oxide films," Journal of Electroanalytical Chemistry, vol. 539-539, pp. 153-164, (2002).

Jensen et al., "Low-temperature preparation of nanocrystalline anatase films through a sol-gel rout," Journal of Sol-Gel Science and Technology, vol. 39, pp. 229-233, (2006).

Jewell et al., "Multilayered polyelectolyte films promote the direct and localized delivery of Dna to cells," Journal of Controlled Release, vol. 106, pp. 214-223, (2005).

Jmar Llc, "Collimated Plasma Lithography (Cpl)," 1 p., [first downloaded Jul. 2, 2003], (http://www.jmar.com/co451.html).

Johnson, "What's an Ionic Liquid?," the Electrochemical Society: Interface, pp. 38-41, Spring 2007.

Juodkazis et al., "Alternative view of anodic surface oxidation of nobel metals," Electrochimica Acta, vol. 51, pp. 6159-6164, (2006).

Kamei et al., "Hydrophobic drawings on hydrophilic surfaces of single crystalline titanium dioxide: surface wettability control by mechanochemical treatment," Surface Science Letters, vol. 463 pp. L609-L612, (2000).

Kanda et al., "Characterization of Hard Diamond-Like Carbon Films Formed by Ar Gas Cluster Ion Beam-Assisted Fullerene Deposition," Japanese Journal of Applied Physics, vol. 41, Part 1, No. 6B, pp. 4295-4298, Jun. 2002.

Kang et al., "Controlled drug release using nanoporous anodic aluminum oxide on stent," Thin Solid Films, vol. 515, pp. 5184-5187, (2007).

Kaplan, "Cold Gass Plasma and Silanes," Presented at the 4th International Symposium on Silanes and Other Coupling Agents, Jul. 11-13, 2003.

Karuppuchamy et al., "Cathodic Electrodeposition of Oxide Semiconductor Thin Films and their Application to Dye-Sensitized Solar Cells," Solid State Ionics, vol. 151, pp. 19-27, (2002).

Karuppuchamy et al., "Photoinduced Hydrophilicity of Titanium Dioxide Thin Films Prepared by Cathodic Electrode position," Vacuum, vol. 80, pp. 494-498, (2006).

Karuppuchamy et al., "Super-hydrophilic amorphous titanium dioxide thin film deposited by cathodic electrodeposition," Materials Chemisty and Physics, vol. 93, pp. 251-254, (2005).

Karuri et al., "Biological length scale topography enhances cell-substratum adhesion of human corneal epithelial cells," Journal of Cell Science, vol. 117, No. 15, pp. 3153-3164, (2004).

Kasemo et al., "Implant surfaces and interface processes," Adv. Dent. Res. vol. 13, pp. 8-20 Jun. 1999.

Kasemo, "Biological surface science," Surface Science, vol. 500, pp. 656-677, (2002).

Kato et al., "N-succinyl-chitosan as a drug carrier: water-insoluble and water-soluble conjugates," Biomaterials, vol. 25, pp. 907-915, (2004).

Katsumata et at., "Effect of Microstructure on Photoinduced Hydrophilicity of Transparent Anatase Thin Films," Surface Science, vol. 579, pp. 123-130, (2005).

Katz, "Developments in Medical Polymers for Biomaterials Applications," Medical Device Link, pp. 1-9, Jan. 2001, (http://www.devicelink.com/mddi/archive/01/01/003.html).

Kean et al. "The Analysis of Coatings Produced by Accelerated Nanoparticles," Mantis Deposition Ltd., Presentaction at Nsti Nano Tech 2006, Boston, May 7th-11th, pp. 1-4, 2006.

Kesapragada et al., "Two-component nanopillar arrays grown by Glancing Angle Deposition," Thin Solid Films, vol. 494, pp. 234-239, (2006).

Kesler et al., "Enhanced Strength of Endothelial Attachment on Polyester Elastomer and Polytetrafluoroethylene graft Surfaces with Fibronectin Substrate," Journal of Vascular Surgery, vol. 3, No. 1, pp. 58-64, (1986).

Kesting, "Synthetic Polymeric Membranes - a Structural Perspective", Chapters 6-7, pp. 225-286, Oct. 1985.

Kickelbick, "Concepts for the incorporation of inorganic building blocks into organic polymers on a nanoscale," Progress in Polymer Science, vol. 28, pp. 81-114, (2003).

Kidambi et al., "Selective Depositions on Polyelectrolyte Multilayers: Self-Assembled Monolayers on m-dPEG Acid as Molecular Template," Journal of the American Chemistry Society, vol. 82, No. 9, pp. 4697-4703, (2004).

Kilian et al., "Plasma transglutaminase factor Xiii induces microvessel ingrowth into biodegradable hydroxyapatite implants in rats," Biomaterials, vol. 26, pp. 1819-1827, (2005).

Kim et al. "Porous Zr02 bone scaffold coated with hydroxyapatite with fluorapatite intermediate layer," Biomaterials, vol. 24, pp. 3277-3284, (2003).

Kim et al., "Adhesion of Rf bias-sputtered Cr thin films onto photosensitivepolyimide substrates," IEEE, International Symposium on Eelectrical Materials and Pakaging, pp. 202-207, (2001).

Kim et al., "Fabrication of Wc-Co coatings by cold spray deposition," Surface & Coatings Technology, vol. 191, pp. 335-340, (2005).

Kim et al., "Hollow Silica Spheres of Controlled Size and Porosity by Sol-Gel Processing," Journal of Americal Ceramic Society, vol. 74, Nol. 8, pp. 1987-1992, (1991).

Kim et al., "Proton conducting polydimethylsiloxane/metal oxide hybrid membranes added with phosphotungstic acid(Ii)," Electrochimica Acta, vol. 49, pp. 3429-3433, (2004).

Kim et al., "Fabrication and Characterization of TiO2 Thin Film Prepared by a Layer-By-Layer Self-Assembly Method," Thin Solid Films, vol. 499, pp. 83-89, (2006).

Kitagawa et al., "Near-Edge X-Ray Absorption Fine Structure Study for Optimization of Hard Diamond-Like Carbon Film Formation with Ar Cluster Ion Beam," Japanese Journal of Applied Physics, vol. 42, pp. 3971-3975, (2003).

Kitagawa et al., Optimum Incident Angle of Ar Cluster Ion Beam for Superhard Carbon Film Deposition," Japanese Journal of Applied Physics", vol. 43, No. 6B, pp. 3955-3958, (2004).

Kittaka et al., "The Structure of Water Monolayers on a Hydroxylated Chromium Oxide Surface," Adsorption, vol. 11, pp. 103-107, (2005).

Kleinertz et al., "Lusty Studie: Lunar Stf Study," PowerPoint presentation, pp. 1-24, Sep. 4, 2004.

Kleisner et al., "A system based on metal alkyl species that forms chemically bound organic overlays on hydroxylated planar surfaces," Thin Solid Films, vol. 381, pp. 10-14, (2001).

Kogure et al., "Microstructure of nemalite, fibrous iron-bearing brucite", Mineralogical Journal, vol. 20, No. 3, pp. 127-133, Jul. 1998.

Kohli et al., "Arrays of lipid bilayers and liposomes on patterned polyelectrolyte templates," Journal of Colloid and Interface Science, vol. 301, pp. 461-469, (2006).

Kokubo et al., "Novel bioactive materials with different mechanical properties," Biomaterials, vol. 24, pp. 2161-2175, (2003).

Kommireddy et al., "Layer-by-Layer Assembly of TiO2 Nanoparticles for Stable Hydrophilic Biocompatible Coatings" Journal of Nanoscience and Nanotechnology, vol. 5, pp. 1081-1087, (2005).

Kondyurin et al., "Plasma Immersion ion implantation of polyethylene," Vacuum, vol. 64, pp. 105-111, (2002).

Kong et al., "Polyelectrolyte-functionalized multiwalled carbon nanotubes: preparation, characterization and layer-by-layer self-assembly," Polymer, vol. 46, pp. 2472-2485, (2005).

Konig et al., "Nanoprocessing with nanojoule near-infrared femtosecond laser pulses," Medical Laser Application, vol. 20, pp. 169-184, (2005).

Konishi et al., "Morphology Control of Dy-Ni Alloy Films by Electrochemical Displantation," Electrochemical and Solid-State Letters, vol. 5, No. 12, pp. B37-B39, (2002).

Koo et al., "Co-regulation of cell adhesion by nanoscale Rgd organization and mechanical stimulus," Journal of Cellular Science, vol. 115, Part 7, pp. 1423-1433, Apr. 1, 2002.

Kopanski et al., "Scanning Kelvin Force Microscopy for Characterizing Nanostructures in Atmosphere," Characterization and Metrology for Nanoelectronics: 2007 International Conference on Frontiers of Characterization and Metrology. American Institute of Physics Conference Proceedings, vol. 931, pp. 530-534, Septem 26, 2007.

Kostov et al., "Two Dimensional Computer Simulation of Plasma Immersion Ion Implantation," Brazilian Journal of Physics, vol. 34, No. 4B, pp. 1689-1695, Dec. 2004.

Kotz et al., "Xps Studies of Oxygen Evolution on Ruand Ru02 Anodes," Journal of Electrochemical Society: Electrochemical Science and Technology, pp. 825-829, Apr. 1983.

Kowalski et al., "Corrosion protection of steel by bi-layered polypyrrole doped with molybdophosphate and naphthalenedisulfonate anions," Corrosion Science, Vo. 49, pp. 16351644, ( 2007).

Kraft et al., "Thin films from fast clusters: golden TiN layers on a room temperature substrate" Surface and Coatings Technology 158-159, pp. 131-135, (2002).

Krumeich et al., "HyFraSurf-Advanced Surface Technology for Superior Electrode Performance," European Cells and Materials, vol. 1, Suppl. 1, p. 43, (2001).

Kumar et al., "Influence of electric field type on the assembly of single walled carbon nanotubes," Chemical Physics Letters, vol. 383, pp. 235-239, (2004).

Kumar et al., "Polyanhydrides: an overview," Advanced Drug Delivery Reviews, vol. 54, pp. 889-910, (2002).

Kunitake et al., "Molecular imprinting in ultrathin titania gel films via surface sol-gel process," Analytica Chimica Acta, vol. 504, pp. 1-6, (2004).

Kurth et al., "Multilayers on Solid Planar Substrates: From Structure to Function," Multilayer Thin Films: Sequential Assembly of Nanocomposite Materials, Chapter 14, pp. 393-426, Mar. 7, 2003.

Kutsenko et al., "Structural changes in Mg alloy induced by plasma immersion ion implantation of Ag," Acta Materialia, vol. 52, pp. 4329-4335, (2004).

Kutz, "Biomaterials to Promote Tissue Regeneration," in Standard Handbook of Biomedical Engineering and Design, ISBN 0-07-135637-1, pp. 16.13-16.29, (2003).

Kvastek et al., "Electrochemical properties of hydrous rithenium oxide films formed and measured at different potentials," Journal of Electroanalytical Chemistry, vol. 511, pp. 65-78, (2001).

Lakard et al., "Adhesion and proliferation of cells on new polymers modified biomaterials," Bioelectrochemistry, vol. 62, pp. 19-27, (2004).

Lakatos-Varsanyi et al., "Cyclic voltammetry measurements of different single-, bi- and multilayer TiN and single layer CrN coatings on low-carbon-steel substrates," Corrosion Science, vol. 41, pp. 1585-1598, (1999).

Lamaka et al., "TiOx self-assembled networks prepared by templating approach as nanostructured reservoirs for self-healing anticorrosion pre-treatments," Electrochemistry Comunications, vol. 8, pp. 421-428, (2006).

Lamer et al., "The Challenge of Plasma Processing - Its Diversity," Presented at the Asm Materials and Processes for Medical Devices Conference, Aug. 25-27, 2004.

Laser-Induced Forward Transfer (Lift): Paul Scherrer Institut, (http://materials.web.psi.ch/Research/Thin_Films/Methods/Lift.htm), pp. 1-2, downloaded Dec. 7, 2006.

Lau et al., "Hot-wire chemical vapor deposition (Hwcvd) of fluorocarbon and organosilicon thin films," Thin Solid Films, vol. 395, pp. 288-291, (2001).

LaVan et al., "Small-scale systems for in vivo drug delivery, Nature Biotechnology", vol. 21, No. 10, pp. 1184-1191, Oct. 2003.

Leary-Swan et al., "Fabrication and evaluation of nanoporous alumina membranes for osteoblast culture," Journal of Biomedical Materials Research: Part a, vol. 72A, pp. 288-295, (2005).

Lee et al., "A Template-Based Electrochemical Method for the Synthesis of Multisegmented Metallic Nanotubes," Angewandte Chemie, vol. 44, pp. 6050-6054, (2005).

Lee et al., "Biocompatibility and Charge Injection Property of Iridium Film Formed by Ion Beam Assisted Deposition," Biomaterials, vol. 24, pp. 2225-2231, (2003).

Lee et al., "Structural characterization of porous low-k thin films prepared by different techniques using x-ray porosimetry," Journal of Applied Physics, vol. 95, No. 5, Mar. 1, 2004.

Lee et al., "A study on electrophoretic deposition of Ni nanoparticles on pitted Ni alloy 600 with surface fractality", Journal of Colloid and Interface Science, vol. 308, pp. 413-420, (2007).

Lefaux et al., "Polyelectrolyte Spin Assembly: Influence of Ionic Strenght on the Growth of Multilayered Thin Films," Journal of Polymer Science Part B: Polymer Physics, vol. 42, pp. 3654-3666, (2004).

Lei et al., "Fabrication of Highly Ordered Nanoparticle Arrays Using Thin Porous Alumina Masks," Advanced Materials for Micro- and Nano-Systems (Ammns), pp. 1-6, Jan. 2001.

Leng et al., "Mechanical properties and platelet adhesion behavior of diamond-like carbon films synthesized by pulsed vacuum arc plasma deposition," Surface Science, vol. 531, pp. 177-184, (2003).

Lenza et al., "In vitro release kinetics of proteins from bioactive foams," Journal of Biomedical Materials Research: a, vol. 67, No. 1, pp. 121-129, Oct. 2003.

Leoni et al., "Characterization of Nanoporous Membranes for immunoisolation: Diffusion Properties and Tissue Effects," Biomedical Microdevices, vol. 4, No. 2, pp. 131-139, (2002).

Leoni et al., "Nanoporous Platforms for Cellular Sensing and Delivery," Sensors, 51(2), pp. 111-120, (2002).

Leung et al., "Fabrication of photonic band gap crystal using microtransfer molded templates," Journal of Applied Physics, vol. 93, No. 10, pp. 5866-5870, May 15, 2003.

Lewis et al., "Silicon nonopillars formed with gold colloidal partical masking," Journal of Vacuum Science Technology B, vol. 16, No. 6, pp. 2938-2941, Nov/Dec 1998.

Li et al., "A simple approach to fabricate amorphous silicon pattern on single crystal silicon," Tribology International, vol. 40, pp. 360-364, (2007).

Li et al., "Bioactive Hydroxyapatite Composite Coating Prepared by Sol-Gel Process," Journal of Sol-Gel Science and Technology, vol. 7, pp. 27-34, (1996).

Li et al., "Fabrication and Microstructuring of Hexagonally Ordered Two-Dimensional Nanopore Arrays in Anodic Alumina," Advanced Materials, vol. 11, pp. 483-487, (1999).

Li et al., "Hexagonal pore arrays with a 50-420 nm interpore distance formed by self-organization in anodic alumina," Journal of Applied Physics, vol. 84, No. 11, pp. 6023-6026, Dec. 1, 1998.

Li et al., "Improved biological performance of Ti implants due to surface modification by micro-arc oxidation," Biomaterials, vol. 25, pp. 2867-2875, (2004).

Li et al., "On the growth of highly ordered pores in anodized aluminum oxide," Chem. Mater., vol. 10, pp. 2470-2480, (1999).

Li et al., "pH-compensation effect of bioactive inorganic fillers on the degradation of Plga," Composites Science and Technology, vol. 65, pp. 2226-2232, (2005).

Li et al., "Polycrystalline nanopore arrays with haxagonal ordering on aluminum," Journal of Vacuum Science Technology: a, vol. 17, pp. 1428-1431, (1999).

Li et al., "A novel method for preparing surface-modified Mg(Oh)2 nanocrystallines," Materials Science and Engineering a, 452-453, pp. 302-305, (2007).

Li, "Poly(L-glutamic acid)-anticancer drug conjugates," Advanced Drug Delivery Reviews, vol. 54, pp. 695-713, (2002).

Liaw et al., "Process Monitoring of Plasma Electrolytic Oxidation," presented at the 16th World Conference on Nondestructive Testing, Montreal, Canada, pp. 1-7, Aug. 30-Sep. 3, 2004.

Liebling et al., "Optical Properties of Fibrous Brucite from Asbestos, Quebec", American Mineralogist, vol. 57, pp. 857-864, (1972).

Lim et al., "Systematic variation in osteoblast adhesion and phenotype with substratum surface characteristics," Journal of Biomedical Materials and Research, vol. 68A, No. 3, pp. 504-511, (2004).

Lim et al., "Uv-Driven Reversible Switching of a Roselike Vanadium Oxide Film between Superhydrophobicity and Superhydrophilicity," Journal of American Chemical Society, vol. 129, pp. 4126-4129, Mar. 15, 2007.

Lin et al., "Pwa-doped Peg/Si02 proton-conducting hybrid membranes for fuel cell applications," Journal of Membrane Science, vol. 254, pp. 197-205, (2005).

Lindstrom et al., "A New Method for Manufacturing Nanostructured Electrodes on Glass Substrates," Solar Energy Materials & Solar Cells, vol. 73, pp. 91-101 (2002).

Lippert et al., "Chemical and Spectroscopic Aspects of Polymer Ablation: Special Features and Novel Directions," Chemical Reviews, vol. 103, pp. 453-485, (2003).

Liu et al., "A metal plasma source ion implantation and deposition system," American Institute of Physics, Review of Scientific Instruments, vol. 70, No. 3, pp. 1816-1820, Mar. 1999.

Liu et al., "Electrodeposition of Polypyrrole Films on Aluminum from Tartrate Aqueous Solution," Journal of Brazilian Chemical Society, vol. 18, No. 1, pp. 143-152, (2007).

Liu et al., "Surface modification of titanium, titanium alloys, and related materials for biomedical applications," Materials Science and Engineering R, vol. 47, pp. 49-121, (2004).

Lu et al., "Fabricating Conducting Polymer Electrochromic Devices Using Ionic Liquids," Journal of the Electrochemical Society, vol. 151, No. 2, pp. H33-H39, (2004).

Lu et al., "Micro and nano-fabrication of biodegradable polymers for drug delivery," Advanced Drug Delivery Reviews, vol. 56, pp. 1621-1633, (2004).

Lv et al., "Controlled growth of three morphological structures of magnesium hydroxide nanoparticles by wet precipitation method," Journal of Crystal Growth, vol. 267, pp. 676-684, (2004).

Lv et al., "Controlled synthesis of magnesium hydroxide nanoparticles with different morphological structures and related properties in flame retardant ethyolene-vinyl acetate blends", Nanotechnology, vol. 15, pp. 1576-1581, (2004).

Lv et al., "In situ synthesis of nanolamellas of hydrophobic magnesium hydroxide", Colloids and Surfaces a: Physicochemical and Engineering Aspects, vol. 296, pp. 97-103, (2007).

Maeda et al., "Effect of Silica Addition on Crystallinity and Photo-Induced Hydrophilicity of Titania-Silica Mixed Films Prepared by Sol-Gel Process," Thin Solid Films, vol. 483, pp. 102106, (2005).

Maehara et al., "Buildup of Multilayer Structures of Organic-Inorganic Hybrid Ultra Thin Films by Wet Process," Thin Solid Films, vol. 438-439, pp. 65-69, (2003).

Maheshwari et al., "Cell adhesion and motility depend on nanoscale Rgd clustering," Journal of Cell Science, vol. 113, Part 10, pp. 1677-1686, May 2000.

Maitz et al., "Blood Compatibility of Titanium Oxides with Various Crystal Structure and Element Doping," Journal of Biomaterials Applications, vol. 17, pp. 303-319, Apr. 2003.

Manna et al., "Microstructural Evalution of Laser Surface Alloying of Titanium with Iridium," Scripta Materialia, vol. 37, No. 5, pp. 561-568, (1997).

Manoharan et al., "Ordered macroporous rutile titanium dioxide by emulsion templating," Proceedings of Spie, vol. 3937, pp. 44-50, (2000).

Mantis Deposition Ltd., "Nanocluster Deposition," Thame, Oxforshire, United Kingdom, pp. 1-2, [downloaded on Feb. 2, 2007], (http://www.mantisdeposition.corn/nanocluster.html).

Martin et al., "Microfabricated Drug Delivery Systems: Concepts to Improve Clinical Benefit," Biomedical Microdevices, vol. 3, No. 2, pp. 97-107, Jun. 2001.

Martin, "Pulsed Laser Deposition and Plasma Plume Investigations," Andor Technology, Ltd. Pages 1-3, (2003).

Masuda et al., "Highly ordered nanochannel-array architecture in anodic alumina," Applied Physics Letters, vol. 71, pp. 2770-2772, (1997).

MatijeviO, "Colloid Chemical Aspects of Corrosion of Metals", Pure & Applied Chemisty, vol. 52, pp. 1179-1193, (1980).

Mattox, "Introduction: Physical Vapor Deposition (Pvd) Processes," Vacuum Technology & Coating, pp. 60-63, Jul. 2002.

Mattox, "The History of Vacuum Coating Technology: Part V," Vacuum Technology & Coating, pp. 32-37, Oct. 2002.

Mattox, "The History of Vacuum Coating Technology: Part Vi," Vacuum Technology & Coating, pp. 52-59, Oct. 2002.

Mauritz Group Homepage, "Sol-Gel Chemistry and Technology," (htty://www.psrc.usin.edu/mauritz/solgel.html), pp. 1-10, (downloaded [2006]).

McGuigan et al., "The influence of biomaterials on endothelial cell thrombogenicity," Biomaterials, vol. 28, pp. 2547-2571, (2007).

McNally et at., "Cathodic Electrodeposition of Cobalt Oxide Films Using Polyelectrolytes," Materials Chemistry and Physics, vol. 91, pp. 391-398, (2005).

Meijer et al., "Laser Machining by short and ultrashort pulses, state of the art and new opportunities in the age of the photons," Annals of Cirp 2002: Manufacturing Technology, vol. 51, No. 2, pp., 531-550, (2002).

Meletis et al., "Electrolytic plasma processing for cleaning and metal-coating of steel surfaces," Surface and Coatings Technology, vol. 150, pp. 246-256, (2002).

Merriam-Webster's Dictionary Website: for definition of Strut, 1 p.,[first cited Jul. 21, 2010], (http://www.merriam-webster.com/dictionary/strut).

MicroFab Technologies Inc. "MicroFab: Biomedical Applications - Stents," pp. 1-4, [first downloaded Mar. 23, 2007], (http://www.microfab.com/technology/biomedical/Stents.html).

Mikhaylova et al., "Nanowire formation by electrodeposition in modified nanoporous polycrystalline anodic alumina templates," Mat. Res. Soc. Symp. Proc., vol. 704, pp. w6.34.1-W6.34.6, (2002).

Miller et al., "Endothelial and vascular smooth muscle cell function on poly(lactic-co-glycolic acid) with nano-structured surface features," Biomaterials, vol. 25, No. 1, pp. 53-61, (2004).

Miller et al., "Mechanism(s) of increased vascular cell adhesion on nanostructured poly(lactic-coglycolic acid) films," Journal of Biomedical Materials Research a, vol. 73, No. 4, pp. 476-484, (2005).

Miv Therapeutics, "Hydroxyapatite Coating," pp. 1-4, [first downloaded Jun. 25, 2003], (http://www.mivtherapeutics.com/technology/hap/).

Mobedi et al., "Studying the Degradation of Poly(L-lactide) in Presence of Magnesium Hydroxide", Iranian Polymer Journal, vol. 15, No. 1, pp. 31-39, (2006).

Mu et al., "A novel controlled release formulation for the anticancer drug paclitaxel (Taxol): Plga nanoparticles containing vitamin E Tpgs," Journal of Controlled Release, vol. 86, pp. 33-48, (2003).

Mu et al., "Vitamin E Tpgs used as emulsifier in the solvent evaporation/extraction technique for fabrication of polymeric nanospheres 0 for controlled release of paclitaxel (Taxol)", Journal of Controlled Release, vol. 80, pp. 129-144, (2002).

Muller et al., "Solid lipid nanoparticles (Sln) for controlled drug delivery: a review of the state of the art," European Journal of Pharmaceutics and Biopharmaceutics, vol. 50, pp. 161-177, (2000).

Munchow et al., "Poly[(oligoethylene glycol) Dihydroxytitanate] as Organic-Inorganic Polymer-Electrolytes," Electrochimica Acta, vol. 45, pp. 1211-1221, (2000).

Murray et al., "Electrosynthesis of novel photochemically active inherently conducting polymers using an ionic liquid electrolyte," Electrochimica Acta, vol. 51, pp. 2471-2476, (2006).

Naganuma et al., "Preparation of Sol-Gel Derived Titanium Oxide Thin Films Using Vacuum Ultraviolet irradiation with a Xenon Excimer Lamp," Japanese Journal of Applied Physics, vol. 43, No. 9A, pp. 6315-6318, (2004).

Nair et al., "Biodegradable polymers as biomaterials", Progress in Polymer Science, vol. 32, pp. 732-798, (2007).

Nakajima et al., "Effect of Vacuum Ultraviolet Light Illumination on the Crystallization of Sol-GelDerived Titanium Dioxide Precursor Films," Surface & Coatings Technology, vol. 192, pp. 112116, (2005).

Nakayama et al., "Fabrication of drug-eluting covered stents with micropores and differential coating of heparin and FK506," Cardiovascular Radiation Medicine, vol. 4, pp. 77-82, (2003).

NanoBiotech News, vol. 2, No. 26, pp. 1-9, Jun. 30, 2004.

Nanoparticle coatings: Application note, "Antimicrobial Coatings," Mantis Deposition Ltd, pp. 1-2, (2006).

Nanu, "Nanostructured Ti02-CuInS2 based solar cells," Symposium D, Thin Film and Nano-Structured Materials for Photovoltaics, E-Mrs Spring Meeting 2003, pp. 1-2, Jun. 10-13, 2003.

Nasa Glenn Research Center, "Fast Three-Dimensional Method of Modeling Atomic Oxygen Undercutting of Protected Polymers," pp. 1-6, [first downloaded on Jul. 3, 2003], (http://www.grc.nasa.gov/Www/epbranch/suurtxt/surfaceabs.htm).

Neves et al., "The morphology, mechanical properties and ageing behavior of porous injection molded starch-based blends for tissue engineering scafolding," Materials Science and Engineering, vol. C25, pp. 195-200, (2005).

Newman et al., "Alloy Corrosion," Mrs Bulletin, pp. 24-28, Jul. 1999.

Ngaruiya et al., "Structure formation upon reactive direct current magnetron sputtering of transition metal oxide films," Applied Physics Letters, vol. 85, No. 5, pp. 748-750, Aug. 2, 2004.

Ngaruiya et al., "The reactive Dc-Magnetron Sputtering Process," , pages 1-5, (circa 2004).

Nicoll et al., "In vitro release kinetics of biologically active transforming growth factor-beta 1 from a novel porous glass carrier," Biomaterials, vol. 18, Issue 12, pp. 853-859, (1997).

Nicoll et al., "Nanotechnology and Biomaterials - Drugs, Drug Delivery Systems, Quantum Dots and Disease Treatment," Azom.com, pp. 1-5, [first downloaded 3/22/04], (http://www.azom.com/details.asp?ArticleID=1853).

Nie et al., "Deposition of layered bioceramic hydroxyapatite/Ti02 coatings on titanium alloys using a hybrid technique of micro-arc oxidation and electrophoresis," Surface Coatings Technology, vol. 125, pp. 407-414, (2000).

Nishio et al., "Preparation and properties of electrochromic iridium oxide thin film by sol-gel process," Thin Solid Films, vol. 350, pp. 96-100, (1999).

Noguera et al., "3D fine scale ceramic components formed by ink-jet prototyping process," Journal of the European Ceramic Society, vol. 25, pp. 2055-2059, (2005).

O'Brien et al., "Passivation of Nitinol Wire for Vascular Implants-A Demonstration of the Benefits," Biomaterials, vol. 23, pp. 1739-1748, (2002).

Oh et al., "Microstructural characterization of biomedical titanium oxide film fabricated by electrochemical method," Surface & Coatings Technology, vol. 198, pp. 247-252, (2005).

Orloff et al., "Biodegradable implant strategies for inhibition of restenosis," Advanced Drug Delivery Reviews, vol. 24, pp. 3-9, (1997).

Oxford Applied Research, "Nanocluster Deposition Systems - Nanodep60," 1 p., [first downloaded Nov. 3, 2006], (http://www.oaresearch.co.uk.nanodep60.htm).

Paik et al., "Micromachining of mesoporous oxide films for microelectromechanical system structures," Journal of Materials Research, vol. 17, pp. 2121-2129, (2002).

Palasis et al., "Analysis of Adenoviral Transport Mechanisms in the Vessel Wall and Optimization of Gene Transfer Using Local Delivery Catheters," Human Gene Therapy, vol. 11, pp. 237-246, Jan. 20, 2000.

Palasis et al., "Site-Specific Drug Delivery from Hydrogel Coated Angioplasty Catheters," Proceedings of the International Symposium on Controlled Release: Bioactive Materials, vol. 24, pp. 825-826, (1997).

Palmaz et al., "Influence of surface topography on endothelialization of intravascular metallic material," Journal of Vascular and Interventional Radiology, vol. 10, No. 4, pp. 439-444, (1999).

Pang et al., "Electrodeposition of composite hydroxyapatite-chitosan films," Materials Chemistry and Physics, vol. 94, pp. 245-251, (2005).

Pang et al., "Electropolymerization of high quality electrochromic poly(3-alkyl-thiophene)s via a room termperature ionic liquid," Electrochimica Acta, vol. 52, pp. 6172-6177, (2007).

Park et al., "Multilayer Transfer Printing for Polyelectrolyte Multilayer Patterning. Direct Transfer of Layer-by-Layer Assembled Micropatterned Thin Films," Advanced Materials, vol. 16, No. 6, pp. 520-525, Mar. 18, 2004.

Park et al., "Novel Phenylethynyl Imide Silanes as Coupling Agents for Titanium Alloy," the 22nd Annual Meeting of the Adhesion Society, pp. 1-5, Feb. 21-24, 1999.

Park et al., "Cathodic electrodeposition of Ru02 thin films from Ru(Iii)C13 solution", Materials Chemistry and Physics, vol. 87, pp. 59-66, (2004).

Park et al., "Microstructural change and precipitation hardeningin melt-spun Mg-X-Ca alloys," Science and Technology of Advanced Materials, vol. 2, pp. 73-78, (2001).

Pathan et al., "A chemical route to room-temperature synthesis of nanocrystalline TiO2 thin films," Applied Surface Science, vol. 246, pp. 72-76, (2005).

Pelletier et al., "Plasma-based ion implantation and deposition: a review for physics, technology, and applications," Lawrence Berkeley and National Laboratory, pp. 1-68, May 16, 2005.

Peng et al., "Role of polymers in improving the results of stenting in coronary arteries," Biomaterials, vol. 17, No. 7, pp. 658-694 (1996).

Perlman et al., "Evidence for rapid onset of apoptosis in medial smooth muscle cells after balloon injury," Circulation, vol. 95, No. 4, pp. 981-987, Feb. 18, 1997.

Pharmaceutical Science Technology, Chapter 6: Electropolymerization, pp. 24-28, (2007).

Piazza et al., "Protective diamond-like carbon coatings for future optical storage disks," Diamond & Related Materials, vol. 14, pp. 994-999, (2005).

Pitt et al., "Attachment of hyaluronan to metallic surfaces," Journal of Biomedical Materials Research, vol. 68A, pp. 95-106, (2004).

Polygenetics, "Advanced Drug Delivery," [first downloaded on May 4, 2007], 5 pp., (http://www.polygenetics.com/drug_delivery.htm).

Ponte et al., "Porosity determination of nickel coatings on copper by anodic voltammetry," Journal of Applied Electrochemistry, vol. 32, pp. 641-646, (2002).

Prior Clinicals, Boston Scientific memo, pp. 1-2, (more than a year prior to May 23, 2007).

Prokopowicz et al., "Synthesis and Application of Doxorubicin-Loaded Silica Gels as Solid Materials for Spectral Analysis," Talanta, vol. 65, pp. 663-671, (2005).

Prokopowicz et al., "Utilization of Standards Generated in the Process of Thermal Decomposition Chemically Modified Silica Gel or a Single Point Calibration of a Gc/Fid System," Talanta, vol. 44, pp. 1551-1561, (1997).

Pulsed Laser Deposition, (http://www.physandtech.net), pp. 1-7, Apr. 28, 2001.

Pvd Materials - Materials Available for Physical Vapour Deposition (Pvd) from Williams Advanced Materials. (www.azom.com), pp. 1-8, [first downloaded Apr. 28, 2006].

Qasem et al., "Kinetics of Paclitaxel 2'-N-Methylpyridinium Mesylate Decomposition," Aaps PharmaSciTech, vol. 4, No. 2, Article 21, pp. 1-8, (2003).

Qian et al., "Preparation, characterization and enzyme inhibition of methylmethacrylate copolymer nanoparticles with different hydrophilic polymeric chains," European Polyer Journal, vol. 42, pp. 1653-1661, (2006).

Qiang et al., "Hard coatings (TiN, TizAll-In) deposited at room temperature by energetic cluster impact," Surface and Coatings Technology, 100-101, pp. 27-32, (1998).

Qiu et al., "Self-assembled growth of Mg0 nanosheet arrays via a micro-arc oxidations technique," Applied Surface Science vol. 253, pp. 3987-3990, (2007).

Radin et al., "Biocompatible and Resorbable Silica Xerogel as a Long-Term Controlled Release Carrier of Vancomycin," Orthopaedic Research Society, 47th Annual Meeting, Feb. 25-28, 2001, San Francisco, Ca.

Radin et al., "Silica sol-gel for the controlled release of antibiotics. I. Synthesis, characterization, and in vitro release," Journal of Biomedical Materials Research, vol. 27, No. 2, pp. 313-320, Nov. 2001.

Radin, et al., "In vitro bioactivity and degradation behavior of silica xerogels intended as controlled release materials," Biomaterials. vol. 23, No. 15, pp. 3113-3122, Aug. 2002.

Radtchenko et al., "A Novel Method for Encapsulation of Poorly Water-Soluble Drugs: precipitation in Polyelectrolyte multilayer shells", International Journal of Pharmaceutics, vol. 242, pp. 219223, (2002).

Razzacki et al., "Integrated microsystems for controlled drug delivery," Advanced Drug Delivery Reviews, vol. 56, pp. 185-198, (2004).

Rees et al., "Glycoproteins in the Recognition of Substratum by Cultured Fibroblasts," Symposia of the Society for Experimental Biology: Cell-Cell Recognition, No. 32, pp. 241-260 (1978).

Reyna-Gonzales et al., "Influence of the acidity level on the electropolymerization of Nvinylcarbazole: Electrochemical study and characterization of poly(3,6-N-vinylcarbazole)," Polymer, vol. 47, pp. 6664-6672, (2006).

Rice, "Limitations of pore-stress concentrations on the mechanical properties of porous materials," Journal of Material Science, vol. 32, pp. 4731-4736, (1997).

Ristoscu, "Thin Films and Nanostructured Materials." pp. 1-2, [first downloaded Jul. 3, 2003], (http://www..fisica.unile.it/radiazioni/ThinY020films%20and%20nanostmctured%20materi als.htm).

Robbie et al., "Advanced techniques for glancing angle deposition," Journal of Vacuum Science and Technology B, vol. 16, No. 3, pp. 1115-1122, (May/Jun. 1998).

Robbie et al., "Sculptured thin films and glancing angle deposition: Growth mechanics and applications," Journal of Vacuum Science Technology: a., vol. 15, pp. 1460-1465, (1997).

Roder et al., "Tuning the microstructure of pulsed laser deposited polymer-metal nanocomposites," Applied Physics a. vol. 85, pp. 15-20 (2006).

Rosen et al., "Fibrous Capsule Formation and Fibroblast Interactions at Charged Hydrogel Interfaces," Hydrogels or Medical and Related Applications, Chapter 24, pp. 329-343, Jun. 1, 1976.

Rossi et al., "Pulsed Power Modulators for Surface Treatment by Plasma Immersion Ion Impantation," Brazilian Journal of Physics, vol. 34, No. 4B, pp. 1565-1571, Dec. 2004.

Routkevitch, "Nano- and Microfabrication with Anodic Alumina: a Route to Nanodevices," Foresight Institute 9th Conference on Molecular Nanotechnology, pp. 1-20, Nov. 8-11, 2001, Santa Clara, Ca.

Ryu et al., "Biomimetic apatite induction on Ca-containing titania," Current Applied Physics, vol. 5, pp. 512-515, (2005).

Santos et al., "Si-Ca-p. xerogels and bone morphogenetic protein act synergistically on rat stromal marrow cell differentiation in vitro," Journal of Biomedical Materials Research, vol. 41, No. 1, pp. 87-94, Jul. 1998.

Santos et al., "Sol-Gel Derived Carrier for the Controlled Release of Proteins," Biomaterials, vol. 20, pp. 1695-1700, (1999).

Sardella et al., "Plasma-Aided Micro- and Nanopatterning Processes for Biomedical Applications," Plasma Processes and Polymers, vol. 3, pp. 456-469, (2006).

Sasahara et al., "Macroporous and nanosized ceramic films prepared by modified sol-gel methods with Pmma microsphere templates," Journal of the European Ceramic Society, vol. 24, pp. 1961-1967, (2004).

Sawitowski, "Nanoporous alumina for implant coating - a novel approach towards local therapy," NanoMed 3rd Workshop, Medical Applications of Nanotechnology, Berlin, 1 p., Feb. 17-18, 2003.

Sawyer et al., "The Role of Electrochemical Surface Properties in Thrombosis at Vascular Interfaces: Cumulative Experience of Studies in Animals and Man," Bulletin of the New York Academy of Medicine, Second Series, vol. 48, No. 2, pp. 235-256, (1972).

Sawyer, "Electrode-Biologic Tissue Interreactions at Interfaces - a Review;" Biomat. Med. Dev. Art. Org., 12(3-4), pp. 161-196 (1984).

Schetsky, "Shape Memory Alloys", Encyclopedia of Chemical Technology (3rd ed.), John Wiley & Sons, vol. 20, pp. 726-736, (1982).

Schlottig et al., "Characterization of nanoscale metal structures obtained by template synthesis," Fresenius' Journal of Analytical Chemistry, vol. 361, pp. 684-686, (1998).

Schneider, "Laser Cladding with Powder: Effect of some machining parameters on clad properties," Doctoral Thesis - University of Twente, the Netherlands, pp. 1-176, Isbn 9036510988, Mar. 1998.

Schnitzler et al., "Organic/Inorganic Hybrid Materials Formed From TiO2 Nanoparticles and Polyaniline," Journal of Brazilian Chemistry Society, vol. 15, No. 3, pp. 378-384, (2004).

Selective laser sintering, from Wikipedia, (http://en.wikipedia.org/wiki/Selective_laser_sintering), pp. 1-2, downloaded on Sep. 28, 2007.

Senior et al., "Synthesis of tough nanoporous metals by controlled electrolytic dealloying," Nanotechnology, vol. 17, pp. 2311-2316, (2006).

Serra et al., "Preparation of functional Dna microarrays through laser-induced forward transfer," Applied Physics Letters, vol. 85, No. 9, pp. 1639-1641, Aug. 30, 2004.

Serruys et al., "The Effect of Variable Dose and Release Kinetics on Neointimal Hyperplasia Using a Novel Paclitaxel - Eluting Stent Platform," Journal of the American College of Cardiology, vol. 46, No. 2, pp. 253-260, Jul. 19, 2005.

Sgura et al., "The Lunar Stent: characteristics and clinical results", Herz, vol. 27, pages1-14, (2002).

Shabalovskaya et al., "Surface Conditions of Nitinol Wires, Tubing, and As-Cast Alloys. The Effect of Chemical Etching, Aging in Boiling Water, and Heat Treatment," Wiley Periodicals, Inc., Journal of Biomedical Materials Research Part B: Appiled Biomaterials, vol. 65B: pp. 193-203, (2003).

Shamiryan et al., "Comparative study of SiOCH low-k films with varied porosity interacting with etching and cleaning plasma," Journal of Vacuum Science Technology B, vol. 20, No. 5, pp. 1923-1928, Sep./Oct. 2002.

Shang et al., "Structure and photocatalytic characters of TiO2 film photocatalyst coated on stainless steel webnet," Journal of Molecular Catalysis a: Chemical, vol. 202, pp. 187-1995, (2003).

Shao et al., "Fiber mats of poly(vinyl alcohol)/silica composite via Electrospinning," Materials Letters, vol. 57, pp. 1579-1584, (2003).

Shchukin et al., "Micron-scale hollow polyelectrolyte capsules with naosized magnetic Fe304 inside," Materials Letters, vol. 57, pp. 1743-1747, (2003).

Shevchenko et al., "Porous Surface of NiTi Alloy Produced by Plasma Ion Implantation," Institute of Ion Beam Physics and Materials Research, 1 p., May 2005.

Shevchenko, "Formation of nonoporous structures on stainless steel surface," Report, pp. 1-6, Apr. 2007.

Shibli et al., "Development of phosphate inter layered hydroxyapatite coating for stainless steel implants", Applied Surface Science, vol. 254, pp. 4103-4110, (2008).

Shockravi et al., "Soluable and thermally stable polyamides bearing 1,1'-thiobis(2-naphthoxy) groups," European Polymer Journal, vol. 43, pp. 620-627, (2007).

Shustak et al., "n-Alkanoic Acid Monolayers on 316L Stainless Steel Promote the Adhesion of electropolymerized Polypyrrole Films," Langmuir, vol. 22, pp. 5237-5240, (2006).

Siegfried et al., "Reactive Cylindrical Magnatron Deposition of Titanium Nitride and Zirconium Nitride Films," Society of Vacuum Coaters, 39th Annual Technical Conference Proceedings, pp. 97-101, (1996).

Silber et al., "A new stainless-steel-free stent with a potential of artifact free magnetic resonance compatibility: first clinical experience (Ein neuer Edelstahl-freier Stent mit Potential zur artefaktfreien Mr-Kompatibilitat: Erste klinische Erfahrungen)," German Society for Cardiology -Heart and Cardiovascular Research (Deutche Gesellschaft fur Kardiologie - Herz and Kreislaufforschung), 1 p., Oct. 30, 2005.

Silber et al., "A new stainless-steel-free stent with a potential of artifact free magnetic resonance compatibility: first clinical experience," Abstract and Poster, pp. 1-3, May 2006.

Silber, " Lusty-Fim Study: Lunar Starflex First in Man Study, " PowerPoint presentation at the Paris Course on Revascularization, pp. 1-11, May 2003.

Silber, "Ein edelstahfreier stent aus niobium mit iridiumoxyd (IrOx)-beschichtung: Erste Ergebnisse der Lusty-studie" (Stainless steel-free Stent out of niobium with iridiumoxyd (IrOx)-coating: Initial results of the Lusty-study), PowerPoint presentation, pp. 1-16, Oct. 15, 2004.

Silber, "Lusty-Fim Study: Lunar Starflex First in Man Study," PowerPoint presentation, pp. 1- 16, 2003.

Silber, "Niobium/iridiumoxide Stents: Lusty randomized trial, Lunar Rox registry," PowerPoint presentation, pp. 1-33, 2003.

Silva et al., "Electrochemical characterisation of oxide films formed on Ti-6A1-4V alloy implanted with Ir for Bioengineering applications," Electrochimica Acta, vol. 43, Nos. 1-2, pp. 203-211, (1998).

Simon et al., "Influence of topography on endothelialization of stents: Clues for new designs,".

Singer, "Paclitaxel Poliglumex (Xyotax, Ct-2103): a Macromolecular Taxane," Journal of Controlled Release, vol. 109, 120-126, (2005).

Singh et al., "Review: Nano and macro-structured component fabrication by electron beam-physical vapor deposition (Eb-Pvd)," Journal of Materials Science, vol. 40, pp. 1-26, (2005).

Sniadecki et al., "Nanotechnology for Cell-Substrate Interactions," Annals of Biomedical Engineering, vol. 34, No. 1, pp. 59-74, Jan. 1, 2006.

Sofield et al., "Ion beam modification of polymers," Nuclear Instruments and Methods in Physics Research, vol. B67, pp. 432-437, (1992).

Soler-Illia et al., "Block Copolymer-Templated Mesoporous Oxides," "Current Opinion in Colloid and Interface Science," vol. 8, pp. 109-126, (2003).

Song et al., "Biomimetic apatite coatings on micro-arc oxidized titania," Biomaterials, vol. 25, pp. 3341-3349, (2004).

Sousa et al., "New Frontiers in Cardiology: Drug-Eluting Stents: Part I," Circulation: Journal of the Americal Heart Associate, vol. 107, pp. 2274-2279, http:/www.circ.ahajournals.org, (2003).

Spasova et al., "Magnetic and optical tunable microspheres with a magnetite/gold nanoparticle shell," Journal of Material Chemisty, vol. 115, pp. 2095-2098, (2005).

Sprague et al., "Endothelial cell migration onto metal stent surfaces under static and flow conditions," Journal of Long-Term Effects of Medical Implants, vol. 10, No. 1-2, pp. 97-110, (2000).

Startschuss fur "lusty" -studie, (Launch of "lusty" -study), Cardio News, 1 p., Oct. 2002.

Stucky "High Surface Area Materials," pp. 1-5, Published: Jan. 1998, Wtec Hyper-Librarian, (http://www.wtec.org/loyola/nano/US.Review/07_03.htm).

Studart et al., "Colloidal Stabilization of Nanoparticles in Concentrated Suspensions," Langmuir, vol. 23, pp. 1081-1090, (2007).

Sun et al., "Construction of Size-Controllable Hierarchical Nanoporous TiO2 Ring Arrays and Their Modifications," Chem. Mater, vol. 18, pp. 3774-3779, (2006).

Sun et al., "Non-Fouling Biomaterial Surfaces: Ii Protein Adsorption on Radiation Grafted Polyethylene Glycol Methacrylate Copolymers," Polymer Preprints, vol. 28, No. 1, pp. 292-294, Apr. 1987.

Sundararajan et al., "Mechanisms underlying the formation of thick alumina coatings through the Mao coating technology," Surface and Coatings Technolgy, vol. 167, pp. 269-277, (2003).

Sung et al., "Formation of Nanoporous and Nanocrystalline Anatase Films by Pyrolysis of PEOTi02 Hybrid Films," Journal of Crystal Growth, vol. 286, pp. 173-177, (2006).

Szycher et al., "Drug-Eluting Stents to Prevent Coronary Restenosis," CardioTech International, pp. 1-10, (2002).

Tabata et al., "Generalized Semiempirical Equations for the Extrapolated Range of Electronics," Nuclear Instruments and Methods, vol. 103, pp. 85-91, Mar. 28, 1972.

Takitani et al., "Desorption of Helium from Austenitic Stainless Steel Heavily Bombarded by Low Energy He Ions," Journal of Nuclear Materials, vol. 329-333, pp. 761-765, (2004).

Tamura et al., "Surface Hydroxyl Site Densities on Metal Oxides as a Measrure for the Ion-Exchange Capacity," Journal of Colloid and Interface Science, vol. 209, pp. 225-231, (1999).

Tan et al., "Corrosion and wear-corrosion behavior of NiTi modified by plasma source ion implantation," Biomaterials, vol. 24, pp. 3931-3939, (2003).

Tanaka et al., "Micrometer-scale fabrication and assembly using focused ion beam," Thin Solid Films, vol. 509, pp. 113-117, (2006).

Tang et al., "Electrochemical Study of a Polarized Electrochemical Vapor Deposition Process," Journal of the Electrochemical Society, vol. 147, No. 9, pp. 3338-3344, (2000).

Tang et al., "Fabrication of Macroporous Alumina with Tailored Porosity," Jornal of American Ceramic Society, vol. 86, No. 12, pp. 2050-2054, (2003).

Tang et al., "Preparation of Porous anatase titania film," Materials Letters, vol. 58, pp. 1857- 1860, (2004).

Tapphorn et al., "The Solid-State Spray Forming of Low-Oxide Titanium Components," Journal of Metals, vol. 50, No. 9, pp. 45-46,76, (1998).

Tassin et al., "Improvement of the Wear Resistance of 316 L Stainless Steel by Laser Surface Alloying," Surface and Coatings Technology, vol. 80, No. 9, pp. 207-210, (1996).

Terlingen, "Functionalization of Polymer Surfaces," Europlasma Technical Paper, pp. 1-29, May 8, 2004.

Terumo Europe, "Terumo Europe n. V. Enrols First Patient in Clinical Trial of the Nobori Drug-Eluting Coronary Stent," Press Release, 1 p., May 26, 2005, (http://www.temmoeurope.com/_press_release/may_262005.html.).

Thierry et al., "Bioactive Coatings of Endovascular Stents Based on Polyelectrolyte Multilayers," Biomacromolecules, vol. 4, pp. 1564-1571, (2003).

Thompson et al., "Tuning compliance of nanoscale polyelectrolyte multilayers to modulate cell adhesion," Biomaterials, vol. 26, pp. 6836-6845, (2005).

Tierno et al., "Using Electroless Deposition for the Preparation of Micron Sized Polymer/Metal Core/Shell Particles and Hollow Metal Spheres," Journal of Physics Chemistry B, vol. 110, pp. 3043-3050, (2006).

Tollon, "Fabrication of coated biodegradable polymer scaffolds and their effects on murin embryonic stem cells," Thesis presented to the University of Florida, pp. 1-7, (2005).

Tonosaki et al., "Nano-indentation testing for plasma-based ion-implanted surface of plastics," Surface and Coatings Technology, vol. 136, pp. 249-251, (2001).

Tones-Costa et al., "Rbs Characterization of Porous Silicon Multilayer Interference Filters," Electrochemical and Solid-State Letters, vol. 7, No. 11, pp. G244-G249 (2004).

Toth et al., "Ar+laser-induced forward transfer (Lift): a novel method for micrometer-size surface patterning," Applied Surface Science, vol. 69, pp. 317-320, (1993).

Tsyganov et al., "Blood compatibilty of titanium-bases coatings prepared by metal plasma immersion ion implantation and deposition," Applied Surface Science, vol. 235, pp. 156-163, (2004).

Tsyganov et al., "Structure and Properties of Titanium Oxide Layers prepared by Metal Plasma Immersion Ion Implantation and Deposition," Surface & Coatings Technology, vol. 174-175, pp. 591-596, (2003).

Tsyganov et al., "Correlation between blood compatibility and physical surface properties of titanium-based coatings," Surface & Coatings Technology, vol. 200, pp. 1041-1044, (2005).

Uchida et al., "Apatite-forming ability of a zirconia/alumina nanocomposite induced by chemical treatment," Journal of Biomedical Materials Research, vol. 60, No. 2, pp. 277-282, May 2002.

University of Wisconsin, "Effect of Nano-Scale Textured Biomimetic Surfaces on Proliferation and Adhesion of Corneal Epithelial Cells," Materials Research Science and Engineering Center, pp. 12, (1997), (http://mrsec.wisc.edu/Past_proiects/seedproi4/Seedproi4.html).

Uyama et al., "Surface Modifications of Polymers by Grafting," Advances in Polymer Science, vol. 139, pp. 1-39, (1998).

Valsesia et al., "Selective immobilization of protein clusters on polymeric nanocraters," Advanced Functional Materials, vol. 16, pp. 1242-1246, (2006).

Valsesia, a. et al., "Fabrication of nanostructured polymeric surfaces for biosensing devices," Nanoletters, vol. 4, No. 6, pp. 1047-1050, (2004).

Van Alsten, "Self-Assembled Monolayers on Engineering Metals: Structure, Derivatization, and Utility," Langmuir, vol. 15, pp. 7605-7614, (1999).

Van Den Berg, "Nano particles play with electrons," pp. 1-9, [first downloaded on Nov. 12, 2003], (http://www.delftoutlook.tudelft.nl/info/index21fd.html?hoofdstuk=Article&ArtID=2243).

van der Eijk et al., " Metal Printing Process Development of a New Rapid Manufacturing Process for Metal Parts," Proceedings of the World PM2004 Conference held in Vienna, pp. 1-5, Oct. 1721, 2004.

Van Steenkiste et al., "Kinetic spray coatings," Surface & Coatings Technology, vol. 111, pp. 62- 71, (1999).

Vayssieres, "On the design of advanced metal oxide nanomaterials," International Journal of Nanotechnology, vol. 1, Nos. 1/2, pp. 1-41, (2004).

Velev et al., "Colloidal crystals as templates for porous materials," Current Opinion in Colloid & Interface Science, vol. 5, pp. 56-63, (2000).

Velev et al., "Porous silica via colloidal crystallization," Nature, vol. 389, pp. 447-448, Oct. 2, 1997.

Verheye et al., "Reduced Thrombus Formation by Hyaluronic Acid Coating of Endovascular Devices," Arteriosclerosis, Thrombosis, and Vascular Biology: Journal of the American Heart Association, vol. 20, pp. 1168-1172, (2000).

Vidal et al., "Electropolymerization of pyrrole and immobilization of glucose oxidase in a flow system: influence of the operating conditions on analytical performance," Biosensors & Bioelectronics, vol. 13, No. 3-4, pp. 371-382, (1998).

Vigil et al., "TiO2 Layers Grown from Flowing Precursor Solutions Using Microwave Heating," Langmuir, vol. 17, pp. 891-896, (2001).

Viitala et al., "Surface properties of in vitro bioactive and non-bioactive sol-gel derived materials," Biomaterials, vol. 23, pp. 3073-3086, (2002).

Vitte et al., "Is there a predictable relationship between surface physical-chemical properties and cell behaviour at the interface?" European Cells and Materials, vol. 7, pp. 52-63, (2004).

Volkel et al., "Electrodeposition of coppeer and cobalt nanostructures using self-assembled monolayer templates," Surface Science, vol. 597, pp. 32-41, (2005).

Vu et al., "Eletrophoretic deposition of nanocomposites formed from polythiophene and metal oxides," Electrochimica Acta, vol. 51, pp. 1117-1124, (2005).

VukoviO et al., "Anodic stability and electrochromism of electrodeposited ruthenium-iridium coatings on titanium," Journal of Electroanalytical Chemistry, vol. 330, pp. 663-673 (1992).

Walboomers et al., "Effect of microtextured surfaces on the performance of percutaneous devices," Journal of Biomedical Materials Research Part a, vol. 74A, No. 3, pp. 381-387, (2005).

Wang et al., "Deposition of in-plane textured MgO on amorphous Si3N4 substrates by ion-beamassisted deposition and comparisons with ion-beam-assistend deposidted yttria-stabilized-zirconia," Applied Physics Letters, vol. 71, No. 17, Issue 20, pp. 2955-2957, Nov. 17, 1997.

Wang et al., "Effect of substrate temperature on structure and electrical resistivity of laser ablated Ir02 thin films," Applied Surface Science, vol. 253, pp. 2911-2914, (2006).

Wang et al., "Effect of the discharge pulsating on microarc oxidation coating formed on Ti6A14V alloy," Materials Chemistry and Physics, vol. 90, pp. 128-133, (2005).

Wang et al., "Novel Poly(3-nonylthiophene)-TiO2 Hybrid Materials for Photovoltaic Cells," Synthetic Metals, vol. 155, pp. 677-680, (2005).

Wang et al., "Polyelectrolyte-Coated Colloid Spheres as Templates for Sol-Gel Reactions," Chem. Mater., vol. 14, pp. 1909-1913, (2002).

Wang et al., "Pulsed laser deposition of organic thin films," This Solid Films, vol. 363, pp. 58-60, (2000).

Wang et al., "Synthesis of Macroporous Titania and Inorganic Composite Materials from Coated Colloidal Spheres - a Novel Route to Tune Pore Morphology," Chem. Mater., vol. 13, pp. 364371, (2001).

Webster et al." Enhanced functions of osteoblasts on nanophase ceramics," Biomaterials, vol. 21, No. 17, pp. 1803-1810, Sep. 2000.

Webster et al., "Increased osteoblast adhesion on nanophase metals: Ti, Ti6A14V, and CoCrMo," Biomaterials, vol. 25, No. 19, pp. 4731-4739, (2004).

Webster et al., "Specific proteins mediate enhanced osteoblast adhesion on nanophase ceramics," Journal of Biomedical Materials Research, vol. 5, No. 51, pp. 475-483, Sep. 2000.

Wei et al., "Structural Characterisation of Doped and Undoped Nanocrystalline Zinc Oxides Deposited by Ultrasonic Spray Assisted Chemical Vapour Deposition," Journal of Physics: Conference Series, vol. 26, pp. 183-186 (2006).

Wells, "Patterned Plasma Immersion Exposure of Insulating Materials for the Purpose of Modifying Optical Properties," thesis submitted to the college of William and Mary, Williamsburg, Vriginia, pp. 1-59, Apr. 2000.

Wesolowski et al., "Surface Charge and Ion Adsorption on Metal Oxides to 290°C," Division of Chemical Sciences, Geosciences, and Biosciences, Office of Basic Energy Sciences, U.S. Department of Energy, pp. 1-6, (2001).

Wessling et al., "Rf-sputtering of iridium oxide to be used as stimulation material in functional medical implants," Journal of Micromechanics and Microengineering, vol. 16, pp. S142-S148 (2006).

Whelan, "Targeted Taxane Therapy for Cancer," Drug Discovery Today, vol. 7, No. 2, pp. 90-92, Jan. 2002.

Which stent is right for you? pp. 1-3, (circa 2004).

Wieneke et al., "Synergistic Effects of a Novel Nanoporous Stent Coating and Tacrolimus on Intima Proliferation in Rabbits," Catheterization and Cardiovascular Interventions, vol. 60, pp. 399-407, (2003).

Wilkinson et al., "Nanofabrication in cellular engineering," Journal of Vacuum Science & Technology B, vol. 16, No. 6, pp. 3132-3136, (1998).

Wilkinson et al., "The use of materials patterned on a nano- and micro-metric scale in cellular engineering," Materials Science & Engineering C, vol. 19, No. 1-2, pp. 263-269, (2002).

Wilson et al., "Mediation of biomaterial-cell interactions by adsorbed proteins: a review," Tissue Engineering, vol. 11, No. 1-2, pp. 1-18, (2005).

Wong et al., "Balance of chemistry, topography, and mechanics at the cell-biomaterial interface: Issues and challenges for assessing the role of substrate mechanics on cell response," Surface Science, vol. 570, No. 1-2, pp. 119-133, (2004).

Wong et al., "Polymer segmental alignment in polarized pulsed laser-induced periodic surface structures," Applied Physics a, vol. 65, pp. 519-523, (1997).

Wood, "Next-generation drug-eluting stents tackle shortcomings of Cypher, Taxus," Heart Wire, pp. 1-6, Feb. 7, 2006, (http://www.theheart.org/article/641591.do.).

World Reference definition, "Interconnected," WorldReference.com, 1 p., [downloaded Jan. 21, 2010].

Wu et al., "Characterization of Mesoporous Nanocrystalline TiO2 Photocatalysts Synthesized Via a Sol-Solvothermal Process at a Low Temperature," Journal of Solid State Chemistry, vol. 178, pp. 321-328, (2005).

Wu et al., "Chitosan-Mediated and Spatially Selective Electrodeposition of Nanoscale Particles," Langmuir, vol. 21, pp. 3641-3646, (2005).

Wu et al., "Corrosion resistance of BaTiO3 films prepared by plasma electrolytic oxidation," Surface and Coatings Technology, vol. 166, pp. 31-36, (2002).

Wu et al., "Design of Doped Hybrid Xerogels for a Controlled Release of Brilliant Blue Fcf," Journal of Non-Crystalline Solids, vol. 342, pp. 46-53, (2004).

Wu et al., "The effects of cathodic and anodic voltages on the characteristics of purous nanocrystalline titania coatings fabricated by microarc oxidation," Materials Letters, vol. 59, pp. 370-375, (2005).

Xia et al., "Monodispersed Colloidal Spheres: Old Materials with New Applications," Advanced Materials, vol. 12, No. 10, pp. 693-713, (2000).

Xu et al., "An Improved Method to Strip Aluminum from Porous Anodic Alumina Films," Langmuir, vol. 19, pp. 1443-1445, (2003).

Xu et al., "Cold spay deposition of thermoplastic powder," Surface & Coatings Technology, vol. 2001, pp. 3044-3050, (2006).

Xu et al., "Synthesis of porosity controlled ceramic membranes," Journal of Material Research, vol. 6, No. 5, pp. 1073-1081, May 1991.

Yamato et al. "Nanofabrication for micropatterned cell arrays by combining electron beam-irradiated polymer grafting and localized laser ablation," Journal of Biomedical Materials Research, vol. 67, No. 4, pp. 1065-1071, Dec. 15, 2003.

Yan et al., "New Mocvd precursor for iridium thin films deposition," Materials Letters, vol. 61, pp. 216-218, (2007).

Yan et al., "Sol-gel Processing," Handbook of Nanophase and Nanostructured Materials, vol. 1: Synthesis, Chapter 4, pp. 1-27, (2003).

Yang et al., "Laser spray cladding of porous NiTi coatings on NiTi substrates," the Hong Kong Polytechnic University, 1 p., Dec. 28, 2006.

Yang et al., "Poly(L,L-lactide-co-glycolide)/tricalcium phosphate composite scaffold and its various changes during degradation in vitro," Polymer Degradation and Stability, vol. 91 pp. 3065-3073, (2006).

Yang et al., "Thermal oxidation products and kinetics of polyethylene composites," Polymer Degradation and Stability, vol. 91, pp. 1651-1657, (2006).

Yang et al., "Solution phase synthesis of magnesium hydroxide sulfate hydrate nanoribbons", Nanotechology, vol. 15, pp. 1625-1627, (2004).

Yankov et al., "Reactive plasma immersion ion implantation for surface passivation," Surface and Coatings Technology, vol. 201, pp. 6752-6758, (2007).

Yap et al., "Protein and cell micropatterning and its integration with micro/nanoparticles assembley," Biosensors and Bioelectronics, vol. 22, pp. 775-788, (2007).

Yerokhin et al., "Kinetic aspects of aluminium titanate layer formation on titanium alloys by plasma electrolytic oxidation," Applied Surface Science, vol. 200, pp. 172-184, (2002).

Yerokhin et al., "Plasma electrolysis for surface engineering," Surface Coatings Technology, vol. 122, pp. 73-93, (1999).

Yim et al., "Nanopattern-induced changes in morphology and motility of smooth muscle cells," Biomaterials, vol. 26, pp. 5405-5413, (2005).

Yim et al., "Significance of synthetic nanostructures in dictating cellular response," Nanomedicine: Nanotechnology, Biology and Medicine, vol. 1, No. 1, pp. 10-21, Mar. 1, 2005.

Yoldi et al., "Electrophoretic deposition of colloidal crystals assisted by hydrodynamic flows," Journal of Materials Science, vol. 41, pp. 2964-2969, (2006).

Yoshida et al., "Impact of Low Energy Helium Irradiation on Plasma Facing Metals," Journal of Nuclear Materials, vol. 337-339, pp. 946-950, (2005).

Young et al., "Polarized electrochemical vapor deposition for cermet anodes in solid oxide fuel cells," Solid State Ionics, vol. 135, pp. 457-462, (2000).

Yu et al., "Encapsulated cells: an atomic force microscopy study," Biomaterials, vol. 25, pp. 3655-3662, (2004).

Yu et al., "Enhanced photocatalytic activity of mesoporous and ordinary TiO2 thin films by sulfuric acid treatment," Applied Catalysis B: Environmental, vol. 36, pp. 31-43, (2002).

Yu et al., "Enhanced photoinduced super-hydrophilicity of the sol—gel-derived TiO2 thin films by Fe-doping," Materials Chemistry and Physics, vol. 95, pp. 193-196, (2006).

Yu et al., "Light-induced super-hydrophilicity and photocatalytic activity of mesoporous TiO2 thin films," Journal of Photochemistry and Photobiology a: Chemistry, vol. 148, pp. 331-339, (2002).

Yun et at., "Low-Temperature Coating of Sol-Gel Anatase Thin Films," Materials Letters, vol. 58, pp. 3703-3706, (2004).

Zakharian et al., "A Fullerene-Paclitaxel Chemotherapeutic: Synthesis, Characterization, and Study of Biological Activity in Tissue Culture," Journal of American Chemistry Society, vol. 127, pp. 12508-12509, (2005).

Zbroniec et al., "Laser ablation of iron oxide in various ambient gases," Applied Surface Science, vol. 197-198, pp. 883-886, (2002).

Zeng et al., "Biodegradable electrospun fibers for drug delivery," Journal of Controlled Release, vol. 92, pp. 227-231, (2003).

Zhang et al., "Surface analyses of micro-arc oxidized and hydrothermally treated titanium and effect on osteoblast behavior," Journal of Biomedical Materials Research, vol. 68A, pp. 383-391, (2004).

Zhang et al., "Surface treatment of magnesium hydroxide to improve its dispersion in organic phase by the ultrasonic technique", Applied Surface Science, vol. 253, pp. 7393-7397, (2007).

Zhao et al., "Coating deposition by the kinetic spray process," Surface & Coatings Technology, vol. 200, pp. 4746-4754, (2006).

Zhao et al., "Designing Nanostructions by Glancing Angle Deposition," Proceedings of Spie, vol. 5219: Nanotubes and Nanowires, pp. 59-73, (2003).

Zhao et al., "Formulation of a ceramic ink for a wide-array drop-on-demand ink jet printer," Ceramics International, vol. 29, pp. 887-892, (2003).

Zheng et al., "Substrate temperature dependent morphology and resistivity of pulsed laser deposited iridium oxide thin films," Thin Solid Films, vol. 496, pp. 371-375, (2006).

Zheng et al., "Synthesis of Mesoporous Silica Materials via Nonsurfactant Templated Sol-Gel Route Using Mixture of Organic Compounds as Template," Journal of Sol-Gel Science and Technology, vol. 24. pages 81-88, (2002).

Zhitomirsky et al., "Cathodic electrodeposition of MnOx films for electrochemical supercapacitors," Electrochimica Acta, vol. 51, pp. 3039-3045, (2006).

Zhitomirsky et al., "Electrodeposition of composite hydroxyapatite-chitosan films," Materials Chemistry and Physics, vol. 94, pages 245-251, (2005).

Zhou et al., "Branched Ta nanocolumns grown by glancing angle deposition," Applied Physics Letters, vol. 88, p. 203117, (2006).

Zoppi et al., "Hybrid Films of Poly(ethylene oxide-b-amide 6) Containing Sol-Gel Silicon or Titanium Oxide as Inorganic Fillers: Effect of Morphology and Mechanical Properties on Gas Permeability," Polymer, vol. 41, pp. 5461-5470, (2000).

Zou et al., "Highly textural lamellar mesostructured magnesium hydroxide via a cathodic electrodeposition process", Materials Letters, vol. 61, pp. 1990-1993, (2007).

U.S. Appl. No. 11,694,436, Mar. 30, 2007, Atanasoska et al.
U.S. Appl. No. 2004/0215169, Oct. 28, 2004, Li.
U.S. Appl. No. 2004/0215313, Oct. 28, 2004, Cheng.
U.S. Appl. No. 2004/0219214, Nov. 4, 2004, Gravett et al.
U.S. Appl. No. 2004/0220510, Nov. 4, 2004, Koullick et al.
U.S. Appl. No. 2004/0220662, Nov. 4, 2004, Dang et al.
U.S. Appl. No. 2004/0224001, Nov. 11, 2004, Pacetti et al.
U.S. Appl. No. 2004/0225346, Nov. 11, 2004, Mazumder et al.
U.S. Appl. No. 2004/0225347, Nov. 11, 2004, Lang.
U.S. Appl. No. 2004/0228905, Nov. 15, 2004, Greenspan et al.
U.S. Appl. No. 2004/0230176, Nov. 18, 2004, Shanahan et al.
U.S. Appl. No. 2004/0230290, Nov. 18, 2004, Weber et al.
U.S. Appl. No. 2004/0230293, Nov. 18, 2004, Yip et al.
U.S. Appl. No. 2004/0234737, Nov. 25, 2004, Pacetti.
U.S. Appl. No. 2004/0234748, Nov. 25, 2004, Stenzel.
U.S. Appl. No. 2004/0236399, Nov. 25, 2004, Sundar.
U.S. Appl. No. 2004/0236415, Nov. 25, 2004, Thomas.
U.S. Appl. No. 2004/0236416, Nov. 25, 2004, Falotico.
U.S. Appl. No. 2004/0237282, Dec. 2, 2004, Hines.
U.S. Appl. No. 2004/0242106, Dec. 2, 2004, Rabasco et al.
U.S. Appl. No. 2004/0243217, Dec. 2, 2004, Andersen et al.
U.S. Appl. No. 2004/0243241, Dec. 2, 2004, Istephanous.
U.S. Appl. No. 2004/0247671, Dec. 9, 2004, Prescott et al.
U.S. Appl. No. 2004/0249444, Dec. 9, 2004, Reiss.
U.S. Appl. No. 2004/0249449, Dec. 9, 2004, Shanley et al.
U.S. Appl. No. 2004/0254635, Dec. 16, 2005, Shanley et al.
U.S. Appl. No. 2004/0261702, Dec. 30, 2004, Grabowy et al.
U.S. Appl. No. 2004/086674, May 6, 2004, Holman.
U.S. Appl. No. 2010/0130346, May 27, 2010, Laine et al.
U.S. Appl. No. 2010/0131050, May 27, 2010, Zhao.
U.S. Appl. No. 2011/0034752, Feb. 10, 2011, Kessler et al.
U.S. Appl. No. 2006/193886, Aug. 31, 2006, Owens et al.
U.S. Appl. No. 2007/224116, Sep. 27, 2007, Chandrasekaren et al.
US 6,533,715, 03/2003, Hossainy et al. (withdrawn)

* cited by examiner

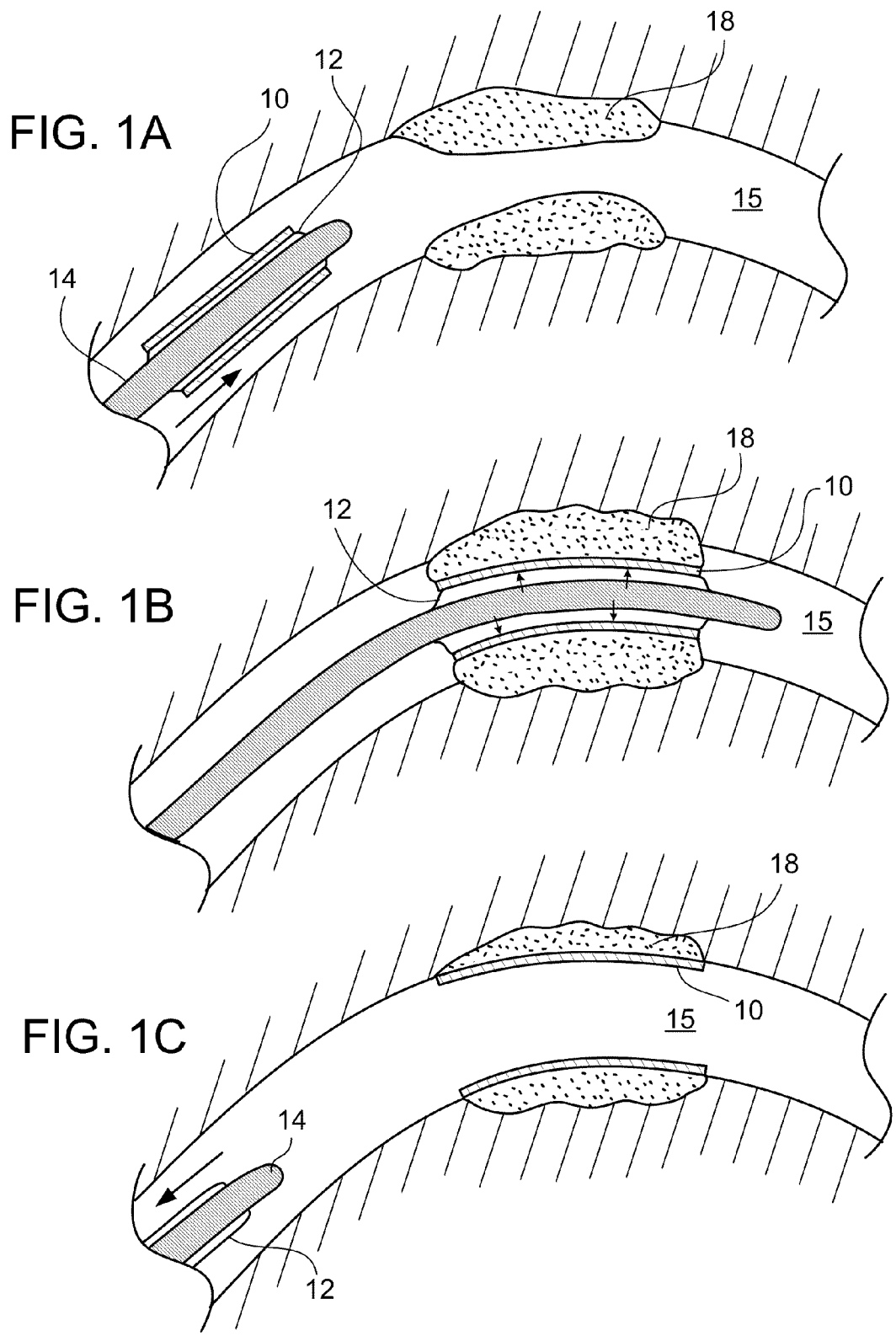

ENDOPROSTHESIS COATING

CROSS-REFERENCE TO RELATED APPLICATIONS

This application claims priority under 35 USC §119(e) to U.S. Provisional Patent Application Ser. No. 61/073,647, filed on Jun. 18, 2008, the entire contents of which are hereby incorporated by reference.

TECHNICAL FIELD

This disclosure relates to coating endoprostheses.

BACKGROUND

The body includes various passageways including blood vessels such as arteries, and other body lumens. These passageways sometimes become occluded or weakened. For example, they can be occluded by a tumor, restricted by plaque, or weakened by an aneurysm. When this occurs, the passageway can be reopened or reinforced, or even replaced, with a medical endoprosthesis. An endoprosthesis is an artificial implant that is typically placed in a passageway or lumen in the body. Many endoprostheses are tubular members, examples of which include stents, stent-grafts, and covered stents.

Many endoprostheses be delivered inside the body by a catheter. Typically the catheter supports a reduced-size or compacted form of the endoprosthesis as it is transported to a desired site in the body, for example the site of weakening or occlusion in a body lumen. Upon reaching the desired site the endoprosthesis is installed so that it can contact the walls of the lumen. Stent delivery is further discussed in Heath, U.S. Pat. No. 6,290,721, the entire contents of which is hereby incorporated by reference herein.

One method of installation involves expanding the endoprosthesis. The expansion mechanism used to install the endoprosthesis may include forcing it to expand radially. For example, the expansion can be achieved with a catheter that carries a balloon in conjunction with a balloon-expandable endoprosthesis reduced in size relative to its final form in the body. The balloon is inflated to deform and/or expand the endoprosthesis in order to fix it at a predetermined position in contact with the lumen wall. The balloon can then be deflated, and the catheter withdrawn.

It is sometimes desirable for an endoprosthesis to contain a therapeutic agent, or drug which can elute into the body fluid in a predetermined manner once the endoprosthesis is implanted.

SUMMARY

In one aspect, the disclosure features an endoprosthesis, e.g., a stent (e.g., a drug eluting stent), that includes a surface having a porous structure of a first material and a coating of a second material. The second material defines a plurality of hollow elements.

In some implementations, the hollow elements and the coating are made of non-polymeric material, for example, a ceramic material, a metal, an alloy, or a mixture thereof.

Implementations may include one or more of the following features. The endoprosthesis has a body formed of the first material. The first material is a metal. The metal is stainless steel, nitinol, tungsten, tantalum, rhenium, iridium, silver, gold, bismuth, platinum or alloys thereof. The second material is a ceramic material. The ceramic material is silicon oxide, titanium oxide, iridium oxide or a mixture thereof. The coating and hollow elements have a porous structure. The porous structure comprises a plurality of pores having a width of about 0.5 nm to about 500 nm. The coating and hollow elements have a thickness of about 1 nm to about 1 µm. The hollow elements contain a drug. The porous structure of the first material includes a plurality of pores having a width and a depth of about 1 nm to about 25 µm. The surface has a porosity of about 90% or less (e.g., about 80%, about 70%, about 60%, about 50% or less). The hollow elements are hollow spheres. The hollow spheres have an outer diameter of about 10 nm to about 5 µm. The hollow spheres have an inner diameter of about 1 nm to about 5 µm.

In another aspect, the disclosure features a method of making an endoprosthesis that includes applying a sacrificial template to a surface, applying a ceramic precursor over the template, treating the precursor to form a ceramic deposit, and removing the sacrificial template to form a hollow ceramic region.

Implementations may include one or more of the following features. The ceramic precursor includes a metal oxide precursor. The metal oxide precursor is tetraethylorthosilicate, titanium isopropoxide, or iridium acetylacetonate. The sacrificial template is removed by calcination or chemical removal. A plurality of pores are formed on a surface where the pores have a width and a depth of about 1 nm to about 25 µm. The pores of the spheres and ceramic are formed by calcination or chemical removal. The structure of the substrate is formed by a plasma treatment. A polyelectrolyte layer is applied before applying the sacrificial template. A polyelectrolyte layer is applied after applying the sacrificial template. One or more polyelectrolyte layers could be applied to the porous surface. The sacrificial template is applied to the polyelectrolyte layers. The sacrificial template is applied to the porous surface. One or more polyelectrolyte layers are applied to the sacrificial template. The sacrificial template is pretreated with a polyelectrolyte to be encapsulated by a polyelectrolyte coating. The polyelectrolyte layers are applied by LBL deposition. The sacrificial template is a sphere. The sacrificial template is a polymer particle. The polymer particle has a size of about 10 nm to about 10 µm. A sol-gel ceramic precursor is applied to the polyelectrolyte layers and the template. The sol-gel precursor reacts to form a ceramic gel deposit. The ceramic gel deposit is converted to an oxide or ceramic (e.g. by hydrolysis and condensation reactions). The polyelectrolyte layers and template are removed by heating or chemical etching. A drug is provided in the hollow ceramic region. The drug is loaded to the endoprosthesis after the coating is formed. The drug is loaded to the endoprosthesis before the coating is formed.

Aspects and/or implementations may have one or more of the following additional advantages. The endoprosthesis, e.g., a drug eluting stent, can include a large number of porous hollow elements embedded in and/or on its porous surface to facilitate drug elution. For example, metallic materials are mechanically stable but often lack porosity or drug-loading capacity while ceramic materials are porous but lack sufficient mechanical strength. A composition of a pretreated metal surface with hollow ceramic elements to contain drugs can have both sufficient mechanical strength and drug-loading capacity (e.g. porosity). The wall thickness of hollow elements can be independently controlled to be thin enough to resist cracking, flaking or peeling from the underlying metal surface. The porosity of a drug eluting stent, can be controlled, e.g., increased, by embedding the hollow elements having porous walls without compromising mechanical strength of the stent. The enhanced porosity facilitates drug loading. The drug elution profile over time can be selected by controlling the porosity of the metal and/or the properties of the hollow elements. For example, hollow elements made of the same material with thicker walls will release drugs at slower rate than the ones with thinner walls. Thus, introducing hollow elements with different size, different wall thickness, wall composition, or a geometry allows building a variety of drug release profiles. Further, the drug load can be easily varied by controlling the number of hollow elements put in the stent. Additionally, pore size can be changed by altering salt, additives (i.e., glucose) and pH in the PEM layers. The endoprostheses may be fully endothelialized, and thus not need to be removed from a lumen after implantation.

Other aspects, features, and advantages will be apparent from the description and drawings, and from the claims.

DESCRIPTION OF DRAWINGS

FIGS. 1A-1C are longitudinal cross-sectional views, illustrating delivery of a stent in a collapsed state, expansion of the stent, and the deployment of the stent in a body lumen.

Like reference symbols in the various drawings indicate like elements.

DETAILED DESCRIPTION

Figure 2A:
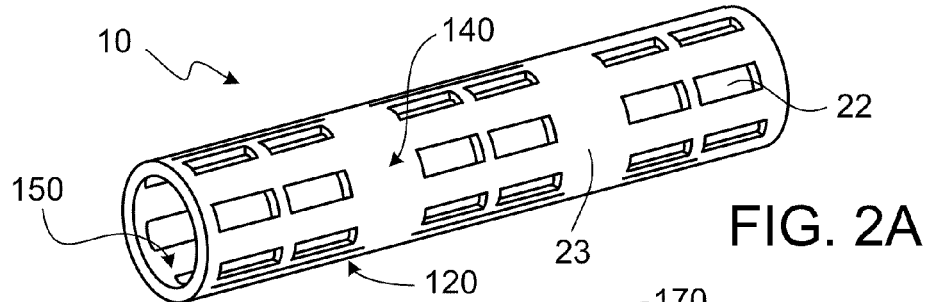
FIG. 2A is a perspective view of an implementation of a stent.

Referring to FIGS. 1A-1C, during implantation of a stent 10, the stent is placed over a balloon 12 carried near a distal end of a catheter 14, and is directed through a lumen 15 (FIG. 1A) until the portion carrying the balloon and stent reaches the region of an occlusion 18. The stent is then radially expanded by inflating balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C), leaving the stent 10 fixed within lumen 15. The stent can be balloon expandable, as illustrated above, or a self-expanding stent. Examples of stents are described in Heath '721, supra.

Figure 2B:
FIG. 2B is a schematic cross-sectional view of the surface of the stent.
Figure 2C:
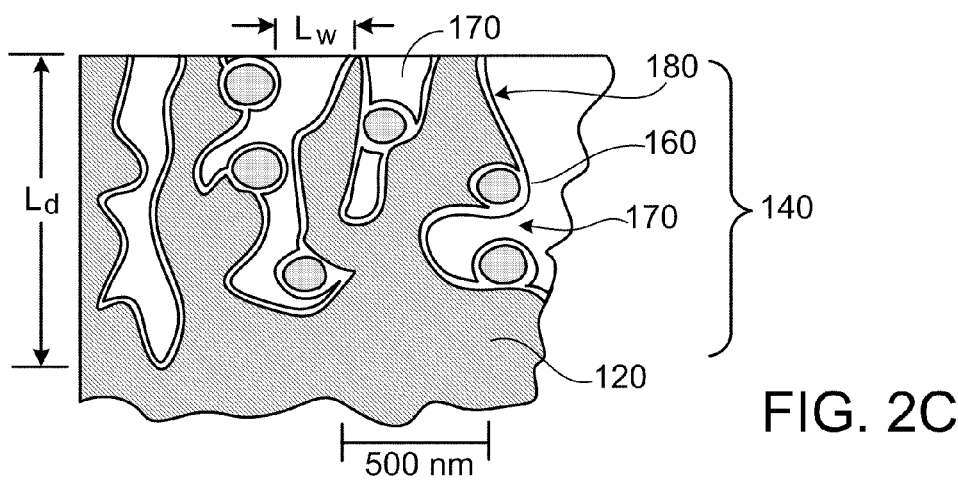
FIG. 2C is another schematic cross-sectional view of the surface.
Figure 2D:
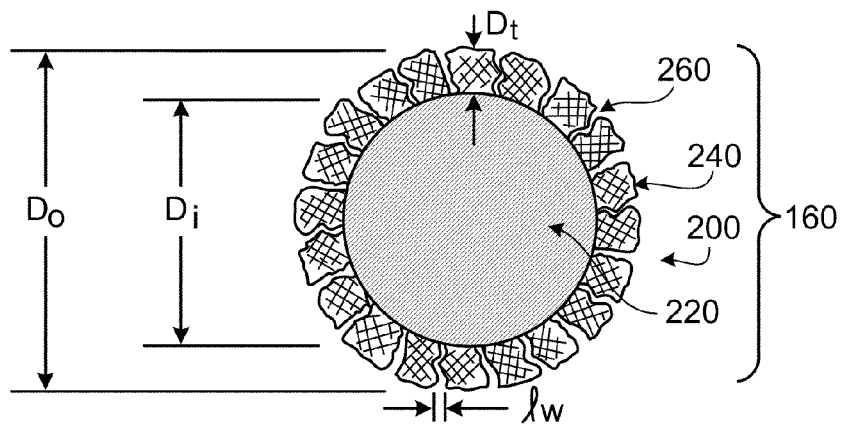
FIG. 2D is a schematic cross-sectional view of a drug-containing hollow sphere.

Referring to FIGS. 2A-2D, stent 10 is configured to include a releasable drug and to release the drug in a controlled and predetermined manner once it is implanted. Referring to FIG. 2A, the stent 10 is a generally tubular member including a plurality of fenestrations 22. The stent body 23 is made of a first material 120, e.g., a metal, and has a surface 140. Referring to FIG. 2B, a schematic cross-sectional view of the surface 140, the surface is porous or corrugated. Referring to FIG. 2C, a schematic cross-sectional view of the surface, the surface 140 is further coated with a second material 180, e.g., a ceramic material, and includes drug-containing hollow spheres 160 made of the second material 180. Referring to FIG. 2D, a schematic cross-sectional views of a drug-containing hollow sphere, the hollow sphere 160 includes a wall 240 having pores 260 connecting the interior 220 and the exterior 200 of the sphere 160. The interior 220 is a cavity containing a drug. The drug from the interior 220 of the spheres passes through the pores 260 into the porous space of surface 140 and then into body.

Referring particularly to FIGS. 2B and 2C, in some implementations, the first material 120 is a substantially pure metallic element, or an alloy (e.g., 316L stainless steel). The porous region of the surface 140 not only increases the effective area of the surface but also provides a more confined area to which the hollow spheres 160 can be attached, protecting the spheres from being dislodged during handling, delivery and deployment of the stent. In implementations, cross-sectional size or width of the pores 170 is large compared to the sphere size; in implementations, the width and depth of the pores provide a secondary control of drug release by diffusion of the drug through the pores 170 once the drug comes out of the hollow spheres 160. In other implementations, the pores are sized such that they provide a minor or no role in diffusion-limiting the drug release to body fluid or tissue. In implementations, the pore depth, $L_d$, is in the range of about 1 nanometer ("nm") to 250 micrometers ("microns" or "μm"), e.g., about 100 nm to 1 μm; the pore width, $L_w$, is in the range of about 1 nm to 25 μm, e.g., about 500 nm to 1 μm. In implementations, the ratio of the volume of pores to the total volume of the surface region, or porosity of the surface 140 is about 90% or less (e.g., about 80%, about 70%, about 60%, about 50% or less). Alternatively or additionally, the inward surface 150 of stent body 23 can also have a porous structure. In some implementations, the porous surface 140 is formed by plasma treatment, such as plasma immersion ion implantation ("PIII") as is described in details below.

Referring particularly to FIGS. 2C and 2D, in some implementations, the second material 180 and hollow spheres are a ceramic material (e.g., SiOx, or IrOx). The outer diameter of the hollow spheres 160 is preferably smaller than or comparable to the pore dimensions (width and depth) of the porous region of surface 140. For example, the outer diameter, $D_o$, is about 10 nm to 5 μm, e.g., 100 nm to 1 μm. The inner diameter, $D_i$, of the hollow spheres 160 ranges from about 1 nm to 5 μm, e.g., 20 nm to 500 nm. Thickness, $D_t$, of the sphere wall 240 can range from 1 nm to 1 μm, e.g., 10 nm to 500 nm and it may or may not be uniform along the radial axes. In implementations, the wall 240 has a porous structure. In preferred implementations, wall 240 has an open-cell porous structure, so that the pores 260 in wall 240 are interconnected and serve as passageways between the interior and the exterior of the hollow spheres 160. The width of pores 260, $I_w$, varies from about 0.5 nm to 500 nm, e.g., 1 nm to 100 nm. In implementations, the second material coating 180 has substantially the same porous structure as the sphere wall 240 described above, and thickness of the coating 180 varies from about 1 nm to 2 μm, e.g., 10 nm to 1500 nm. A particular ceramic is IROX, which can have therapeutic benefits such as enhancing endothelialization. IROX and other ceramics are discussed further in Alt et al., U.S. Pat. No. 5,980,566. Suitable ceramics also include metal oxides, oxides and transition metal oxides (e.g. oxides of titanium, zirconium, hafnium, tantalum, molybdenum, tungsten, thenium, and iridium; silicon; silicon-based ceramics, such as those containing silicon nitrides, silicon carbides and silicon oxides (sometimes referred to as glass ceramics); calcium phosphate ceramics (e.g. hydroxyapatite); carbon and carbon-based, ceramic-like materials such as carbon nitrides. In implementations, the second material and sphere are provided through a sol-gel reaction assisted with the use of spherical sacrificial templates (described below).

Figure 3:
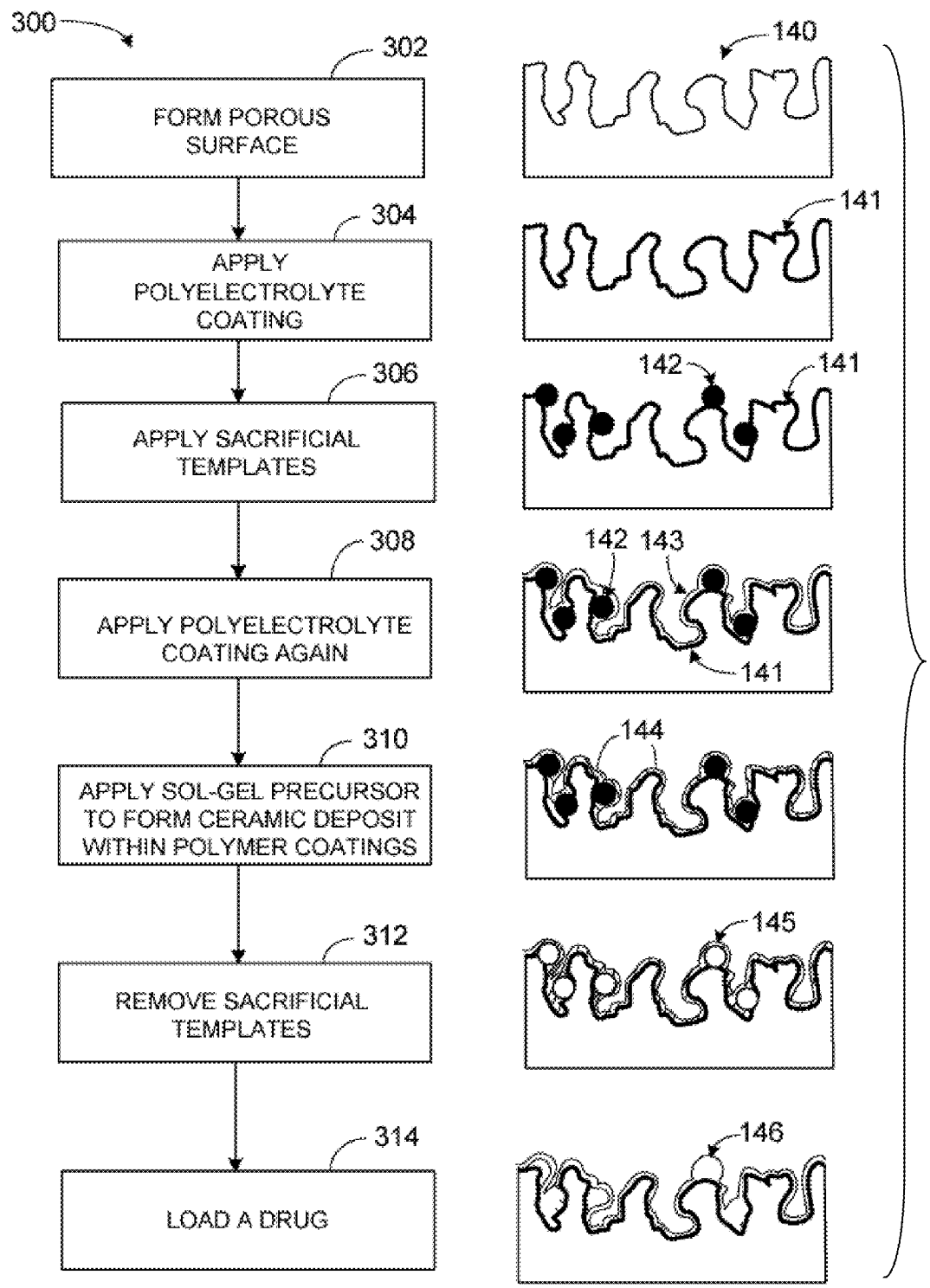
FIG. 3 is a flow chart and illustration of an implementation of a method of making a stent.

Referring to FIG. 3, a method 300 of making and coating porous surface 140 is described and illustrated. The left side of this figure provides a flow diagram of processing steps and the right side provides a cross-sectional schematic of a region of the stent at the corresponding processing steps. The method 300 includes forming a porous surface (step 302), applying a polyelectrolyte layer (step 304), applying sacrificial templates, e.g., templating polystyrene spheres (step 306), applying another polyelectrolyte layer (step 308), forming ceramic deposit within each polyelectrolyte layer (step 310), removing polyelectrolyte layers and sacrificial templates to form a porous ceramic coating integrated with hollow ceramic spheres which have porous walls and cavities on surface 140 (step 312), and loading the cavities with a therapeutic agent or drug (step 314). In some implementations, one or more polyelectrolyte layers are applied to the surface 140 and/ or sacrificial templates, and the thickness of the polyelectrolyte layers influence the final thickness of the ceramic coating.

In step 302, the porous structure of surface 140 can be formed by plasma treatment, chemical etching, or electrochemical processes. In some implementations, plasma immersion ion implantation ("PIII") is applied. During PIII, one or more charged species in a plasma, such as an argon plasma, are accelerated at high velocity toward a substrate, e.g., a stent or a stent precursor ("pre-stent") such as a metal tube. Acceleration of the charged species, e.g., particles, of the plasma towards the pre-stent is driven by a pulsed electrical potential difference between the plasma and the pre-stent. Alternatively, the electrical potential difference can be applied between the plasma and an electrode that is underneath the pre-stent such that the pre-stent is in a line-of-sight. Upon impact with the outward surface and/or inward surface of the pre-stent, the charged species, due to their high velocity, penetrate a distance into the stent, interact with the first material, e.g., displace atoms and/or knock atoms out of the first material and form porous structures in the surface. The penetration depth is being controlled, at least in part, by the potential difference between the plasma and the stent. Other factors such as dose-rate, process temperature, and ion type can be selected to control the porous structure of the surface. An implementation of PIII system is described further below.

In steps 304, 306, and 308, after the porous surface is formed, charged layers containing polyelectrolytes and sacrificial templates are assembled upon the surface, using a layer-by-layer ("LBL") technique in which the layers electrostatically self-assemble. In the LBL technique, a first layer having a first net surface charge is deposited on an underlying substrate, followed by a second layer having a second net surface charge that is opposite in sign to the net surface charge of the first layer. Thus, the charge on the outer layer is reversed upon deposition of each sequential layer. Additional first and second layers can then be alternatingly deposited on the substrate to build multi-layered structure to a predetermined or targeted thickness. For example, in steps 304 and 308, deposited layers 141 and 143 can either be a polyelectrolyte monolayer or polyelectrolyte multilayers ("PEM") with thickness ranging from 0.3 nm to 1 µm, e.g., 1 nm to 500 nm. In an intermediate layer between 141 and 143, charged sacrificial templates 142, e.g., polystyrene spheres, polymethylmethacrylate ("PMMA"), or silica templates , with net surface charges opposite in sign to those of layers 141 and 143, are deposited (step 306).

In certain implementations, the LBL assembly can be conducted by exposing a selected charged substrate (e.g., stent) to solutions or suspensions that contain species of alternating net charge, including solutions or suspensions that contain charged templates (e.g., polystyrene spheres), polyelectrolytes, and, optionally, charged therapeutic agents. The concentration of the charged species within these solutions and suspensions, which can be dependent on the types of species being deposited, can range, for example, from about 0.01 mg/mL to about 100 mg/mL (or to about 50 mg/mL, or to about 30 mg/mL). The pH of these suspensions and solutions can be such that the templates, polyelectrolytes, and optional therapeutic agents maintain their charge. Buffer systems can be used to maintain charge. The solutions and suspensions containing the charged species (e.g., solutions/suspensions of templates, polyelectrolytes, or other optional charged species such as charged therapeutic agents) can be applied to the charged substrate surface using a variety of techniques. Examples of techniques include spraying techniques, dipping techniques, roll and brush coating techniques, techniques involving coating via mechanical suspension such as air suspension, ink jet techniques, spin coating techniques, web coating techniques and combinations of these processes. Layers can be applied over an underlying substrate by immersing the entire substrate (e.g., stent) into a solution or suspension containing the charged species, or by immersing half of the substrate into the solution or suspension, flipping the same, and immersing the other half of the substrate into the solution or suspension to complete the coating. In some implementations, the substrate is rinsed after application of each charged species layer, for example, using a washing solution with a pH that maintains the charge of the outer layer. In others, the substrate can be dried between applications.

The sacrificial template objects include polymeric spheres, silica spheres, nanoparticles, carbon fibers, polymeric fibers, polymer drug conjugates or carbon nanotubes The sacrificial templates described herein can have selected shapes, e.g., shapes of a sphere, a cube, a rod, a fiber, a spindle, a solid layer, or a tube, etc. Sacrificial templates are templates capable of being removed once a desired configuration, often complementary to the shape of the templates, is achieved. In some implementations, the templates are completed removed once the complementary configurations are created. In other implementations, the templates are at least partially maintained in the final product. For example, carbon fibers and carbon nanotubes can be kept within the final configurations as a reinforcing component. In a particular implementation, spherical sacrificial templates, e.g., polystyrene spheres, are used. When polystyrene spheres are applied as templates, a structure with spherical cavities or a hollow structure will be obtained after the polystyrene spheres are removed. In implementations, polystyrene spheres have a diameter of about 10 nm to 10 µm, e.g., about 20 nm to 500 nm. Suitable polystyrene spheres are available from Microparticles GmbH, Research- and Development Laboratory, Volmerstrasse 9A, UTZ, Geb.3.5.1, D-12489 Berlin. Other suitable templates include melamine formaldehyde (MF), poly-DL-lactic acid (PLA), cubic sodium chloride and truncated rhombohedral sugar crystallites. The latter two are as well an example of template shapes that are not round, but in this case have the shape of crystals. Living cells such as red blood cells and bacteria can be used as templates. The template is burned away during a calcination step, similar to the removal of the simple polystyrene templates. Encapsulation of cells is discussed in Yu et al., *Biomaterials* 25 (2004) 3655-3802. In particular implementations, sacrificial templates can be pre-treated with polyelectrolytes via LBL assembly to have a PEM coating. Next, the PEM-coated templates can be suspended or dissolved in a solvent and be applied to a substrate. When PEM-coated templates are used, step 308 is optional. In further implementations, sacrificial templates with different PEM coating and/or different thickness of PEM coating can be applied to a common stent, e.g., to create hollow structures at different portions of the stent with different wall thicknesses so that various drug eluting profiles at different portions of the stent can be achieved.

Polyelectrolyte are polymers having charged (e.g., ionically dissociable) groups. The number of these groups in the polyelectrolytes can be so large that the polymers are soluble in polar solvents (including water) when in ionically dissociated form (also called polyions). Depending on the type of dissociable groups, polyelectrolytes can be classified as polyacids and polybases. When dissociated, polyacids form polyanions, with protons being split off. Polyacids include inorganic, organic and biopolymers. Examples of polyacids are polyphosphoric acids, polyvinylsulfuric acids, polyvinylsulfonic acids, polyvinylphosphonic acids and polyacrylic acids. Examples of the corresponding salts, which are called polysalts, are polyphosphates, polyvinylsulfates, polyvinylsulfonates, polyvinylphosphonates and polyacrylates. Polybases contain groups that are capable of accepting protons, e.g., by reaction with acids, with a salt being formed. Examples of polybases having dissociable groups within their backbone and/or side groups are polyallylamine, polyethylimine, polyvinylamine and polyvinylpyridine. By accepting protons, polybases form polycations. Some polyelectrolytes have both anionic and cationic groups, but nonetheless have a net positive or negative charge.

The polyelectrolytes can include those based on biopolymers. Examples include alginic acid, gum arabicum, nucleic acids, pectins and proteins, chemically modified biopolymers such as carboxymethyl cellulose and lignin sulfonates, and synthetic polymers such as polymethacrylic acid, polyvinylsulfonic acid, polyvinylphosphonic acid and polyethylenimine. Linear or branched polyelectrolytes can be used. Using branched polyelectrolytes can lead to less compact polyelectrolyte multilayers having a higher degree of wall porosity. In some implementations, polyelectrolyte molecules can be cross linked within or/and between the individual layers, to enhance stability, e.g., by cross linking amino groups with aldehydes. Furthermore, amphiphilic polyelectrolytes, e.g., amphiphilic block or random copolymers having partial polyelectrolyte character, can be used in some implementations to affect permeability towards polar small molecules.

Other examples of polyelectrolytes include low-molecular weight polyelectrolytes (e.g., polyelectrolytes having molecular weights of a few hundred Daltons up to macromolecular polyelectrolytes (e.g., polyelectrolytes of synthetic or biological origin, which commonly have molecular weights of several million Daltons). Still other examples of polyelectrolyte cations (polycations) include protamine sulfate polycations, poly(allylamine) polycations (e.g., poly(allylamine hydrochloride) (PAH)), polydiallyldimethylammonium polycations, polyethyleneimine polycations, chitosan polycations, gelatin polycations, spermidine polycations and albumin polycations. Examples of polyelectrolyte anions (polyanions) include poly(styrenesulfonate) polyanions (e.g., poly(sodium styrene sulfonate) (PSS)), polyacrylic acid polyanions, sodium alginate polyanions, eudragit polyanions, gelatin polyanions, hyaluronic acid polyanions, carrageenan polyanions, chondroitin sulfate polyanions, and carboxymethylcellulose polyanions.

Still more examples of polyelectrolytes and LBL assembly are disclosed in commonly assigned U.S. Ser. No. 10/985,242, U.S. application publicly available through USPTO Public Pair, and Lefaux et al., "Polyelectolyte Spin Assembly: Influence of Ionic Strength on the Growth of Multilayered Films," J Polm Sci Part B: Polym Phys 42, Wiley Periodicals, Inc.; 3654-3666, 2004, the entire disclosure of which is incorporated by reference herein.

In step 310, a precursor solution for a consequent in situ sol-gel reaction is applied to the stent surface with deposited layers 141, 142, and 143. The solution permeates the polyelectrolyte layers 141 and 143, and those of spheres 142 if they are pretreated with PEM. Then an in situ sol-gel reaction can take place within the interstices of polyelectrolytes.

An exemplary solution is a mixture of ethanol, a precursor (e.g., tetraethylorthosilicate or TEOS, titanium isopropoxide, iridium acetylacetonate, and etc.) with the molar ratio of ethanol to precursor ranging from about 1 to 16, and sometimes a small amount of water. A sol-gel reaction occurs when the precursor comes into contact with water molecules that hydrate or get trapped in the interstices of polyelectrolytes and decomposes to form a gel or a ceramic deposit 144 within the PEMs. Alternatively or additionally, the high charge density of polyelectrolytes attract water molecules out of the precursor solution, and as a result, the local water content increases to such an extent that a sol-gel reaction or hydrolysis takes place and produces a gel or ceramic deposit around the polyelectrolytes, i.e., within the PEMs. For example, when an in situ reaction of a sol-gel solution of TEOS in pure ethanol with 15 wt. % water is carried out, the polyelectrolyte layers attract water because of their ionic charge, and their water content increases above 15 wt. %, thus activating the sol-gel reaction. This method is very controlled and stops automatically once the layers are saturated and charge density decreases. Other precursors can be used for the ceramic materials, e.g. including alkoxx silanes, titanium alkoxides, and iridium diketonates. Examples of sol-gel process are provided, e.g., in Weber et al., U.S. Provisional Application No. 60/884,471, filed Sep. 14, 2006; Maehara et al., *Thin Solid Films* 438-39:65-69, 2003; Kim et al., *Thin Solid Films* 499:83-89, 2003; and Bu et al., *J. Europ. Cer. Soc.* 25:673-79, 2005.

In step 312, the polyelectrolytes, and templating spheres are removed after the ceramic deposit forms within the PEMs. In some implementations, by applying calcination or pyrolysis processes, the polyelectrolytes and templating spheres can be removed, and the ceramic deposit 144 within the PEMs can be simultaneously transformed into a crystalline or amorphous ceramic coating 145 with a porous structure and hollow ceramic spheres integrated with the coating. In a particular implementation, a coated stent which has been processed through step 310 is air dried and then fired in an oxidizing atmosphere (e.g., 20% $O_2$ and 80% Ar in volume) to a high temperature (e.g., 300 to 700° C.) to remove all the polymeric and/or organic compounds, including the polystyrene spheres, and to convert the gel into an oxide or ceramic material. The porous structure of the ceramic coating and walls of the hollow ceramic spheres (see, e.g., FIG. 2D) can be predetermined by controlling the selection of polyelectrolytes, pH value, ionic strength, or the removing process conditions. For example, tense porous structure (e.g., smaller pores and low porosity) of the ceramic material forms in acidic conditions while loose porous structure forms in basic conditions. Moreover, since the ceramic deposit forms through out the entire PEMs, and as a consequence, the thickness of the ceramic coating and walls of the hollow spheres are linearly depend upon that of the corresponding PEMs. In other implementations, removing processes utilizing wet etching or UV light exposure are applied. In some implementations, to avoid the use of high temperatures, in step 312, PEMs and/or sacrificial template can be removed by longterm exposure to an agitated aqueous solution with high salt concentrations at room temperature. In yet some other implementations, to avoid the use of high temperatures, in step 312, a non-polyelectrolyte compound, such as nonsurfactants, e.g., glucose, fructose, or urea, can be used to generate the porous ceramic coatings, as disclosed in Zheng et al., J. Sol-Gel Science and Tech. 24:81-88, 2002. Glucose or urea can be removed with use of water at room temperature to leave behind a pure porous ceramic coating. Similar to that of the polyelectrolytes, selection of the non-polyelectrolyte compound can generate materials with different pore sizes, thus allowing generation of a required drug release profile. For example, urea leaves larger pores than glucose. Because many nonsurfactants are biocompatible, they can also be allowed to remain in the sol-gel layer until they bioerode in the body after delivery of the stent. In implementations, templates can be removed by selective etching.

In step 314, in some implementations, a pharmaceutically active agent or drug 146 can be loaded into the cavities of hollow spheres within the ceramic coating. The drug can be loaded by repeated cycles of soaking and drying the ceramic coating. In implementations, conditions may be applied to facilitate drug load, e.g., a supercritical fluid can be applied as a solvent during this process. For example, a drug can be loaded first using a solvent, e.g., a super critical fluid (carbon dioxide with a co-solvent, ethanol, of 10% by weight), which penetrates the walls of the hollow spheres. If the loading process results in drug deposition in both the inside and the outside of the spheres, the drug deposit of the outside can later be removed by rinsing the spheres with a solvent that is unable to penetrate the sphere walls, e.g., dimethyl sulfoxide (DMSO). In other implementations, a drug can be loaded prior to the removal of the polymeric components and templates. In other words, step 314 can precede 312 (e.g., precede 310, 308, 306 or 304), in which case, a low temperature process in step 312 as discussed above is preferred. In particular implementations, a drug-polymer conjugate is applied instead of the drug itself, e.g. a conjugate of a polymer deposited in the LBL steps. In some implementations, the drug can be loaded within the pores of the ceramic coating and the walls of hollow spheres. The stent can further include more than one therapeutic agent by having more than one drug within each hollow element, or by having different drugs in different hollow elements.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be nonionic, or they can be anionic and/or cationic in nature. Therapeutic agents can be used singularly, or in combination. Preferred therapeutic agents include inhibitors of restenosis (e.g., paclitaxel), immunosuppressants(e.g., everolimus, tacrolimus, or sirolimus), anti-proliferative agents (e.g., cisplatin), and antibiotics (e.g., erythromycin). Additional examples of therapeutic agents are described in U.S. Published Patent Application No. 2005/0216074. Polymers for drug elution coatings are also disclosed in U.S. Published Patent Application No. 2005/019265A.

Figure 4:
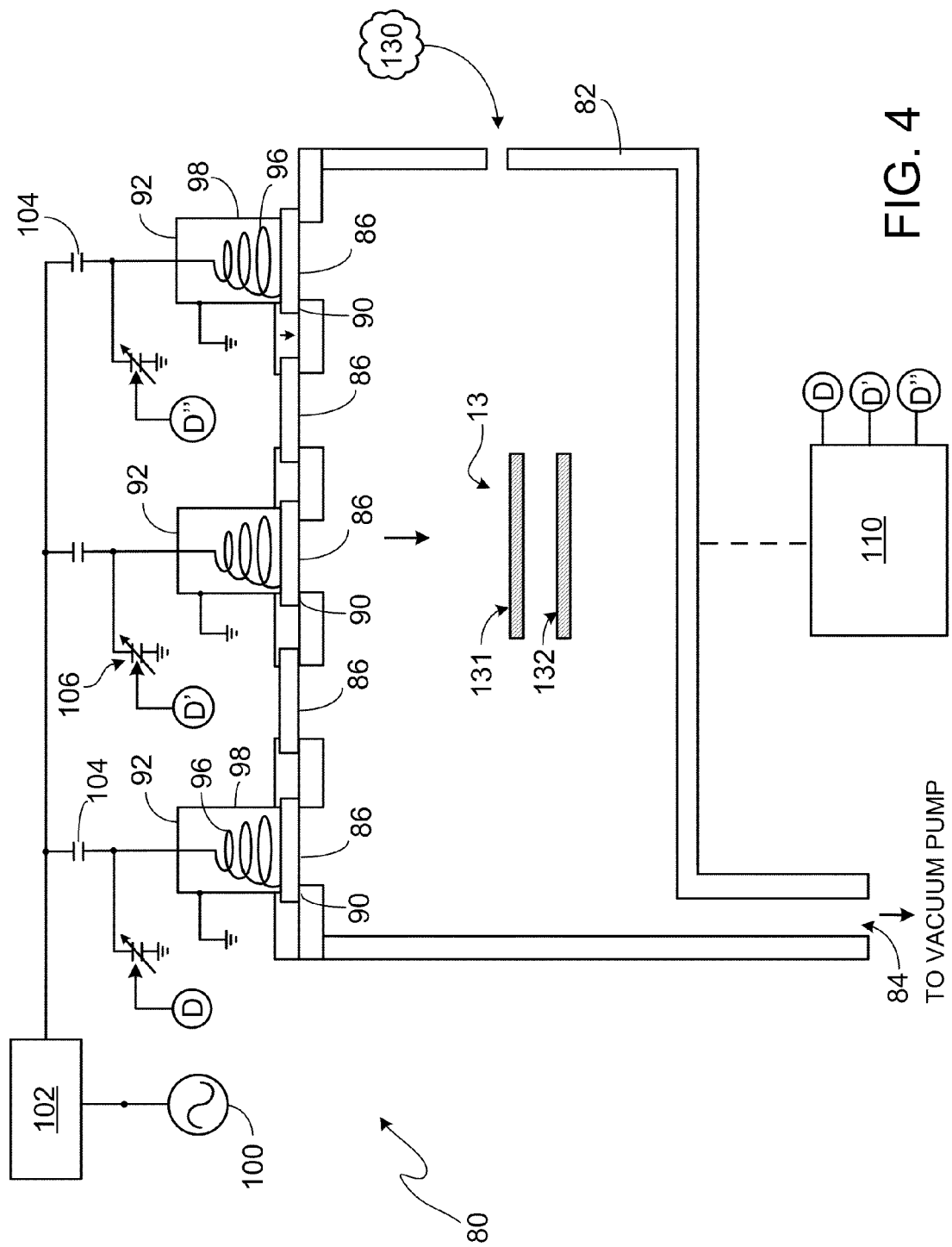
FIG. 4 is a schematic cross-sectional view of a plasma immersion ion implantation ("PIII") system.

Referring to FIG. 4, an implementation of a PIII processing system is shown. System 80 includes a vacuum chamber 82 having a vacuum port 84 connected to a vacuum pump and a gas source 130 for delivering a gas, e.g., argon, helium, xenon, oxygen, or nitrogen, to chamber 82 to generate a plasma. System 80 includes a series of dielectric windows 86, e.g., made of glass or quartz, sealed by o-rings 90 to maintain a vacuum in chamber 82. Removably attached to some of the windows 86 are radio frequency ("RF") plasma sources 92, each source having a helical antenna 96 located within a grounded shield 98. The windows without attached RF plasma sources are usable, e.g., as viewing ports into chamber 82. Each antenna 96 electrically communicates with an RF generator 100 through a network 102 and a coupling capacitor 104. Each antenna 96 also electrically communicates with a tuning capacitor 106. Each tuning capacitor 106 is controlled by a signal D, D', D" from a controller 110. By adjusting each tuning capacitor 106, the output power from each RF antenna 96 can be adjusted to maintain homogeneity of the generated plasma.

In use, a plasma is generated in chamber 82 and accelerated to a pre-stent 13. Pre-stent 13 can be made, for example, by forming a tube including the conventional metallic material and laser cutting a stent pattern in the tube, or by knitting or weaving a tube from a metallic wire or filament. A gas, such as argon, is introduced from gas source 130 into chamber 82, where a plasma is generated. The charged species in the generated plasma, e.g., an argon plasma, are accelerated toward all portions of pre-stent 13, including exterior 131 and interior portions 132 of the pre-stent, and thus, bombard the surface of the pre-stent. PIII is described by Chu, U.S. Pat. No. 6,120,660; Brukner, Surface and Coatings Technology, 103-104, 227-230 (1998); and Kutsenko, Acta Materialia, 52, 4329-4335 (2004), the entire disclosure of each of which is incorporated by reference herein.

The configuration of the porous stent surface formed is controlled in the PIII process by tuning the ion penetration depth and ion concentration through selection of the type of ion, the ion energy and ion dose. For example, when the ions have a relatively low energy, e.g., 10 kiloelectronvolts ("keV") or less, penetration depth is relatively shallow when compared with the situation when the ions have a relatively high energy, e.g., greater than 40 keV. In some implementations, the potential difference can be greater than 10 kilovolts ("kV"), e.g., greater than 20 kV, greater than 40 kV, greater than 50 kV, greater than 60 kV, greater than 75 kV, or even greater than 100 kV. The ion dosage being applied to a surface can range from about $1 \times 10^{14}$ ions/cm$^2$ to about $1 \times 10^{19}$ ions/cm$^2$, e.g., from about $1 \times 10^{15}$ ions/cm$^2$ to about $1 \times 10^{18}$ ions/cm$^2$.

EXAMPLE

In this particular implementation, a 316L stainless steel coupon is treated with Ar$^+$ ions having an energy of 35 keV and a dosage of $2.0 \times 10^{17}$ ion/cm$^2$ in a PIII setup with following operation parameters: argon gas; base pressure about $2 \times 10^{-5}$ Pa; argon pressure about 0.2 Pa; RF power about 200W with 5 µs pulse; number of pulses: $4 \times 10^6$ pulses; process duration around 2 hours, and substrate temperature 280°

Figure 5A:
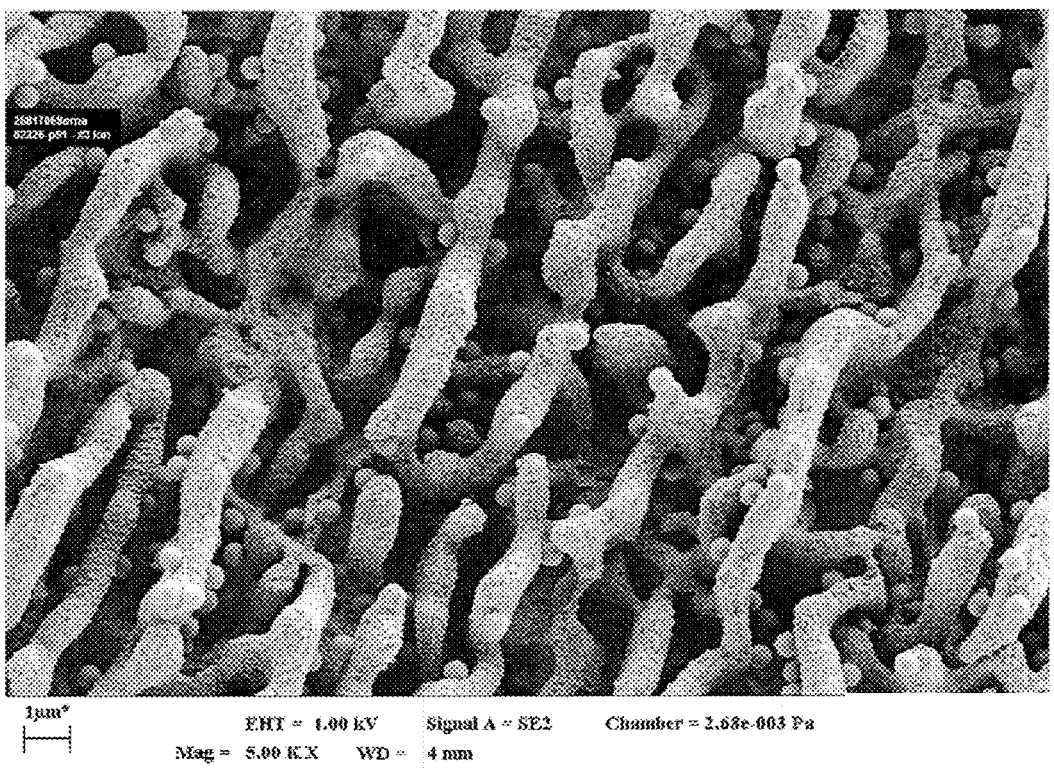
FIGS. 5A-5C are FESEM pictures of some implementations of the disclosure.
Figure 5B:
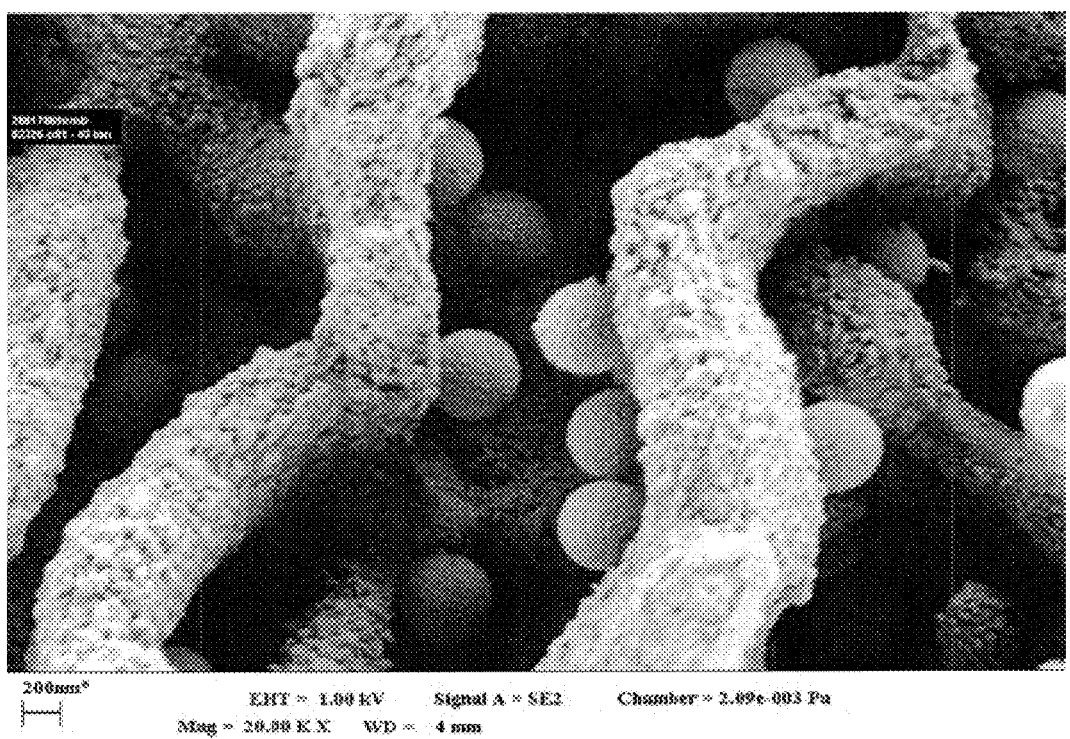
Figure 5C:
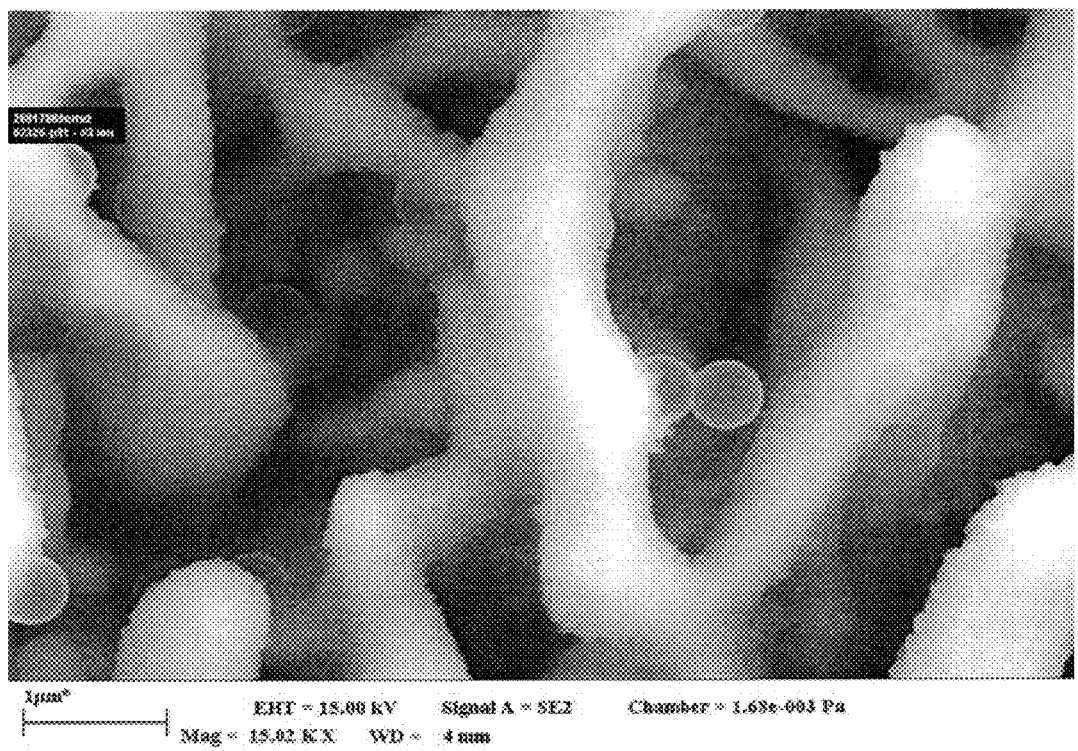

C. The ion-bombarded coupon is then coated with four polyelectrolyte layers: PAH/PSS/PAH/PSS, using a first solution of 0.2M PSS salt ($NH_3/NH_4Cl$ buffer of pH 9), and a second solution of 1 mg /mL PAH; 0.2M NaCl; 0.05M sodium acetate buffer solution with pH being 5 to 6, e.g. pH=5.6. Ionic strength can be adjusted with Neal, see Lefaux et al., supra. Each layer is deposited by submerging the sample in the respective solution for 20 minutes, followed by rinsing with water three times before depositing another layer until the layer structure is (PAH/PSS/PAH/PSS/PAH/PSS/PAH/PSS/PAH/PSS/PAH). The coupon was then submerged in a Polystyrene sphere solution, 5 wt %, 500 nm diameter, for an hour and then rinsed 3 times with DI water. Additional PEM layers were added to after the spheres of (PAH/PSS/PAH/PSS). Each layer was deposited over 20 minutes and then rinsed three times with DI water. Subsequently, the PEM-coated coupon is placed into a sol-gel solution of 1 g TEOS in 50 mL ethanol, with 5 mL water and 0.5 mL 25 wt. % NH4OH and kept there for ~16 hours before it is retrieved. The coupon was rinsed three times in DI water. As a final step, the gel/PEM-coated coupon is placed in a tube furnace and calcined in air at 540° C. for 4.5 hours, ramping up at a rate of 360° C./hour from room temperature, total oven time ~6 hrs. The sample was allowed to cool in the oven overnight until it reached room temperature. Referring to FIGS. 5A-5C, Field Emission Scanning Electron Microscopy ("FESEM") images of the surface of a 316L stainless steel coupon processed with the method disclosed in FIG. 3 are shown. As shown in FIG. 5A, ceramic spheres are bound to a ceramic coating which almost conformally overlies the porous or corrugated surface of the coupon. Referring to FIG. 5B, a further magnified FESEM image, porous features of the ceramic coating and ceramic spheres are move visible. Referring to FIG. 5C, which was taken at a higher electron accelerating voltage (e.g., 15 kV), the ceramic spheres are hollow.

In further implementations, the hollow elements and/or ceramic coating may incorporate magnetic particles, e.g., nanoparticles, loosely sitting in the cavities by applying sacrificial templates with magnetic kernels which remain in the ceramic material after templating material is removed. The implementations may have one or more additional following advantages, including that the release profile of a therapeutic agent from an endoprosthesis, e.g., a ceramic coated stent, can be controlled through non-invasive means, e.g., a magnetic field. The magnetic field can be used to selectively agitate the particles, to modify the porosity of the ceramic. Use of magnetic particles is described further in U.S. Provisional Application No. 60/845,136, filed Sep. 15, 2006.

In some implementations, after the forming hollow spheres inside of the porous surface generated by e.g. PIII and filling them with a drug, an additional material can be applied to fill the remaining space in the porous surface, for example, a bioerodible polymer (PLGA, PLLA) (with or without an additional drug load), or a highly porous sol-gel layer prepared at low temperature, e.g., at room temperature.

The stents described herein can be configured for vascular, e.g. coronary and peripheral vasculature or non-vascular lumens. For example, they can be configured for use in the esophagus or the prostate. Other lumens include biliary lumens, hepatic lumens, pancreatic lumens, uretheral lumens and ureteral lumens.

Any stent described herein can be dyed or rendered radio-opaque by addition of, e.g., radio-opaque materials such as barium sulfate, platinum or gold, or by coating with a radio-opaque material. In implementations, the porous structure can be formed directly on the stent body, as described above, or the porous structure can be formed in a coating over the stent body. The coating may be, e.g., a radio-opaque metal. The stent can include (e.g., be manufactured from) metallic materials, such as stainless steel (e.g., 316L, BioDur® 108 (UNS S29108), and 304L stainless steel, and an alloy including stainless steel and 5-60% by weight of one or more radio-paque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain implementations, a coronary stent can have an expanded diameter of from about 2 mm to about 6 mm. In some implementations, a peripheral stent can have an expanded diameter of from about 4 mm to about 24 mm. In certain implementations, a gastrointestinal and/or urology stent can have an expanded diameter of from about 6 mm to about 30 mm. In some implementations, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., U.S. Pat. No. 6,290,721).

Medical articles include articles for exterior application to the body such as patches for delivery of therapeutic agent to intact skin and broken skin (including wounds) and implantable or insertable devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglilmi detachable coils and metal coils), septal defect closure devices, drug depots that are adapted for placement in an artery for treatment of the portion of the artery distal to the device, myocardial plugs, patches, pacemakers, leads including pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other devices that are implanted or inserted into the body.

All publications, patent applications, patents, and other references mentioned herein are incorporated by reference herein in their entirety.

Still further implementations are in the following claims.

What is claimed is:

1. An endoprosthesis, comprising:
   a surface, the surface comprising a surface porous structure of a first material, the surface porous structure defining pores and being corrugated;
   a coating of a second material on the surface porous structure; and
   a plurality of hollow elements, at least some of the hollow elements being formed in one or more of the pores of the surface porous structure, and at least some of the hollow elements each comprising a wall formed of the second material and comprising a portion of a continuous part of the coating, the wall defining an interior space, the interior space containing a therapeutic agent.

2. The endoprosthesis of claim 1, wherein the first material comprises a metal.

3. The endoprosthesis of claim 1, wherein the second material comprises a ceramic material.

4. The endoprosthesis of claim 3, wherein the ceramic material comprises silicon oxide, titanium oxide, iridium oxide or a mixture thereof.

5. The endoprosthesis of claim 1, wherein the wall defining the interior space comprises a wall porous structure.

6. The endoprosthesis of claim 5, wherein the wall porous structure defines a plurality of pores each having a width of about 0.5 nm to about 500 nm.

7. The endoprosthesis of claim 1, wherein the pores of the surface porous structure have a width and a depth of about 1 nm to about 25 µm.

8. The endoprosthesis of claim 1, wherein the hollow elements are hollow spheres.

9. The endoprosthesis of claim 8, wherein the hollow spheres have an outer diameter of about 10 nm to about 5 µm.

10. The endoprosthesis of claim 1, wherein the coating of the second material has a thickness of about 1 nm to about 1 µm.

11. The endoprosthesis of claim 1, wherein the endoprosthesis has a body formed of the first material.

12. The endoprosthesis of claim 5, wherein the wall porous structure comprises interconnected pores defining passageways in communication between interior and exterior of the hollow elements.

* * * * *

UNITED STATES PATENT AND TRADEMARK OFFICE
CERTIFICATE OF CORRECTION

PATENT NO.       : 8,449,603 B2
APPLICATION NO.  : 12/486295
DATED            : May 28, 2013
INVENTOR(S)      : Jan Weber, Liliana Atanasoska and Michele Zoromski It is certified that error appears in the above-identified patent and that said Letters Patent is hereby corrected as shown below:

On the Title Page, Item (56),

Page 11, Col. 2, (Other Publications), Line 1 Delete "Polythylene" and insert -- Polyethylene --, therefor.

Page 11, Col. 2, (Other Publications), Line 39 Delete "iridiumoxyd" and insert -- iridiumoxide --, therefor.

Page 11, Col. 2, (Other Publications), Line 41 Delete "iridiumoxyd" and insert -- iridiumoxide --, therefor.

Page 12, Col. 1, (Other Publications), Line 18 Delete "Rhotoelectron" and insert -- Photoelectron --, therefor.

Page 12, Col. 1, (Other Publications), Line 42 Delete "A1203/" and insert -- Al2O3/ --, therefor.

Page 12, Col. 1, (Other Publications), Line 48 Delete "nonopouros" and insert -- nonoporous --, therefor.

Page 12, Col. 1, (Other Publications), Line 55 Delete "Electrochemisty" and insert -- Electrochemistry --, therefor.

Page 12, Col. 1, (Other Publications), Line 70 Delete "Saphire" and insert -- Sapphire --, therefor.

Page 12, Col. 1, (Other Publications), Line 71 Delete "Reaserch" and insert -- Research --, therefor.

Signed and Sealed this
Twenty-eighth Day of July, 2015

Michelle K. Lee
*Director of the United States Patent and Trademark Office*

CERTIFICATE OF CORRECTION (continued)
U.S. Pat. No. 8,449,603 B2

Page 12, Col. 1, (Other Publications), Line 71 Delete "Southhampton" and insert -- Southampton --, therefor.

Page 12, Col. 2, (Other Publications), Line 4 Delete "activites:" and insert -- activities: --, therefor.

Page 12, Col. 2, (Other Publications), Line 62 Delete "Chemisty," and insert -- Chemistry, --, therefor.

Page 12, Col. 2, (Other Publications), Line 66 Delete "Polythylene" and insert -- Polyethylene --, therefor.

Page 13, Col. 1, (Other Publications), Line 26 Delete "Surgury," and insert -- Surgery, --, therefor.

Page 13, Col. 1, (Other Publications), Line 43 Delete "compatiblity" and insert -- compatibility --, therefor.

Page 13, Col. 1, (Other Publications), Line 50 Delete "Oxie" and insert -- Oxide --, therefor.

Page 13, Col. 2, (Other Publications), Line 17 Delete "Rolyal" and insert -- Royal --, therefor.

Page 13, Col. 2, (Other Publications), Line 29 Delete ".edu-tjy107/" and insert -- .edu/~tjy107/ --, therefor.

Page 14, Col. 1, (Other Publications), Line 6 Delete "applicatio" and insert -- application --, therefor.

Page 14, Col. 1, (Other Publications), Line 9 Delete "inprove" and insert -- improve --, therefor.

Page 14, Col. 1, (Other Publications), Line 20 Delete "page_1.html)." and insert -- page_1.html). --, therefor.

Page 14, Col. 1, (Other Publications), Line 21 Delete ""Innovatice" and insert -- Innovative --, therefor.

Page 14, Col. 1, (Other Publications), Line 23 Delete "page_.html)." and insert -- page_1.html). --, therefor.

Page 14, Col. 1, (Other Publications), Line 25 Delete "/dmggd/" and insert -- /druggd/ --, therefor.

Page 14, Col. 1, (Other Publications), Line 25-26 Delete "page_1.html)." and insert -- page_1.html). --, therefor.

CERTIFICATE OF CORRECTION (continued)

Page 14, Col. 1, (Other Publications), Line 36 Delete "of" and insert -- "Characterization of --, therefor.

Page 14, Col. 1, (Other Publications), Line 36-37 Delete "imrnunoisolation" and insert -- immunoisolation --, therefor.

Page 14, Col. 1, (Other Publications), Line 49 Delete "angographic" and insert -- angiographic --, therefor.

Page 14, Col. 1, (Other Publications), Line 59 Delete "Suppliment" and insert -- Supplement --, therefor.

Page 14, Col. 1, (Other Publications), Line 60 Delete "Poly(Methly" and insert -- Poly(methyl --, therefor.

Page 14, Col. 1, (Other Publications), Line 71 Delete "PDEPTand" and insert -- PDEPT and --, therefor.

Page 14, Col. 1, (Other Publications), Line 72 Delete "principals" and insert -- principles --, therefor.

Page 14, Col. 2, (Other Publications), Line 18 Delete "laster" and insert -- laser --, therefor.

Page 14, Col. 2, (Other Publications), Line 22 Delete "nonoporosity" and insert -- nanoporosity --, therefor.

Page 14, Col. 2, (Other Publications), Line 71 Delete "propoerties" and insert -- properties --, therefor.

Page 15, Col. 1, (Other Publications), Line 35 Delete "attachmend" and insert -- attachment --, therefor.

Page 15, Col. 1, (Other Publications), Line 43 Delete "nanopourous" and insert -- nanoporous --, therefor.

Page 15, Col. 1, (Other Publications), Line 54 Delete "unitrastructure" and insert -- ultrastructure --, therefor.

Page 15, Col. 2, (Other Publications), Line 21 Delete "NaC1" and insert -- NaCl --, therefor.

Page 15, Col. 2, (Other Publications), Line 35 Delete "Mg(Oh)2/Mg0" and insert -- Mg(OH)2/MgO --, therefor.

Page 15, Col. 2, (Other Publications), Line 48 Delete ""Pourous" and insert -- "Porous --, therefor.

CERTIFICATE OF CORRECTION (continued)
U.S. Pat. No. 8,449,603 B2

Page 15, Col. 2, (Other Publications), Line 54 Delete "titaniaa" and insert -- titania --, therefor.

Page 15, Col. 2, (Other Publications), Line 71 Delete ""Prvention" and insert -- "Prevention --, therefor.

Page 16, Col. 1, (Other Publications), Line 9 Delete "Systhesis" and insert -- Synthesis --, therefor.

Page 16, Col. 1, (Other Publications), Line 28 Delete "meterials" and insert -- materials --, therefor.

Page 16, Col. 1, (Other Publications), Line 54 Delete "Depostion,"" and insert -- Deposition," --, therefor.

Page 16, Col. 1, (Other Publications), Line 61 Delete "Efect" and insert -- Effect --, therefor.

Page 16, Col. 2, (Other Publications), Line 5 Delete "nanotechnolo ,"" and insert -- nanotechnology," --, therefor.

Page 16, Col. 2, (Other Publications), Line 27 Delete "/ampmar0 1 .html)." and insert -- /ampmar01.html). --, therefor.

Page 16, Col. 2, (Other Publications), Line 32 Delete "Chemisty," and insert -- Chemistry, --, therefor.

Page 16, Col. 2, (Other Publications), Line 58 Delete "polyelectolyte" and insert -- polyelectrolyte --, therefor.

Page 17, Col. 1, (Other Publications), Line 8 Delete "Gass" and insert -- Gas --, therefor.

Page 17, Col. 1, (Other Publications), Line 19 Delete "Chemisty" and insert -- Chemistry --, therefor.

Page 17, Col. 1, (Other Publications), Line 37 Delete "Presentaction" and insert -- Presentation --, therefor.

Page 17, Col. 1, (Other Publications), Line 42 Delete "etal.," and insert -- et al., --, therefor.

Page 17, Col. 1, (Other Publications), Line 63 Delete "Eelectrical" and insert -- Electrical --, therefor.

Page 17, Col. 1, (Other Publications), Line 63 Delete "Pakaging," and insert -- Packaging, --, therefor.

CERTIFICATE OF CORRECTION (continued)
U.S. Pat. No. 8,449,603 B2

Page 17, Col. 1, (Other Publications), Line 67 Delete "Americal" and insert -- American --, therefor.

Page 17, Col. 2, (Other Publications), Line 48 Delete "Septem" and insert -- Sept. --, therefor.

Page 18, Col. 1, (Other Publications), Line 10 Delete ""Electochemical" and insert -- "Electrochemical --, therefor.

Page 18, Col. 1, (Other Publications), Line 10 Delete "rithenium" and insert -- ruthenium --, therefor.

Page 18, Col. 1, (Other Publications), Line 22 Delete "Comunications," and insert -- Communications, --, therefor.

Page 18, Col. 1, (Other Publications), Line 24 Delete "Lamer" and insert -- Larner --, therefor.

Page 18, Col. 1, (Other Publications), Line 51 Delete "Strenght" and insert -- Strength --, therefor.

Page 18, Col. 1, (Other Publications), Line 71 Delete "nonopillars" and insert -- nanopillars --, therefor.

Page 18, Col. 1, (Other Publications), Line 71 Delete "partical" and insert -- particle --, therefor.

Page 18, Col. 2, (Other Publications), Line 21 Delete "haxagonal" and insert -- hexagonal --, therefor.

Page 18, Col. 2, (Other Publications), Line 34 Delete "adheasion" and insert -- adhesion --, therefor.

Page 18, Col. 2, (Other Publications), Line 70 Delete "ethyolene-vinyl" and insert -- ethylene-vinyl --, therefor.

Page 19, Col. 1, (Other Publications), Line 16 Delete "Evalution" and insert -- Evolution --, therefor.

Page 19, Col. 1, (Other Publications), Line 23 Delete "Oxforshire," and insert -- Oxfordshire, --, therefor.

Page 19, Col. 1, (Other Publications), Line 24 Delete ".corn/" and insert -- .com/ --, therefor.

Page 19, Col. 1, (Other Publications), Line 33 Delete "MatijeviO," and insert -- Matijevic, --, therefor.

CERTIFICATE OF CORRECTION (continued)
U.S. Pat. No. 8,449,603 B2

Page 19, Col. 1, (Other Publications), Line 34 Delete "Chemisty," and insert -- Chemistry, --, therefor.

Page 19, Col. 1, (Other Publications), Line 42 Delete "(htty://" and insert -- (http:// --, therefor.

Page 19, Col. 2, (Other Publications), Line 45 Delete "scafolding,"" and insert -- scaffolding," --, therefor.

Page 20, Col. 1, (Other Publications), Line 28 Delete "termperature" and insert -- temperature --, therefor.

Page 20, Col. 1, (Other Publications), Line 40 Delete "hardeningin" and insert -- hardening in --, therefor.

Page 20, Col. 1, (Other Publications), Line 61 Delete ""Advanaced" and insert -- "Advanced --, therefor.

Page 20, Col. 2, (Other Publications), Line 17 Delete "(TiN, TizAll-In)" and insert -- (TiN, $Ti_X Al1-_X N$) --, therefor.

Page 20, Col. 2, (Other Publications), Line 20 Delete "Mg0" and insert -- MgO --, therefor.

Page 20, Col. 2, (Other Publications), Line 65 Delete "Impantation,"" and insert -- Implantation," --, therefor.

Page 21, Col. 1, (Other Publications), Line 21 Delete "Interreactions" and insert -- Interactions --, therefor.

Page 21, Col. 1, (Other Publications), Line 48 Delete "pages1-14," and insert -- pages 1-14, --, therefor.

Page 21, Col. 1, (Other Publications), Line 52 Delete "Appiled" and insert -- Applied --, therefor.

Page 21, Col. 1, (Other Publications), Line 64 Delete "naosized" and insert -- nanosized --, therefor.

Page 21, Col. 1, (Other Publications), Line 69 Delete "nonoporous" and insert -- nanoporous --, therefor.

Page 21, Col. 2, (Other Publications), Line 1 Delete ""Soluable" and insert -- "Soluble --, therefor.

Page 21, Col. 2, (Other Publications), Line 7 Delete "Magnatron" and insert -- Magnetron --, therefor.

Page 21, Col. 2, (Other Publications), Line 15 Delete "(Deutche" and insert -- (Deutsche --, therefor.

Page 21, Col. 2, (Other Publications), Line 24 Delete "iridiumoxyd" and insert -- iridiumoxide --, therefor.

Page 21, Col. 2, (Other Publications), Line 26 Delete "iridiumoxyd" and insert -- iridiumoxide --, therefor.

Page 21, Col. 2, (Other Publications), Line 56 Delete "Americal" and insert -- American --, therefor.

Page 21, Col. 2, (Other Publications), Line 59 Delete "Chemisty," and insert -- Chemistry, --, therefor.

Page 22, Col. 1, (Other Publications), Line 6 Delete "Technolgy," and insert -- Technology, --, therefor.

Page 22, Col. 1, (Other Publications), Line 8 Delete "PEOTi02" and insert -- PEOTiO2 --, therefor.

Page 22, Col. 1, (Other Publications), Line 19 Delete "Measrure" and insert -- Measure --, therefor.

Page 22, Col. 1, (Other Publications), Line 30 Delete "Jornal" and insert -- Journal --, therefor.

Page 22, Col. 1, (Other Publications), Line 44 Delete "://www.temmoeurope.com/" and insert -- ://www.terumoeurope.com/ --, therefor.

Page 22, Col. 1, (Other Publications), Line 68 Delete "compatibilty" and insert -- compatibility --, therefor.

Page 22, Col. 2, (Other Publications), Line 59 Delete "coppeer" and insert -- copper --, therefor.

Page 22, Col. 2, (Other Publications), Line 62 Delete ""Eletrophoretic" and insert -- "Electrophoretic --, therefor.

Page 22, Col. 2, (Other Publications), Line 67 Delete "Chemisty," and insert -- Chemistry, --, therefor.

Page 23, Col. 1, (Other Publications), Line 1 Delete "ion-beam-assistend" and insert

CERTIFICATE OF CORRECTION (continued)
U.S. Pat. No. 8,449,603 B2

-- ion-beam-assisted --, therefor.

Page 23, Col. 1, (Other Publications), Line 1 Delete "deposidted" and insert -- deposited --, therefor.

Page 23, Col. 1, (Other Publications), Line 35 Delete "Vriginia," and insert -- Virginia, --, therefor.

Page 23, Col. 2, (Other Publications), Line 15 Delete "purous" and insert -- porous --, therefor.

Page 23, Col. 2, (Other Publications), Line 47 Delete "Nanotechology," and insert -- Nanotechnology, --, therefor.

Page 23, Col. 2, (Other Publications), Line 53 Delete "assembley,"" and insert -- assembly," --, therefor.

Page 24, Col. 1, (Other Publications), Line 34 Delete "Nanostructions" and insert -- Nanostructures --, therefor.

Page 24, Col. 2, (Other Publications), Line 2-3 Delete "pages245-251," and insert -- pages 245-251, --, therefor.